(12) United States Patent
Gjerde et al.

(10) Patent No.: US 7,138,518 B1
(45) Date of Patent: Nov. 21, 2006

(54) LIQUID CHROMATOGRAPHIC SEPARATION OF POLYNUCLEOTIDES

(75) Inventors: Douglas T. Gjerde, Saratoga, CA (US); Robert M. Haefele, Campbell, CA (US); Paul D. Taylor, Gilroy, CA (US); Christopher P. Hanna, Greenfield, MA (US); Alezander I. Kuklin, Collegeville, PA (US); David P. Hornby, Windes Cheshire (GB)

(73) Assignee: Transgenomic, Inc., Omaha, NE (US)

( * ) Notice: Subject to any disclaimer, the term of this patent is extended or adjusted under 35 U.S.C. 154(b) by 996 days.

(21) Appl. No.: 09/714,579

(22) Filed: Nov. 16, 2000

Related U.S. Application Data

(63) Continuation-in-part of application No. 09/562,069, filed on May 1, 2000, now Pat. No. 6,355,791, which is a continuation-in-part of application No. 09/183,123, filed on Oct. 30, 1998, now Pat. No. 6,066,258, which is a continuation-in-part of application No. 08/748,376, filed on Nov. 13, 1996, now Pat. No. 5,772,889.

(60) Provisional application No. 60/215,208, filed on Jun. 29, 2000, provisional application No. 60/220,119, filed on Jul. 21, 2000.

(51) Int. Cl.
*C07H 21/00* (2006.01)
*C12Q 1/68* (2006.01)
*B01D 15/00* (2006.01)
*B01D 15/08* (2006.01)

(52) U.S. Cl. ............... 536/25.4; 210/635; 210/656; 210/659; 210/198.2; 435/6

(58) Field of Classification Search ............... 536/23.1, 536/25.4; 435/6, 5; 210/655, 656, 198.2
See application file for complete search history.

(56) References Cited

U.S. PATENT DOCUMENTS

| | | |
|---|---|---|
| 4,458,066 A | 7/1984 | Caruthers et al. |
| 4,563,510 A | 1/1986 | Ugelstad |
| 4,683,202 A | 7/1987 | Mullis |
| 4,906,378 A | 3/1990 | Hagen et al. |
| 5,098,539 A | 3/1992 | Shieh |
| 5,100,547 A | 3/1992 | Hardiman et al. |
| 5,205,929 A | 4/1993 | Carr et al. |
| 5,207,914 A | 5/1993 | Lin |
| 5,316,680 A | 5/1994 | Frechet et al. |
| 5,334,310 A | 8/1994 | Frechet et al. |
| 5,338,448 A | 8/1994 | Gjerde |
| 5,453,185 A | 9/1995 | Frechet et al. |
| 5,522,994 A | 6/1996 | Frechet et al. |
| 5,583,162 A | 12/1996 | Li |
| 5,585,236 A * | 12/1996 | Bonn et al. ............ 435/5 |
| 5,616,701 A | 4/1997 | Woodard et al. |
| 5,645,717 A | 7/1997 | Hjerten |
| 5,647,979 A | 7/1997 | Liao |
| 5,772,889 A | 6/1998 | Gjerde et al. |
| 5,795,976 A | 8/1998 | Oefner et al. |
| 5,929,214 A | 7/1999 | Peters |
| 5,935,527 A | 8/1999 | Andrus et al. |
| 5,998,604 A | 12/1999 | Fearon et al. |
| 6,066,258 A | 5/2000 | Gjerde et al. |
| 6,174,441 B1 | 1/2001 | Gjerde et al. |
| 6,238,565 B1 | 5/2001 | Hatch |
| 6,355,791 B1 | 3/2002 | Gjerde et al. |
| 6,475,388 B1 * | 11/2002 | Gjerde et al. ............ 210/635 |
| 6,488,855 B1 * | 12/2002 | Gjerde et al. ............ 210/635 |
| 6,521,123 B1 * | 2/2003 | Gjerde et al. ............ 210/198.2 |

FOREIGN PATENT DOCUMENTS

| | | |
|---|---|---|
| EP | 0 507 591 A2 | 10/1992 |
| EP | 0 813 062 A2 | 4/1997 |
| WO | WO 94/11305 | 5/1994 |
| WO | WO 95/34359 | 12/1995 |
| WO | WO 97/19347 | 5/1997 |
| WO | WO 98/40395 | 9/1998 |
| WO | WO 98/56798 | 12/1998 |
| WO | WO 99/19514 | 4/1999 |
| WO | WO 99/44053 | 9/1999 |
| WO | WO 00/15778 | 3/2000 |
| WO | WO 01/02418 | 1/2001 |
| WO | WO 02/40130 | 5/2002 |

OTHER PUBLICATIONS

All-Chrom Newsletter Metal Components, a Potential Source of Interference in HPLC Analysis, Alltech-Applied Science, 25:1-6 (1986).

Apffel et al, Analysis of Oligonucleotides by HPLC-Electrospray Ionization Mass Spectrometry, Anal. Chem., 69:1320-1325 (1997).

(Continued)

*Primary Examiner*—Janet L. Epps-Ford
(74) *Attorney, Agent, or Firm*—Licata & Tyrrell P.C.; Keith Johnson

(57) ABSTRACT

In one aspect, the invention provides a method for separating a mixture of polynucleotides, such as DNA or RNA, including (a) applying the mixture to a polymeric separation medium having non-polar surfaces, wherein the surfaces are characterized by being substantially free from multivalent cations, such as metal ions, which are free to interfere with polynucleotide separation, and (b) eluting the mixture with a mobile phase containing organic solvent and counter ion agent. In the separation of single-stranded polynucleotides, improved separation is obtained at a temperature effective to fully denature secondary structure within the polynucleotides.

45 Claims, 19 Drawing Sheets

OTHER PUBLICATIONS

Apffel et al. Applications of HPLC for the Analysis of Doublse Stranded DNA Use of Wide Pore Sisilca Based Materials, ISPPP '97 17th International Symposium on the Separation of Proteins, Peptides & Polynucleotides, Oct. 26-29, pp. 1-5 (1997).

Barder et al. Fast Chromatography and Nonporous Silica, LC-GC, 15:10 pp. 918-926 (1997).

Berti, Dissertation, Untersuchungen Zur Ionenpaar-Umkehrphasen-Chromatographie Von DNA, pp. 52-53 (1996).

Bischoff et al, Isolation of Specific TRNAS Using an Ionic-Hydrophobic Mixed-Mode Chromatographic Matrix, Analytical Biochemistry, 151:526-533 (1985).

Cabrera et al. Silica Rod—A New Challenge in Fast High-Performance Liquid Chromatography Separations, Trends in Analytical Chemistry, 17:1 pp. 50-53 (1998).

Chen et al. High-Speed High-Performance Liquid Chromatography of Peptides and Proteins, J. of Chromatography A, 705:3-20 (1995).

Colon et al. Capillary Electrochromatography, Anal. Chem. News & Features, 461A-467A (Aug. 1, 1997).

Dadoo et al. Advances Toward the Routine Use of Capillary Electrochromatography, LC-GC, 15:630-635 (1997).

DHPLC Workshop, Stanford University, CA, pp. 32-43 (Mar. 17, 1997).

Doris et al., Quantitative Analysis of Gene Expression by Ion-Pair High-Performance Liquid Chromatography, Journal of Chromatography, 806:47-60 (1998).

Engelhardt et al. Polymer Encapsulated Stationary Phases: Advantages, Properties and Selectivities, Chromatographia, 27:11/12 pp. 535-543 (1989).

Ericson et al, Preparation of Continuous Beds for Electrochromatography and Reversed-Phase Liquid Chromatography of Low-Molecular-Mass, Journal of Chromatography A, 767:33-41 (1997).

Erikkson et al, Separation of DNA Restriction Fragments by Ion-Pair Chromatography, Journal of Chromatography, 359:265-274 (1986).

Fields, Silica Xerogel as a Continuous Column Support for High-Performance Liquid Chromatography, Anal. Chem., 68:2709-2712 (1996).

Fujimoto et al, Fritless Packed Columns for Capillary Electrochromatography: Separation of Uncharged Compounds on Hydrophobic Hydrogels Anal. Chem., 68:2753-2757 (1996).

Fujimoto et al, Capillary Electrochromatography of Small Molecules in Polyacryamide Gels with Electroosmotic Flow, Journal of Chromatography A, 716:107-113 (1995).

Gelfi et al. Detection of Point Mutations by Capillary Electrphoresis in Liquid Polymers in Temporal Thermal Gradients, Electrophoresis, 15:1506-1511 (1994).

Giovannini et al, Anal. Chem., 70:3348-3354 (1998).

Goodwin et al., Studies on the Preparation and Characterisation of Monodisperse Polystyrene Latices, Colloid & Polymer Sci., 252:464-471 (1974).

Green et al. HPLC Purification of Synthetic Oligodeoxyribonucleotides Contatining Base- and Backbone-Modified Sequences, BioTechniques, 19:5, pp. 836-841 (1993).

Green et al. Preparative Purification F Sypercoiled Plasmid DNA for Therapeutic Applications, BioPharm, 10:5 pp. 52-62 (1997).

Griffey et al, Characterization of Oligonucleotide Metabolism in Vivo Via Liquid Chromatography/Electrosspray Tandem Mass Spectrometry With a Quadrupole Ion Trap Mass Spectroeter, Journal of Mass Spectrometry, 32:305-313 (1997).

Gusev et al, Capillary Columns With in Situ Formed Porous Monolithic Packing for Micro High-Performance Liquid Chromatography and Capillary Electrochromatography, Journal of Chromatography A, 855:273-290 (1999).

Hansen et al, Highly Permeable Open-Pore Polyurethane Columns for Liquid Chromatography, Journal of Chromatography, 99:123-133 (1974).

Hayward-Lester et al, Rapid Quantification of Gene Expression by Competitive PT-PCR and Ion-Pair Reversed-Phase HPLC, BioTechniques, 20:250-257 (1996).

Hayward-Lester et al., Quantification of Specific Nucleic Acids, Regulated RNA Processing and Genomic Polymorphisms Using Reversed-Phase HPLC (undated) pp. 1-31.

He et al. Fabrication of Nanocolumns for Liquid Chromatography, Anal. Chem., 70:3790-3797 (1998).

Heftman, Chromatography, 5th Edition, Journal of Chromatography Library, Elsevier, 51A:A299-A300 (1992).

Herold et al. Recovery of Biologicaly Active Enzymes After HPLC Separation, BioChromatography, BioTechniques, 10:656-662 (1991).

Hewlett-Packard, ZORBAX Stable Bond ZORBAX Eclipse Reverse Phase HPLC Columns, Product Specification, (undated) pp. 1-10.

Hirabayashi et al. Size-Dependent Chromatographic Separation of Double-Stranded DNA Which is not Based on Gel Permeation Mode, Analytical Biochemistry, 178:336-341 (1989).

Hirabayashi, Slalom Chromatography: Size-Dependent Separation of DNA Molecules by a Hydrodynamic Phenomenon, Biochemistry, 29:9515-9521 (1990).

Hjerten et al, High-Performance Liquid Chromatography on Continuous Polymer Beds, Journal of Chromatography, 473:273-275 (1989).

Hjerten et al, Continuous Beds: High-Resolving, Cost-Effective Chromatographic Matrices, Nature, 356:810-811 (1992).

Huber et al. Detection of Partial Denaturation in At-Rich DNA Fregments Byion-Pair Reversed-Phase Chromatography, Analytical Chemistry, 68:2959-2965 (1996).

Huber et al, High-Resolution Liquid Chromatography of Oligonucleotides on Nonporous Alkylated Styrene-Divinylbenzene Copolymers, Analytical Biochemistry, 212:351-358 (1993).

Huber et al, High-Respolution Liquid Chromatography of DNA Fragments on Non-Porous Poly9styrene-Divinylbenzene) Particles, Nucleic Acid Research, 21:1061-1066 (1993).

Huber et al, Rapid Analysis of Biopolymers on Modified Non-Porous Polystyrene-Divinylbenzene Particles, Chromatographia, 37:653-658 (1993).

Huber et al. Rapid and Accurate Sizing of DNA Fragments by Ion-Pair Chromatography on Alkylated Nonporous Poly(Styrene-Divinylbenzene) Particles, Analytical Chemistry, 67:578-585 (1995).

Huber et al., Micropellicular Stationary Phases for High-Performance Liquid Chromatography of Double-Stranded DNA, J. of Chromatography A, 806: 3-30 (1998).

Huber et al, Sheath Liquid Effects Capillary High-Performance Liquid Chromatography-Electrospray Mass Spectrometry of Oligonucleotides, Journal of Chromatography A, 870:413-424 (2000).

Huber et al, Mutation Detection by Capillary Denaturing High-Performance Liquid Chromatography Using Monolithic Columns, J. Biochem. Biophys Methods, 47:5-19 (2001).

Huber et al, On-Line Cation Exchange for Suppression of Adduct Formation in Negative-Ion Electrospray Mass Spectrometry of Nucleic Acids Anal. Chem., 70:5288-5295 (1998).

Huber et al. A Comparison of Micropellicular Anion-Exchange and Reversed-Phase Stationary Phases for HPLC Analysis of Oligonucleotides, LC-GC, 14:114-127 (1996).

Iler et al., The Chemistry of Silica (1979) John Wiley & Sons, New York, pp. 566-569.

Ishizuka et al, Chromatography Properties of Miniaturized Silica Rod Columns, J. High Resol. Chromatogr., 21:477-479 (1998).

Issaq et al. Enthalpy and Entropy Effects for Hologous Solutes in HPLC With Alkul Chain Bonded Phaseses, J. of Liquid Chromatography, 12:2067-2082 (1989).

Jinno et al. Planarity Recognition of Large Polycyclic Aromatic Hydrocarbons by Various Octadecylsilica Stationary Phasees in Non-Aqueous RPLC, Chromatographia, 27:285-291 (1989).

Jorgenson, High-Respolution Separation Based on Electrophoresis and Electroosmosis, J. of Chromatography, 218:209-216 (1981).

Kato et al. Separation of DNA Restriction Fragments by High-Preformance Ion-Exchange Chromatography on a Non-Porous Ion Exchanger, Journal of Chromatography, 478:264-268 (1989).

Kwiatkowski et al. Use of RP Ion Pair Chromatography to Fractionate and Purify DNA Fragments and Monomeric Components of RNA, Acta Chemica scandinavica B., 38:721-733 (1984).
Li et al, Strategies for Faster Gradient Chromatography, LC-GC, 16:468-476 (1998).
Liao Et al, Anal. Biochem., 234:27-30 (1996).
Liu et al, Denaturing High Performance Liquid Chromatography (DHPLC) Used in the Detection of Germline and Somatic Mutaions, Nucleic Acid Research, 26:6 pp. 1396-1400 (1998).
Maa et al, Rapid High-Performance Liquid Chromatography of Ncleic Acids With Polystyrene-Based Micropellicular Anion Exchangers, Journal of Chromatography, 508:61-73 (1990).
McLuckey et al, Tandem Mass Spectrometry of Small, Multiply Charged Oligonucleotides, J. Am. Soc. Mass Spectrom., 3:60-70 (1992).
Melander et al., Mobile Phase Effects in Reversed-Phase Chromatography, J. of Chromatography, 185:99-109 (1979).
Mhatre et al., Interfacing Gradient Elution Ino-Exchange Chromatography (IEC) and Lo Angle Laser Light Scattering Photometry (LALLS) for Analysis of Proteins, J. Chromatography pp. 1-13 (Submitted for Publication) (Jul. 1991).
Minakuchi et al, Octadecylsilylated Porous Silica Rods as Separation Media for Reversed-Phase Liquid Chromatography, Anal. Chem., 68:3498-3501 (1996).
Moriyama et al. New RP HPLC Column for Oligonucleotide Separtion, Journal of Chromatography, 445:225-233 (1988).
Muddiman et al, Characterization of PCR Products From Bacilli Using Electrospray Ionization FTICR Mass Spectrometry, Anal. Chem., 68:3705-3712 (1996).
Muddiman et al, Precise Mass Measurement of a Double-Stranded 500 Base-Pair (309 kDa) Polymerase Chain Reaction Product by Negative Ion Electrospray Ionization Fourier Transform Ion Cyclotron Resonance Mass Spectrometry, Rapid Commun. Mass Spectrom., 13:1201-1204 (1999).
Nahum et al. Surface Silnols in Silica-Bonded Huydrocarbonaceous Stationary Phases, J. of Chromatography, 203:53-63 (1981).
Nakanishi et al. Double Pore Silica Gel Monolith Applied to Liquid Chromatography, J. Sol-Gel Science & Technology, 8:547-552 (1997).
Nakanishi et al., Phase Separation in Silica Sol-Gel System Containing Poly(Ethylene Oxide), Bull. Chem. Soc. Jpn., 67:1327-1335 (1994).
Nordhoff et al, Mass Spectrometry of Nucleic Acids, Mass Spectrometry Reviews, 15:67-138 (1996).
Oberacher et al, Preparation and Evaluation of Packed Capillary Columns for the Separation of Nucleic Acids by Ion-Pari Reversed-Phase High-Performance Liquid Chromatography, J. of Chrom., A 893:23-35 (2000).
Oefner et al, High-Performance Liquid Chromatography for Routine Analysis of Hepatitis C Virus CDNA/PCR Products, Research Reports, 16:1-8 (1994).
Oefner et al, High-Resolution Liquid Chromatography of Fluorescent Dye-Labeled Nucleic Acids, Analytical Biochemistry, 223:1-8 (1994).
Oefner et al, High-Resolution Liquid Chromatography of Nucleic Acids, American Laboratory, 28C-28J (1994).
Oefner et al., Poster Symposium—Session 29, Comparative DNA Sequencing by Denaturing High-Performance Liquid Chromatography (DHLPC), Am. J. Human Genet., 57:A66 (1995).
Ohmiya et al., Separation of DNA Fragments by High-Resolution Ion-Exchange Chromatography on a Nonporous QA Column, Analytical Biochemistry, 189:126-130 (1990).
Palm et al, Macroporous Polyacrylamide/Poly(Ethylene Glycol) Matrixes as Stationary Phases in Capillary Electrochromatography, Anal. Chem., 69:4499-4507 (1997).
Peters et al, Molded Rigid Polymer Monoliths as Separation Media for Caillary Electrochromatography, Anal. Chem., 69:3645-3649 (1997).
Peters et al, Molded Rigid Polymer Monoliths as Separation Media for Capillary Electrochromatography. 2. Effect of Chromatograpic Conditions on the Separation, Anal. Chem., 70:2296-2302 (1998).
Petro et al, Molded Monolithic Rod of Macroporous Poly(Styrene-Co-Divinylbenzene) as a Separation Medium for DHLC of Synthetic Polymers, Analytical Chemistry, 68: 315-321 (1996).
Pontén et al., Anal. Chem., 68:4369-4396 (1996).
Poole et al. Chromatography Today Elsevier, New York, pp. 313-342 (1991).
Potier et al, Negative Electrospray Ionization Mass Spectrometry of Synthetic and Chemically Modified Oligonucleotides, Nucleic Acids Research, 22:3895-3903 (1994).
Premstaller et al, High-Performance Liquid Chromatography-Electrospray Ionization Mass Spectrometry of Single and Double-Stranded Nucleic Acids Using Monolithic Capillary Columns, Anal. Chem., 72:4386-4393 (2000).
Pretorius et al., A New Concept for High-Speed Liquid Chromatography, J. of Chromatography, 99:23-30 (1974).
Puresyn, Inc. Communique Physical Characteristics of the Polyflo Resin (undated) pp. 1-9.
Rabel et al, Advancing Separation Science with Monolithic Silica HPLC Columns, American Laboratory, 20-22 (Dec. 2000).
Saiki et al., Enzymatic Amplification of B-Globin Genomic Sequences and Restriction Site Analysis for Diagnosis O Sickle Cell Anemia, Science, 230:1350-1354 (1985).
Schoburg et al. Immobilization of Stationary Liquids in Reversed- and Normal-Phase Liquid Chromatography, J. of Chromatography, 282:27-39 (1983).
Schoburg et al. Immobilization of Stationary Liquids of Silica Particles by Y-Radiation, Chromatographia, 18:265-274 (1984).
Seidl et al, Markroporose Styrol-Divinylbenzol-Copolymere und Ihre Verwendung in der Chromatographie und zur Darstellung von Ionenaustauschern, Adv. Polymer Sci., 5:113-213 (1967).
Snyder et al, Gradient Elution in Reversed-Phase HPLC, Anal. Chem., 55:1412A-1430A (1983).
Snyder et al. Introduction to Modern Liquid Chromatography, John Wiley & Sons, Inc., New York, pp. 173-174, 274-275 (1979).
Stober et al. Controlled Growth of Monodisperse Silica Spheres in the Micron Size Range J. of Coll. and Interface Science, 26: 62-69 (1968).
Stults et al, Improved Electrospray Ionization of Synthetic Oligodeoxynucleotides, Rapid Communication in Mass Spectrometry, vol. 5:359-363 (1991).
Suck et al, The Structure of a Trinucleoside Diphosphate: Adenylyl—(3',5')-Adenylyl-(3',5')-Adenosine Hexahydrate, Acta Cryst., B32:1727-1737 (1976).
Svec et al. Temperature, A Simple and Efficient Tool for the Control of Pore Size Distribution in Macroporous Polymers, Macromolecules, 25:7580-7582 (1995).
Thermoquest LC/MS Application Report (1999).
Tomer et al, Capillary Liquid Chromatography/Mass Spectrometry, Mass Spectrometry Reviews, 13:431-457 (1994).
Transgenomic, Inc. Technical Note General Description: DNASep (undated) pp. 1-8.
Ugelstad et al, Swellin of Oligomer-Polymer Particles. New Methods of Preparation of Emulsions and Polymer Dispersions, Advances in Colloid and Interface Science, 13:101-140 (1980).
Viklund et al, Monolithic, "Molded", Porous Materials With High Flow Characteristics for Separations, Catalysis, or Solid-Phase Chemistry: Control of Porous Properties During Polymerization, Chem. Mater., 8:744-750 (1996).
Viklund et al., Chem. Mater., 9:463-471 (1997).
Wang et al, Reversed-Phase Chromatography of Small Molecules and Peptides ona Continous Rod of Macrophorous Poly(Styrene-Codivinylbenzene), Journal of Chromatography, 669:230-235 (1994).
Wheals, Chemically Bonded Phases for Liquid Chromatography, J. of Chromatography, 107:402-407 (1975).
Yau et al., Modern Size-Exclusion Liquid Chromatography, John Wiley & Sons, New York pp. 343-381 (1979).
Xiao et al, Multiplex Capillary Denaturing High-Performance Liquid Chromatography With Laser-Induced Fluroresence Detection, BioTechniques 30:1332-1338 (2001).
AbouHaidar, et al., Non-Enzymatic RNA Hydrolysis Promoted by the Combined Catalytic Activity of Buffers and Magnesium Ions, Z. Naturforsch 54c, 542-548 (1999).

Antia, F.D., et al., High Performance Liquid Chromatography at Elevated Temperatures: Examination of Conditions for the Rapid Separation of Large Molecules, Journal of Chromatography, 435:1-15 (1998).

Ausserer, W., et al., BioTechniques, 19:1 pp. 136-139 (1995).

Azarani, Arezou, et al., Nucleic Acids Research, 29:1-9 (2001).

Baba, Yoshinobu et al., Journal of Chromatography, 618:41-55 (1993).

Bader, R., et al., Nucleosides & Nucleotides, 16:5&6 pp. 835-842 (1997).

Belenky, et al. High-Throughput Biopolymer Desalting Prior to Mass Spectrometry Using 96-Well Solid-Phase Extraction Plates, Abstract No. P9, DNA 2000 International Symposium, Boston, Mass. (2000).

Benson, J., et al., Journal of Chromatographic Science, 22:386-399 (1984).

Bullock, J., Journal of Chromatography A, 694:415-423 (1995).

Bulychev, N.V. et al., Bioorg Khim, 41:27-30 (1988).

Collins, K., et al., LCGC, LC Troubleshooting—Stainless Steel Surfaces in LC Systems, Part 1—Corrosion and Erosion, 18:688-692 (2000).

Colpan, M., et al., Journal of Chromatography, 296:339-353 (1984).

Dell'Anno, A. et al., Applied and Environmental Microbiology, 64:3283-3245 (1998).

Dickman, M., et al. Isolation of Single-Standed DNA Using Denaturing DNA Chromatography, Analytical Biochemistry, Academic Press, Inc., 284:164-165 (2000).

Djordjevic et al., HPLC Separation of Oligonucleotides in Isocratic and Temperature-Programming Mode, Analytical Chemistry, 70:1921-1925 (1998).

Dolezal, M., et al., Micropreparative Separation of Transfer Ribonucleic Acids by High-Performance Liquid Chromatography, Journal of Chromatography, 463:409-417 (1989).

Engelhardt, H., et al., Polymer Encapsulated Stationary Phases, Elsevier Science Publishers B.V., pp. 225-241 (1992).

Fritz, H., et al., High-Performance Liquid Chromatography in Polynucleotide Synthesis, Biochemistry, 17:7 pp. 1257-1267, (1978).

Furst, W., et al., Simultaneous Determination of Myocardial Nucleotides, Nucleosides, Purine Bases and Creatine Phosphate by Ion-Pair High-Performance Liquid Chrmatography, Journal of Chromatography, 578:39-44 (1992).

Garcia et al., Behaviour of Macromolecular RNA in Reversed-Phase HPLC, Journal of Chrom., Science, 21:398-404 (1983).

Georgopoulos, D.E. et al., Journal of Chromatography A, 868:109-114 (2000).

Germann, M., et al., Analytical Biochemistry, 165:399-405 (1987).

Glajch, J.L., et al., Journal of Chromatography, 384:81-90 (1987).

Grossman, L., Department of Biochemistry, The Johns Hopkins University School of Hygiene and Public Health, Methods in Enzymology, vol. XXI, Part D, pp. 95-147.

Grossman, L., Department of Biochemistry, The Johns Hopkins University School of Hygiene and Public Health, Methods in Enzymology, vol. 65, Part I, pp. 327-347.

Haky, J., et al., Journal of Chromatography, 541:303-315 (1991).

Haupt, W., et al., Comparison of Several High-Performance Liquid Chromatography Techniques for the Separation of Oligodeoxynucleotides According to Their Chain Lenghts, Journal of Chromatography, 260:419-427 (1983).

Hirata et al. Techniques of Capillary Liquid Chromatography, J. Chromatography, 186:521-528 (1979).

Houdiere, F., et al., Anal. Chem., 69:2589-2593 (1997).

Huang, G., et al., Large-Scale Purification of Synthetic Oligonucleotides and Carcinogen-Modified Oligodeoxynucleotides on a Reverse-Phase Polystyrene (PRP-1) Column Analytical Biochemistry, 190:21-25 (1990).

Huber, C.G., et al., Analysis of Nucleic Acids by Capillary Ion-Pair Reversed-Phase HPLC Coupled to Negative-Ion Electrospray Ionization Mass Spectrometry, Anal. Chem., 71:3730-3739 (1999).

Huber, C.G., et al., High-Performance Liquid Chromatographic Separation of Detritylated Oligonucleotides on Highly Cross-Linked Poly-(Sytrene-Divinylbenzene) Particles, Journal of Chromatography, 599:113-118 (1992).

Ikuta, S., et al., Anal. Chem., 56:2253-2256 (1984).

Ip, C., et al., Separation O Nucleosides and Nucleotides by Reversed-Phase HPLC With Volatile Buffers Allowing Sample Recovery, Analytical Biochemistry, 147:180-185 (1985).

Jones, A., et al., Optimal Temperature Selection for Mutation Detection by Denaturing HPLC and Comparison to Single-Stranded Conformation Polymorphism and Heteroduplex Analysis, Clinical Chem., 45:8 1133-1140 (1999).

Junemann, R., et al., In Vivo Deuteration of Transfer RNAs: Overexpression and Large-Scale Purification of Deuterated Specific tRNAs, Nucleic Acids Research, Oxford University Press, 24:5 pp. 907-913 (1996).

Kanduc, D., Fractionation of Rat Liver tRNA by Reversed-Phase High Performance Liquid Chromatography: Isolation of ISO-tRNAs, Preparative Biochemistry, 24:167-174 (1994).

Kirkland, J.J., et al. LC-GC 11:290-297 (1993).

Klink, T. A., et al., Eur. J. Biochemistry, 267:566-572 (2000).

Lalioti, V., et al. Purification and Characterization of a Novel Poly (U), Poly (C) Ribonuclease From *Saccharomyces cerevisie*, Biochimica et Biophysica Acta, 1342:62-72 (1997).

Lehninger, Principles of Biochemistry, Worth Publishers, pp. 808-809 (1982).

Li, J., et al., Anal. Chem., 69:11 pp. 2202-2206 (1997).

Li, J., et al., Anal. Chem., 69:3884-3888 (1997).

McFarland, G.D., et al., Nucleic Acids Research, 7:4 pp. 1067-1080 (1979).

McNeff, C., et al., LC-GC, Analytical Advantages of Highly Stable Stationary Phase for Reversed-Phase LC, 18:5 pp. 514-529.

Morgan, R.L., et al., Journal of Chromatography, 536:85-93 (1991).

Pager, J., Analytical Biochemistry, 215:231-235 (1993).

Petro, et al., Molded Continuous Poly (styrene-co-divinylbenzene) Rod as a Separation Medium for the Very Fast Separation of Polymers Comparison of the Chromatographic Properties of the Monolithic Rod With Columns Packed With Porous and Non-Porous Beads in HPLC of Polystyrenes, Journal of Chromatography A, 752:59-66 (1996).

Snyder, L.R., et al., Practical HPLC Method Development, John Wiley & Sons, Inc. New York, pp. 41 and 46.

Tanaka et al, High Resolution Chromatography of Ribonucleosides and Its Application to RNA Analysis, Biomedical Chromatography, 3:6 pp. 246-250 (1989).

Tashlitskii, V.N., et al., Optimization of Conditions for Ion-Pair HPLC of Oligonucleotides, Bioorg. Khim., 23:9 pp. 732-741 (1997) Biosis Abstract No. 01070821.

Topp, H., et al., Determination of Degradation Rates of Transfer & Ribosomal Ribonucleic Acids in Cultured Rat Hepatocytes by Measuring N6-Threoninocarbonyladenosine,Dihydrouridine, and Pseudouridine . . . , Analytical Biochemistry, 254:200-207 (1997).

Transgenomic, Inc., Application Note 103, Quality Control and Purification of Oligonucleotides on the WAVE Nuclei Acid Fragment Analysis System, pp. 1-3.

Trudinger, U., et al., Journal of Chromatography, 535:111-125 (1990).

Unger, K., Porous Carbon Packings for Liquid Chromatography, Analytical Chemistry, 55:3 pp. 361A-375A (1983).

Van Der Mast, C.A., et al., Separation of translationally active mRNAs by reversed-phase ion-pair high-performance liquid chromatography, Journal of Chromatography, Chrombio 5675, 564:115-125 (1991).

Passivation Procedure for Waters WISP Injectors 710/712, created on: Jun. 8, 1995; edited on: Oct. 6, 1998 (downloaded on Oct. 30, 2000).

Webster. K.R., et al., BioTechniques, 11:5 pp. 658-661 (1991).

Wincott, F., et al., Synthess, Deprotection, Analysis and Purification of RNA and Robozymes, Nucleic Acids Research, 23:14 pp. 2677-2684 (1995).

Wulfson, A. N., et al., HPLC of Nucleotides: General Methods and Their Development, Bioorg. Khim., 9:3 pp. 365 and 390 (1983) Biosis Abstract.

* cited by examiner

LIQUID CHROMATOGRAPHIC SEPARATION OF POLYNUCLEOTIDES

CROSS-REFERENCE TO RELATED APPLICATIONS

This application is a continuation-in-part of U.S. patent application Ser. No. 09/562,069 filed May 1, 2000 (now U.S. Pat. No. 6,355,791), which is a continuation-in-part of U.S. patent application Ser. No. 09/183,123 filed Oct. 30, 1998 (now U.S. Pat. No. 6,066,258), which is a continuation-in-part of U.S. patent application Ser. No. 08/748,376 filed Nov. 13, 1996 (now U.S. Pat. No. 5,772,889). This application is a regular U.S. patent application under 35 U.S.C. §111(a) and claims priority from the following commonly assigned provisional applications, filed under 35 U.S.C. 111 (b): U.S. Provisional Patent Application No. 60/215,208 filed on Jun. 29, 2000 and 60/220,119 filed on Jul. 21, 2000.

FIELD OF THE INVENTION

The present invention is directed to methods and systems for separating polynucleotides using non-polar surfaces, such as surfaces of polymeric beads and surfaces of spaces within molded monoliths, which are substantially free from contamination with multivalent cations.

BACKGROUND OF THE INVENTION

Separations of polynucleotides such as DNA have been traditionally performed using slab gel electrophoresis or capillary electrophoresis. However, liquid chromatographic separations of polynucleotides are becoming more important because of the ability to automate the analysis and to collect fractions after they have been separated. Therefore, columns for polynucleotide separation by liquid chromatography (LC) are becoming more important.

High quality materials for double stranded DNA separations previously have been based on polymeric substrates disclosed in U.S. Pat. No. 5,585,236, to Bonn, et al. (1996), which showed that double-stranded DNA can be separated on the basis of size with selectivity and performance similar to gel electrophoresis using a process characterized as reverse phase ion pairing chromatography (RPIPC). However, the chromatographic material described was limited to nonporous beads substituted with alkyl groups having at least 3 carbons because Bonn, et al. were unsuccessful in obtaining separations using polymer beads lacking this substitution. Additionally, the polymer beads were limited to a small group of vinyl aromatic monomers, and Bonn et al. were unable to effect DNA separations with other materials.

A need continues to exist for chromatographic methods for separating polynucleotides with improved separation efficiency and resolution.

SUMMARY OF THE INVENTION

In one aspect the present invention provides a method for separating a mixture containing single-stranded polynucleotides. The method includes a) applying the mixture to a polymeric separation medium having non-polar surfaces, wherein the surfaces are characterized by being substantially free from multivalent cations which are free to bind with the polynucleotides, and b) separating the mixture of polynucleotides.

The method can include detecting the polynucleotides eluting during step (b). In one embodiment, medium includes polymer beads having an average diameter of 0.5 to 100 microns, the non-polar surfaces of the beads may be unsubstituted or having bound a hydrocarbon group having from 1 to 1,000,000 carbons. The hydrocarbon group can be an alkyl group having from 1 to 24 carbons or, preferably, an alkyl group having from 1 to 8 carbons. The beads can be unsubstituted polymer beads or polymer beads substituted with a moiety selected from methyl, ethyl or hydrocarbon having from 23 to 1,000,000 carbons.

The beads can comprise a copolymer of vinyl aromatic monomers. Examples of suitable vinyl aromatic monomers include styrene, alkyl substituted styrene, alpha-methylstyrene and alkyl substituted alpha-methylstyrene. The beads can comprise a copolymer of styrene, C1–6 alkyl vinylbenzene and divinylbenzene.

In another embodiment, the non-polar surfaces are the surfaces of interstitial spaces of a polymeric monolith. The surfaces of the interstitial spaces of the monolith can be unsubstituted or substituted with a hydrocarbon group having from 1 to 1,000,000 carbons.

In preferred embodiments, polymeric monolith can be formed from monovinyl substituted aromatic compound, divinyl substituted aromatic compound, acrylate, methacrylate, polyolefin, polyester, polyurethane, polyamide, polycarbonate, fluoro-substituted ethylene, and combinations of one or more thereof. The monolith can include poly(glycidyl methacrylatecoethylene dimethacrylate). The monolith can include poly(styrene-codivinylbenzene).

Examples of multivalent cations that can bind with the polynucleotides and interfere with the separation include chromium, iron, nickel, copper and mixtures of one or more thereof.

In the invention, the separation medium preferably has been subjected to a treatment to remove any residual surface metal contaminants. One example of such a treatment includes acid wash treatment. Another example includes treatment with multivalent cation binding agent (e.g., EDTA).

In the method, the separation can be performed at a minimum denaturing temperature. The minimum denaturing temperature includes a temperature which is effective to fully denature all intramolecular hydrogen bonds within the polynucleotides in the mixture.

The method preferably includes eluting mixture of polynucleotides from the separation medium with a mobile phase comprising a counterion agent and an organic solvent, wherein said organic solvent is water soluble. Example of the solvent include alcohol, acetonitrile, dimethylformamide, tetrahydrofuran, ester, ether, and mixtures of one or more thereof. Examples of counterion include lower alkyl primary amine, lower alkyl secondary amine, lower alkyl tertiary amine, lower trialkylammonium salt, quaternary ammonium salt, and mixtures of one or more thereof. Particular example of counterion agent include octylammonium acetate, octadimethylammonium acetate, decylammonium acetate, octadecylammonium acetate, pyridiniumammonium acetate, cyclohexylammonium acetate, diethylammonium acetate, propylethylammonium acetate, propyldiethylammonium acetate, butylethylammonium acetate, methylhexylammonium acetate, tetramethylammonium acetate, tetraethylammonium acetate, tetrapropylammonium acetate, tetrabutylammonium acetate, dimethydiethylammonium acetate, triethylammonium acetate, tripropylammonium acetate, tributylammonium acetate, tetrapropylammonium acetate, tetrabutylammonium acetate, triethylammonium hexafluoroisopropyl alcohol, and mixtures of one or more thereof. The counterion agent can include an anion, such as acetate, carbonate, phosphate, sulfate, nitrate, propionate, formate, chloride, and bromide.

The separation is preferably performed by Matched Ion Polynucleotide Chromatography. The method can include detecting the polynucleotides during step (b).

The method is preferably performed at a minimum denaturing temperature, i.e. a temperature sufficient to fully denature all intramolecular hydrogen bonds within the polynucleotides.

The method can be used to separate polynucleotides such as DNA or RNA.

In certain embodiments of the method, the separation temperature is above about 40° C., can be above about 50° C., and is often above about 80° C. The temperature can be, for example, about 65° C., or about 75° C., preferably about 80° C., more preferably about 90° C. The optimum temperature will depend on the solvent and counterion used and the particular mixture being analyzed. In the method a separation temperature between about 70° C. and about 100° C. can be used. Preferably, both the mobile phase and the separation medium are retained at the elevated temperature, such as 75° C., during the separation. The single-stranded polynucleotides in the mixture may have lengths up to about 2,000 nucleotides. The method may be used with single-stranded polynucleotides having a length up to about 20,000 nucleotides.

During the separation, the mobile phase can include a multivalent cation binding agent, such as EDTA.

In the method can be used to separate single-stranded polynucleotides that incorporate a chemical tag. The tag can be a non-polar tag such as a hydrocarbon group, examples of which include alkyl, cycloalkyl, aryl and arylalkyl groups. The tag can be a fluorescent label.

In another aspect, the invention concerns a method for separating single-stranded polynucleotides that exist in a mixture with impurities. In one embodiment, the method includes a) flowing the mixture through a separation column containing polymer beads having an average diameter of 0.1 to 100 microns, the beads having non-polar surfaces, wherein the surfaces are characterized by being substantially free from multivalent cations which are free to bind with the polynucleotides in the mixture, and b) eluting the mixture with a mobile phase containing a counterion agent. The method is preferably performed at a minimum denaturing temperature. The method can include detecting the polynucleotides eluting during step (b). Examples of such impurities include failure sequences, salts, buffers, or proteins. The method can include collecting the polynucleotides separately from the impurities. The beads can be unsubstituted or having bound a hydrocarbon group having from 1 to 1,000,000 carbons. The hydrocarbon group can be an alkyl group having from 1 to 24 carbons or, preferably, an alkyl group having from 1 to 8 carbons. In another embodiment, the separation column containing a polymeric monolith having non-polar surfaces, the non-polar surfaces are the surfaces of interstitial spaces of the polymeric monolith. The surfaces may be unsubstituted or substituted with a hydrocarbon group having from 1 to 1,000,000 carbons. The hydrocarbon group may be an alkyl group having from 1 to 24 carbons, preferably having from 1 to 8 carbons. The polymeric monolith has preferably been subjected to an acid wash treatment, or treatment with multivalent cation binding agent, in order to substantially remove multivalent cation contaminants. The polymeric monolith can be a selected from monovinyl substituted aromatic compound, divinyl substituted aromatic compound, acrylate, methacrylate, polyolefin, polyester, polyurethane, polyamide, polycarbonate, fluoro-substituted ethylene, and combinations of one or more thereof. In a particular example, the monolith includes poly(glycidyl methacrylatecoethylene dimethacrylate). In another example, the monolith includes poly(styrene-codivinylbenzene). The method preferably includes eluting the mixture from the surfaces with a mobile phase containing an organic solvent and a counterion agent, wherein the organic solvent is water soluble.

In still another aspect, the invention concerns a method for separating single-stranded polynucleotides. The method includes a) flowing the mixture through a separation column containing polymer beads having an average diameter of 0.1 to 100 microns, and b) separating said mixture of polynucleotides at a minimum denaturing temperature. The method can include detecting the polynucleotides eluting during step (b). The surfaces of the beads may be unsubstituted or have bound a hydrocarbon group having from 1 to 1,000,000 carbons. The hydrocarbon group can be an alkyl group having from 1 to 24 carbons or, preferably, an alkyl group having from 1 to 8 carbons. In one embodiment, the non-polar surfaces are the surfaces of interstitial spaces of a polymeric monolith.

In yet another aspect, the invention concerns a method for separating single-stranded polynucleotides that exist in a mixture with impurities. In one embodiment, the method includes a) flowing the mixture through a separation column containing polymer beads having an average diameter of 0.1 to 100 microns, and b) eluting the mixture with a mobile phase containing a counterion agent at a minimum denaturing temperature. The method can include detecting the polynucleotides eluting during step (b). Examples of such impurities include failure sequences, salts, buffers, or proteins. The method can include collecting the polynucleotides separately from the impurities.

In still yet another aspect, the invention concerns a method for separating a mixture comprising single-stranded polynucleotides. The method includes a) applying the mixture to a polymeric separation medium having non-polar surfaces, wherein the surfaces are characterized by being substantially free from multivalent cations which are free to interfere with polynucleotide separation, and (b) separating said mixture of polynucleotides. The multivalent cations can include multivalent metal cations which are free to interfere with polynucleotide separation. Examples of such metal cations include Fe(III), Cu(II) or Cr(III).

DETAILED DESCRIPTION OF THE INVENTION

Figure 1:
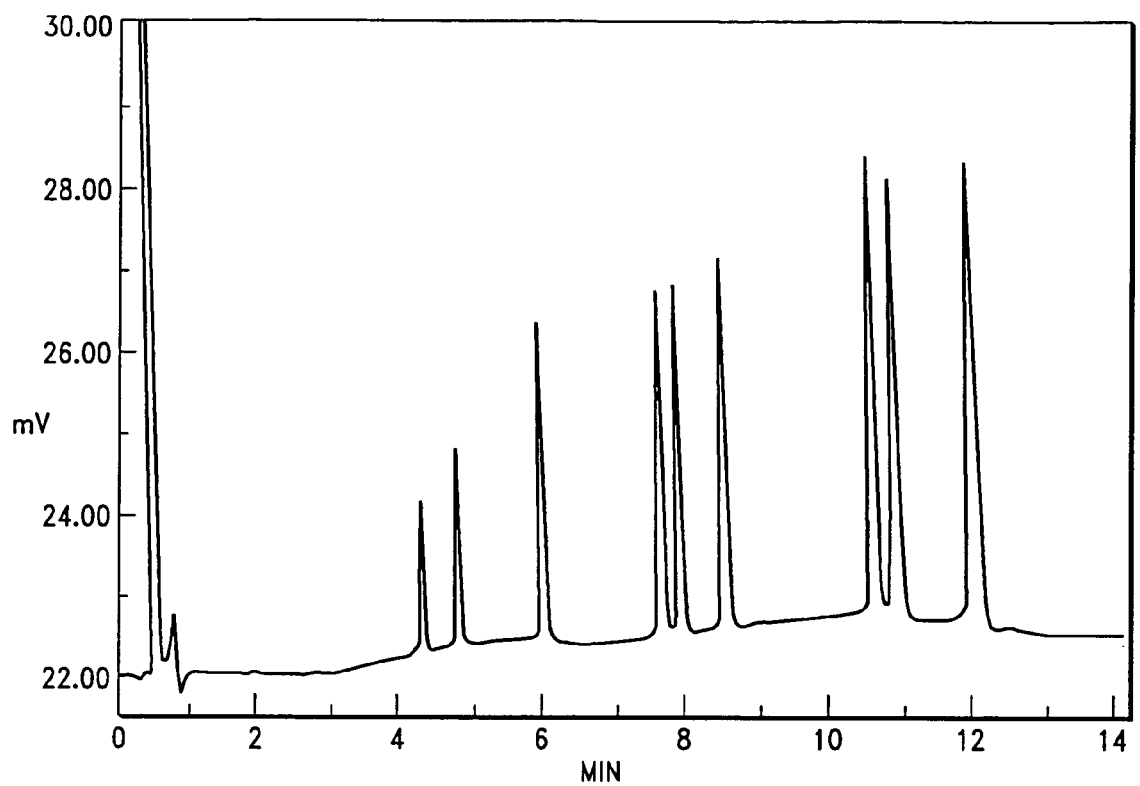
FIG. 1 is an example of a separation of double-stranded polynucleotides using alkylated beads and acetonitrile as solvent.

In one aspect, the present invention concerns a Matched Ion Polynucleotide Chromatography (MIPC) method and system for separating a mixture of polynucleotides.

In its most general form, the subject matter of the present invention concerns the separation of single-stranded or double-stranded polynucleotides utilizing a stationary separation medium having non-polar surfaces. The preferred surfaces are substantially free from multivalent cations which are free to bind with the polynucleotides. The separation is performed on the stationary surface. The surface can be porous, but preferably any surface pores are of a size which excludes the smallest polynucleotide being analyzed.

The medium can be enclosed in a column. In one embodiment, the non-polar surfaces comprise the surfaces of polymeric beads. In an alternative embodiment, the surfaces comprise the surfaces of interstitial spaces in a molded polymeric monolith. For purposes of simplifying the description of the invention and not by way of limitation, the separation of polynucleotides using nonporous beads, and the preparation of such beads, will be primarily described herein, it being understood that other separation surfaces, such as the interstitial surfaces of polymeric monoliths, are intended to be included within the scope of this invention. Monoliths, such as rods, contain polymer separation media which have been formed inside a column as a unitary structure having through pores or interstitial spaces which allow eluting solvent and analyte to pass through and which provide the non-polar separation surface.

In general, the only requirement for the separation media of the present invention is that they must have a surface that is either intrinsically non-polar or be bonded with a material that forms a surface having sufficient non-polarity to interact with a counterion agent.

In one aspect, the subject matter of the present invention is the separation of polynucleotides utilizing columns filled with nonporous polymeric beads having an average diameter of about 0.5–100 microns; preferably, 1–10 microns; more preferably, 1–5 microns. Beads having an average diameter of 1.0–3.0 microns are most preferred.

"Matched Ion Polynucleotide Chromatography" (MIPC) as defined herein, includes a process for separating single and double-stranded polynucleotides using non-polar reverse phase media, wherein the process uses a counterion agent, and an organic solvent to release the polynucleotides from the reverse phase media.

Embodiments of the MIPC process are described in earlier, co-pending and commonly assigned U.S. patents or patent applications: U.S. Pat. Nos. 5,772,889; 5,997,742; 5,972,222; 5,986,085; 6,017,457; 6,030,527; 6,056,877; 6,066,258; U.S. patent application Ser. No. 09/058,580 filed Apr. 10, 1998 (abandoned); Ser. No. 09/169,440 filed Oct. 9, 1998; Ser. No. 09/318,407 filed May 25, 1999; Ser. No. 09/350,737 filed Jul. 9, 1999; Ser. No. 09/557,424 filed Mar. 21, 2000; and Ser. No. 09/562,069 filed May 1, 2000, each of which patents or patent applications is incorporated by reference in its entirety herein.

The preferred MIPC system provides automated options for sample selection, mobile phase gradient selection and control, column and mobile phase temperature control, and fraction collection.

In general, the only requirement for the separation media of the present invention is that they must have a surface that is either intrinsically non-polar or be bonded with a material that forms a surface having sufficient non-polarity to interact with a counterion agent.

Without wishing to be bound by theory, the preferred beads for use in polynucleotide separation as described herein have a pore size which essentially excludes the polynucleotide molecules being separated from entering the bead. As used herein, the term "nonporous" is defined to denote a bead which has surface pores having a diameter that is less than the size and shape of the smallest polynucleotide molecule in the mixture in the solvent medium used therein. Included in this definition are polymer beads having these specified maximum size restrictions in their natural state or which have been treated to reduce their pore size to meet the maximum effective pore size required.

The surface conformations of nonporous beads of the present invention can include depressions and shallow pit-like structures which do not interfere with the segregation process. A pretreatment of a porous bead to render it nonporous can be effected with any material which will fill the pores in the bead structure and which does not significantly interfere with the MIPC process.

Pores are open structures through which mobile phase and other materials can enter the bead structure. Pores are often interconnected so that fluid entering one pore can exit from another pore. Applicants believe that pores having dimensions that allow movement of the polynucleotide into the interconnected pore structure and into the bead impair the separation of polynucleotide molecules or result in separations that have very long retention times. In MIPC, however, the preferred beads are "nonporous" and the polynucleotides do not enter the bead structure.

In the present invention, the definition of "polynucleotide" includes reference to a chain of either deoxyribonucleotides, ribonucleotides, or 2'-alkoxy ribonucleotides or a combination thereof, having from a few, e.g. 2–20, to many, e.g. up to 20,000, nucleotides. The term includes deoxyribonucleic acids (DNA) and ribonucleic acids (RNA). The term also includes chains of nucleosides linked by analogs of the phosphate bond, e.g. phorphoramidites, phosphorothioates, and the like or combinations thereof. The polynucleotide may be a natural, phosphate-linked polynucleotide, or it may be any of a wide variety of known polynucleotide analogs.

Polynucleotides may comprise single-stranded molecules or may comprise double-stranded molecules. Single-stranded polynucleotides may include intramolecular hydrogen bonds between bases. An example of intramolecular hydrogen bonds is the secondary structure of RNA (see Lehninger, Principles of Biochemistry pp. 874–876 (Worth Publishers, 1982)).

The term "secondary structure" refers to the manner in which successive bases of a polynucleotide are arranged in space. The secondary structure results from hydrogen bonding patterns between bases. For example, single-stranded DNA or RNA can poses such intramolecular hydrogen bonding patterns. An example of such a structure includes haripin loops.

"Double-stranded polynucleotide" refers to antiparallel strands having intermolecular hydrogen bonds between complimentary bases. The two strands in a duplex can be completely complimentary. Alternatively, the two strands can be partially complimentary, such as in a hybrid duplex, in which the two strands include mismatches between the strands or a deletion in one strand.

As defined herein, a "chemical tag" includes a molecule which can be covalently bound to a polynucleotide for the purpose of increasing the sensitivity of detection of the polynucleotide (e.g., a label) and/or increasing the retention time of the polynucleotide during separation by MIPC.

A "tagged polynucleotide" includes a polynucleotide which has been modified by covalent attachment of a chemical tag. The location of the chemical tag can occur at either end of a polynucleotide fragment or at an intermediate location. Multiple tags can be attached. However, in a preferred embodiment, a single molecule of chemical tag is attached to a polynucleotide. In a most preferred embodiment, the tag is attached to the 5' end.

An example of tagged polynucleotide includes a PCR primer having a covalently attached fluorescent chemical tag at the 5' end. Such a primer can be used in a PCR amplification to incorporate the chemical tag into dsDNA.

In a particular aspect, the invention concerns a method for analyzing a mixture which includes tagged polynucleotides by Matched Ion Polynucleotide Chromatography. Examples of suitable non-polar tags include a hydrocarbon group such as alkyl, cycloalkyl, aryl and arylalkyl groups. Preferably, the tagged polynucleotide/counterion complex is essentially completely soluble in the mobile phase at all concentrations of organic solvent used in the mobile phase during the MIPC separation. In this context, the term "alkyl" describes straight or branched hydrocarbon radical chains of 1 to 8 carbons atoms and preferably 1 to 24 carbon atoms. Examples of these alkyl groups include, but are not limited to methyl, ethyl, propyl, iso-propyl, butyl, tert-butyl, pentyl, and hexyl. The terms "aryl" and "arylalkyl" describe aromatic radical groups and can include monocyclic, bicyclic, and tricyclic aromatic hydrocarbon groups. Example of these aromatic groups, include, but are not limited to phenyl, naphthyl, and pyrenyl. The hydrocarbon group can also be substituted with various functional groups such as aldehyde, ketone, ester, ether, alkyl, alkoxy, halogen (e.g., Cl, F, Br, or I), haloalkyl, polyhaloalkyl, hydroxy, cyano, and nitro.

Preferred tagging groups include FAM, JOE, TAMRA, and ROX (Operon Technologies, Inc., Alameda, Calif.). These groups can be covalently attached to a desired primer by reaction with a 5'-amino-modified oligonucleotide in the presence of sodium bicarbonate and dimethylformamide. Alternatively, covalently tagged primers can be obtained commercially (e.g., from Midland Certified Reagent, Co. or Operon Technologies, Inc. Alameda, Calif.). Fluorescent dyes are available form Molecular Probes, Inc. (Eugene, Oreg.) and Amersham Life Science. Inc. (Cleveland, Ohio).

"Fully denaturing conditions" includes reference to conditions under which all intermolecular and intramolecular hydrogen bonds between paired bases are disrupted.

The "minimum denaturing temperature" is defined herein to include a temperate sufficient for fully denaturing all intramolecular and intermolecular hydrogen bonds between paired bases in a polynucleotide or within each of the polynucleotides in a mixture.

The "separation temperature" includes reference to the temperature of the separation medium and of the mobile phase in contact with the separation medium. In the present invention, it is assumed that the column oven heats both the separation medium and the mobile phase flowing through the separation medium to about the same temperature.

In carrying out the MIPC method of the invention, the polynucleotide sample to be analyzed is typically injected and pre-mixed with the mobile phase prior to elution on the separation medium. The sample is then contacted directly with the separation media, or alternatively, is passed through a "pre-conditioning" tubing or pre-column to allow the sample and mobile phase to equilibrate before contact with the separation medium.

In one embodiment, the mobile phase components are introduced into a mixer inside the column oven and mixed prior to contact with the sample. Alternatively, the mobile phase components may be mixed at ambient temperature and contacted with the sample injector, also maintained at ambient temperature outside of the column oven. In a preferred embodiment, the sample is injected into the mobile phase, pre-equilibrated to the temperature of the column. In this manner, a near-direct connection between the column and the injector is provided to minimize diffusion and enhance sample resolution.

Alternately, when utilizing a low-pressure HPLC system, sample mixing typically occurs at ambient temperature. In instances in which the autosampler does not provide for heating the injection port to column temperature, standard HPLC tubing (e.g., 0.005–0.01" diameter) may be positioned between the injector and the column, to heat the mobile phase and induce denaturation of the polynucleoitde sample. The tubing is preferably made of PEEK (polyether ether ketone) or titanium. The length of the tubing is typically determined based upon the efficiency of heat transfer. The entire length of the pre-column may be maintained at oven temperature, or, only a portion of the pre-column may be heated. The sample is passed through the pre-column and then contacted with the separation medium for subsequent elution.

An example of a preferred column heating system for use in the present invention is described in U.S. Pat. No. 6,103,112 (incorporated by reference herein in its entirety).

"Separating" as defined herein includes a MIPC process for separating polynucleotide molecules in which the retention time of a molecule is primarily based on nucleotide length. In the case of single-stranded molecules, the retention time can be subject to bias due to the influence of the polarity of the bases. The bias can either increase or decrease the retention time.

Chromatographic efficiency of the column beads is predominantly influenced by the properties of surface and near-surface areas. For this reason, the following descriptions are related specifically to the close-to-the-surface region of the polymeric beads. The main body and/or the center of such beads can exhibit entirely different chemistries and sets of physical properties from those observed at or near the surface of the polymeric beads of the present invention.

The nonporous polymeric beads of the present invention can be prepared by a two-step process in which small seed beads are initially produced by emulsion polymerization of suitable polymerizable monomers. The emulsion polymerization procedure of the invention is a modification of the procedure of Goodwin, et al. (Colloid & Polymer Sci., 252:464–471 (1974)). Monomers which can be used in the emulsion polymerization process to produce the seed beads include styrene, alkyl substituted styrenes, alpha-methyl styrene, and alkyl substituted alpha-methyl styrene. The seed beads are then enlarged and, optionally, modified by substitution with various groups to produce the nonporous polymeric beads of the present invention.

The seed beads produced by emulsion polymerization can be enlarged by any known process for increasing the size of the polymer beads. For example, polymer beads can be enlarged by the activated swelling process disclosed in U.S. Pat. No. 4,563,510. The enlarged or swollen polymer beads are further swollen with a crosslinking polymerizable monomer and a polymerization initiator. Polymerization increases the crosslinking density of the enlarged polymeric bead and reduces the surface porosity of the bead. Suitable crosslinking monomers contain at least two carbon—carbon double bonds capable of polymerization in the presence of an initiator. Preferred crosslinking monomers are divinyl monomers, preferably alkyl and aryl (phenyl, naphthyl, etc.) divinyl monomers and include divinyl benzene, butadiene, etc. Activated swelling of the polymeric seed beads is useful to produce polymer beads having an average diameter ranging from 1 up to about 100 microns.

Alternatively, the polymer seed beads can be enlarged simply by heating the seed latex resulting from emulsion polymerization. This alternative eliminates the need for activated swelling of the seed beads with an activating solvent. Instead, the seed latex is mixed with the crosslinking monomer and polymerization initiator described above, together with or without a water-miscible solvent for the crosslinking monomer. Suitable solvents include acetone, tetrahydrofuran (THF), methanol, and dioxane. The resulting mixture is heated for about 1–12 hours, preferably about 4–8 hours, at a temperature below the initiation temperature of the polymerization initiator, generally, about 10° C.–80° C., preferably 30° C.–60° C. Optionally, the temperature of the mixture can be increased by 10–20% and the mixture heated for an additional 1 to 4 hours. The ratio of monomer to polymerization initiator is at least 100:1, preferably about 100:1 to about 500:1, more preferably about 200:1 in order to ensure a degree of polymerization of at least 200. Beads having this degree of polymerization are sufficiently pressure-stable to be used in high pressure liquid chromatography (HPLC) applications. This thermal swelling process allows one to increase the size of the bead by about 110–160% to obtain polymer beads having an average diameter up to about 5 microns, preferably about 2–3 microns. The thermal swelling procedure can, therefore, be used to produce smaller particle sizes previously accessible only by the activated swelling procedure.

Following thermal enlargement, excess crosslinking monomer is removed and the particles are polymerized by exposure to ultraviolet light or heat. Polymerization can be conducted, for example, by heating of the enlarged particles to the activation temperature of the polymerization initiator and continuing polymerization until the desired degree of polymerization has been achieved. Continued heating and polymerization allows one to obtain beads having a degree of polymerization greater than 500.

In the present invention, the packing material disclosed by Bonn et al. or U.S. Pat. No. 4,563,510 can be modified through substitution of the polymeric beads with alkyl groups or can be used in its unmodified state. For example, the polymer beads can be alkylated with 1 or 2 carbon atoms by contacting the beads with an alkylating agent, such as methyl iodide or ethyl iodide. Alkylation is achieved by mixing the polymer beads with the alkyl halide in the presence of a Friedel-Crafts catalyst to effect electrophilic aromatic substitution on the aromatic rings at the surface of the polymer blend. Suitable Friedel-Crafts catalysts are well-known in the art and include Lewis acids such as aluminum chloride, boron trifluoride, tin tetrachloride, etc. The beads can be hydrocarbon substituted by substituting the corresponding hydrocarbon halide for methyl iodide in the above procedure, for example.

The term "alkyl" as used herein in reference to the beads of the present invention is defined to include alkyl and alkyl substituted aryl groups, having from 1 to 1,000,000 carbons, the alkyl groups including straight chained, branch chained, cyclic, saturated, unsaturated nonionic functional groups of various types including aldehyde, ketone, ester, ether, alkyl groups, and the like, and the aryl groups including as monocyclic, bicyclic, and tricyclic aromatic hydrocarbon groups including phenyl, naphthyl, and the like. Methods for alkyl substitution are conventional and well-known in the art and are not an aspect of this invention. The substitution can also contain hydroxy, cyano, nitro groups, or the like which can modulate the polarity of reverse phase surface.

In the present invention, successful separation of polynucleotide molecules can be achieved using underivatized nonporous beads as well as using beads derivatized with alkyl groups having 1 to 1,000,000 carbons. In preferred embodiments, the polymer is unsubstituted or is substituted with a moiety selected from the group consisting of methyl, ethyl, or hydrocarbon having from 23 to 1,000,000 carbons.

The base polymer of the invention can also be other polymers, non-limiting examples of which include mono- and di-vinyl substituted aromatics such as styrene, substituted styrenes, alpha-substituted styrenes and divinylbenzene; acrylates and methacrylates; polyolefins such as polypropylene and polyethylene; polyesters; polyurethanes; polyamides; polycarbonates; and substituted polymers including fluorosubstituted ethylenes commonly known under the trademark TEFLON. The base polymer can also be mixtures of polymers, non-limiting examples of which include poly(styrene-divinylbenzene) and poly(ethylvinylbenzene-divinylbenzene). Methods for making beads from these polymers are conventional and well known in the art (for example, see U.S. Pat. No. 4,906,378). The physical properties of the surface and near-surface areas of the beads are the predominant influence on chromatographic efficiency. The polymer, whether derivatized or not, preferably provides a nonporous, non-reactive, and non-polar surface for the MIPC segregation.

In another embodiment of the present invention, the separation medium can be in the form of a polymeric monolith such as a rod-like monolithic column. The monolithic column is polymerized or formed as a single unit inside of a tube as described in the Examples hereinbelow. The through-pore or interstitial spaces provide for the passage of eluting solvent and analyte materials. The separation is performed on the stationary surface. The surface can be porous, but is preferably nonporous. The form and function of the separations are identical to columns packed with beads. As with beads, the pores contained in the rod must be compatible with polynucleotides and not trap the material. The rod preferably is characterized by being substantially free from multivalent cations which are free to bind with polynucleotides.

The molded polymeric rod of the present invention is prepared by bulk free radical polymerization within the confines of a chromatographic column. The base polymer of the rod can be produced from a variety of polymerizable monomers. For example, the monolithic rod can be made from polymers, including mono- and di-vinyl substituted aromatic compounds such as styrene, substituted styrenes, alpha-substituted styrenes and divinylbenzene; acrylates and methacrylates; polyolefins such as polypropylene and polyethylene; polyesters; polyurethanes; polyamides; polycarbonates; and substituted polymers including fluorosubstituted ethylenes commonly known under the trademark TEFLON. The base polymer can also be mixtures of polymers, non-limiting examples of which include poly(glycidyl methacrylate-co-ethylene dimethacrylate), poly(styrene-divinylbenzene) and poly(ethylvinylbenzene-divinylbenzene. The rod can be unsubusited or substituted with a substituent such as a hydrocarbon alkyl or an aryl group. The alkyl group optionally has 1 to 1,000,000 carbons inclusive in a straight or branched chain, and includes straight chained, branch chained, cyclic, saturated, unsaturated nonionic functional groups of various types including aldehyde, ketone, ester, ether, alkyl groups, and the like, and the aryl groups includes as monocyclic, bicyclic, and tricyclic aromatic hydrocarbon groups including phenyl, naphthyl, and the like. In a preferred embodiment, the alkyl group has 1–24 carbons. In a more preferred embodiment, the alkyl group has 1–8 carbons. The substitution can also contain hydroxy, cyano, nitro groups, or the like which are considered to be non-polar, reverse phase functional groups. Methods for hydrocarbon substitution are conventional and well-known in the art and are not an aspect of this invention. The preparation of polymeric monoliths is by conventional methods well known in the art as described in the following references: Wang et al. (*J. Chromatog. A* 699:230 (1994)), Petro et al. (*Anal. Chem.* 68:315 (1996)), and the following U.S. Pat. Nos. 5,334,310; 5,453,185; 5,522,994 (to Frechet). Monolith or rod columns are commercially available form Merck & Co (Darmstadt, Germany).

In an important aspect of the present invention, the beads and other media of the invention are characterized by being substantially free from multivalent cations which are free to bind with the polynucleotides. The preferred beads are characterized by having been subjected to precautions during production, including a decontamination treatment, such as an acid wash treatment, designed to substantially eliminate any multivalent cation contaminants which can interfere with the separation of polynucleotides (e.g. Fe(III), Cr(III), or colloidal metal contaminants). Preferably, only very pure, non-metal containing materials are used in the production of the beads in order that the resulting beads will have minimum metal content.

In addition to the beads themselves being substantially metal-free, Applicants have also found that, to achieve optimum peak separation during MIPC, the separation column and all process solutions held within the column or flowing through the column are preferably substantially free of multivalent cation contaminants which are free to bind with polynucleotides. As described in commonly owned U.S. Pat. Nos. 5,772,889; 5,997,742; and 6,017,457 this can be achieved by supplying and feeding solutions that enter separation column with components which have process solution-contacting surfaces made of material which does not release multivalent cations into the process solutions held within or flowing through the column, in order to protect the column from contamination with multivalent cations that can interfere with the separation of polynucleotides. The process solution-contacting surfaces of the system components are preferably material selected from the group consisting of titanium, coated stainless steel, passivated stainless steel, and organic polymer.

There are two places where multivalent cation binding agents, e.g., chelators, can be used in MIPC separations. In one embodiment, these binding agents can be incorporated into a solid through which the mobile phase passes. Contaminants are trapped before they reach places within the system that can harm the separation. In these cases, the functional group is attached to a solid matrix or resin (e.g., a flow-through cartridge, usually an organic polymer, but sometimes silica or other material). The capacity of the matrix is preferably about 2 mequiv./g. An example of a suitable chelating resin is available under the trademark CHELEX 100 (Dow Chemical Co.) containing an iminodiacetate functional group.

In another embodiment, the multivalent cation binding agent can be added to the mobile phase. The binding functional group is incorporated into an organic chemical structure. The preferred multivalent cation binding agent fulfills three requirements. First, it is soluble in the mobile phase. Second, the complex with the metal is soluble in the mobile phase. Multivalent cation binding agents such as EDTA fulfill this requirement because both the chelator and the multivalent cation binding agent-metal complex contain charges which make them both water-soluble. Also, neither precipitate when acetonitrile, for example, is added. The solubility in aqueous mobile phase can be enhanced by attaching covalently bound ionic functionality, such as, sulfate, carboxylate, or hydroxy. A preferred multivalent cation binding agent can be easily removed from the column by washing with water, organic solvent or mobile phase. Third, the binding agent must not interfere with the chromatographic process. The concentration of the binding agent in the mobile phase is typically in the range of 0.1 to 10 mM, and often 1 mM.

The multivalent cation binding agent can be a coordination compound. Examples of preferred coordination compounds include water soluble chelating agents and crown ethers. Non-limiting examples of multivalent cation binding agents which can be used in the present invention include acetylacetone, alizarin, aluminon, chloranilic acid, kojic acid, morin, rhodizonic acid, thionalide, thiourea, $\alpha$-furildioxime, nioxime, salicylaldoxime, dimethylglyoxime, $\alpha$-furildioxime, cupferron, $\alpha$-nitroso-$\alpha$-naphthol, nitroso-R-salt, diphenylthiocarbazone, diphenylcarbazone, eriochrome black T, PAN, SPADNS, glyoxal-bis(2-hydroxyanil), murexide, $\alpha$-benzoinoxime, mandelic acid, anthranilic acid, ethylenediamine, glycine, triaminotriethylamine, thionalide, triethylenetetramine, EDTA, metalphthalein, arsonic acids, $\alpha,\alpha'$-bipyridine, 4-hydroxybenzothiazole, 8-hydroxyquinaldine, 8-hydroxyquinoline, 1,10-phenanthroline, picolinic acid, quinaldic acid, $\alpha,\alpha',\alpha''$-terpyridyl, 9-methyl-2,3,7-trihydroxy-6-fluorone, pyrocatechol, salicylic acid, tiron, 4-chloro-1,2-dimercaptobenzene, dithiol, mercaptobenzothiazole, rubeanic acid, oxalic acid, sodium diethyldithiocarbarbamate, and zinc dibenzyldithiocarbamate. These and other examples are described by Perrin in *Organic Complexing Reagents: Structure, Behavior, and Application to Inorganic Analysis*, Robert E. Krieger Publishing Co. (1964). In the present invention, a preferred multivalent cation binding agent is EDTA.

To achieve optimal results, it is generally necessary to tightly pack the chromatographic column with the solid phase polymer beads. Any known method of packing the column with a column packing material can be used in the present invention to obtain adequate high resolution separations. Typically, a slurry of the polymer beads is prepared using a solvent having a density equal to or less than the density of the polymer beads. The column is then filled with the polymer bead slurry and vibrated or agitated to improve the packing density of the polymer beads in the column. Mechanical vibration or sonication are typically used to improve packing density.

For example, to pack a 50×7.8 mm ID column, 3.0 grams of beads can be suspended in 15 mL of methanol with the aid of sonication. The suspension is then packed into the column using 100 mL of methanol at 8,000 psi pressure. This improves the density of the packed bed.

There are several types of counterions suitable for use with MIPC. These include a mono-, di-, or trialkylamine that can be protonated to form a positive counter charge or a quaternary alkyl substituted amine that already contains a positive counter charge. The alkyl substitutions may be uniform (for example, triethylammonium acetate or tetrapropylammonium acetate) or mixed (for example, propyldiethylammonium acetate). The size of the alkyl group may be small (methyl) or large (up to 30 carbons) especially if only one of the substituted alkyl groups is large and the others are small. For example octyldimethylammonium acetate is a suitable counterion agent. Preferred counterion agents are those containing alkyl groups from the ethyl, propyl or butyl size range.

The purpose of the alkyl group is to impart a nonpolar character to the polynucleotides through a matched ion process so that the polynucleotides can interact with the nonpolar surface of the reverse phase media. The requirements for the extent of nonpolarity of the counterion-polynucleotide pair depends on the polarity of the reverse phase media, the solvent conditions required for polynucleotide separation, the particular size and type of molecules being separated. For example, if the polarity of the reverse phase media is increased, then the polarity of the counterion agent may have to change to match the polarity of the surface and increase interaction of the counterion-polynucleotide pair. Triethylammonium acetate is preferred although quaternary ammonium reagents such as tetrapropyl or tetrabutyl ammonium salts can be used when extra nonpolar character is needed or desired.

In the mobile phase of the present method, an organic solvent that is water soluble is preferably used, for example, alcohols, nitriles, dimethylformamide (DMF), tetrahydrofuran (THF), esters, and ethers. Water soluble solvents are defined as those which exist as a single phase with aqueous systems under all conditions of operation of the present invention. Solvents which are particularly preferred for use in the method of this invention include methanol, ethanol, 2-propanol, 1-propanol, tetrahydrofuran (THF), and acetonitrile, with acetonitrile being most preferred overall.

In some cases, it may be desired to increase the range of concentration of organic solvent used to perform the segregation. For example, increasing the alkyl length on the counterion agent will increase the nonpolarity of the counterion-polynucleotide pair resulting in the need to either increase the concentration of the mobile phase organic component, or increase the strength of the organic component type. There is a positive correlation between concentration of the organic solvent required to elute a fragment from the column and the length of the fragment. However, at high organic solvent concentrations, the polynucleotide could precipitate. To avoid precipitation, a strong organic solvent or a smaller counterion alkyl group can be used. The alkyl group on the counterion reagent can also be substituted with halides, nitro groups, or the like to moderate polarity.

The mobile phase preferably contains a counterion agent. Typical counterion agents include trialkylammonium salts of organic or inorganic acids, such as lower alkyl primary, secondary, and lower tertiary amines, lower trialkyammonium salts and lower quaternary alkyalmmonium salts. Lower alkyl refers to an alkyl radical of one to six carbon atoms, as exemplified by methyl, ethyl, n-butyl, i-butyl, t-butyl, isoamyl, n-pentyl, and isopentyl. Examples of counterion agents include octylammonium acetate, octadimethylammonium acetate, decylammonium acetate, octadecylammonium acetate, pyridiniumammonium acetate, cyclohexylammonium acetate, diethylammonium acetate, propylethylammonium acetate, propyldiethylammonium acetate, butylethylammonium acetate, methylhexylammonium acetate, tetramethylammonium acetate, tetraethylammonium acetate, tetrapropylammonium acetate, tetrabutylammonium acetate, dimethydiethylammonium acetate, triethylammonium acetate, tripropylammonium acetate, tributylammonium acetate, tetrapropylammonium acetate, and tetrabutylammonium acetate. Although the anion in the above examples is acetate, other anions may also be used, including carbonate, phosphate, sulfate, nitrate, propionate, formate, chloride, and bromide, or any combination of cation and anion. These and other agents are described by Gjerde, et al. in *Ion Chromatography*, 2nd Ed., Dr. Alfred Hüthig Verlag Heidelberg (1987). Counterion agents that are volatile are preferred for use in the method of the invention, with triethylammonium acetate (TEAA) and triethylammonium hexafluoroisopropyl alcohol being most preferred.

The mobile phase can include a chelating agent which can be present at a concentration of about 0.01 to about 10.0 mM. Examples of preferred chelating agents include water soluble chelating agents and crown ethers. Non-limiting examples of multivalent chelating agents which can be used in the present invention include acetylacetone, alizarin, aluminon, chloranilic acid, kojic acid, morin, rhodizonic acid, thionalide, thiourea, α-furildioxime, nioxime, salicylaldoxime, dimethylglyoxime, α-furildioxime, cupferron, α-nitroso-β-naphthol, nitroso-R-salt, diphenylthiocarbazone, diphenylcarbazone, eriochrome black T, PAN, SPADNS, glyoxal-bis(2-hydroxyanil), murexide, α-benzoinoxime, mandelic acid, anthranilic acid, ethylenediamine, glycine, triaminotriethylamine, thionalide, triethylenetetramine, EDTA, metalphthalein, arsonic acids, α,α'-bipyridine, 4-hydroxybenzothiazole, 8-hydroxyquinaldine, 8-hydroxyquinoline, 1,10-phenanthroline, picolinic acid, quinaldic acid, α,α',α"-terpyridyl, 9-methyl-2,3,7trihydroxy-6-fluorone, pyrocatechol, salicylic acid, tiron, 4-chloro-1,2-dimercaptobenzene, dithiol, mercaptobenzothiazole, rubeanic acid, oxalic acid, sodium diethyldithiocarbarbamate, and zinc dibenzyldithiocarbamate. These and other examples are described by Perrin in *Organic Complexing Reagents: Structure, Behavior, and Application to Inorganic Analysis*, Robert E. Krieger Publishing Co. (1964). In the present invention, a preferred multivalent cation binding agent is EDTA.

In one aspect, the present invention provides a method for separating a mixture comprising double-stranded polynucleotides. In a preferred embodiment, the method includes (a) applying the mixture to a polymeric separation medium having non-polar surfaces, wherein the surfaces are characterized by being substantially free from multivalent cations which are free to bind with the polynucleotides in the mixture, and (b) separating the mixture of polynucleotides. The method preferably includes eluting the mixture with a mobile phase containing a counterion agent and an organic solvent. In a preferred embodiment, the mixture is eluted from the separation medium at a minimum denaturing temperature. This temperature effective to fully denature all intermolecular hydrogen bonds between paired bases in the polynucleotides in the mixture.

In another aspect, the present invention provides a method for separating a mixture comprising double-stranded polynucleotides. In a preferred embodiment, the method includes (a) applying the mixture to a polymeric separation medium having non-polar surfaces, wherein the surfaces are characterized by being substantially free from multivalent cations which are free to bind with the polynucleotides in the mixture, and (b) separating the mixture of polynucleotides. The method preferably includes eluting the mixture with a mobile phase containing a counterion agent and an organic solvent. In a preferred embodiment, the mixture is eluted from the separation medium at a minimum denaturing temperature.

In another aspect, the present invention provides a method for separating a mixture comprising single-stranded polynucleotides. In a preferred embodiment, the method includes (a) applying the mixture to a polymeric separation medium having non-polar surfaces, and (b) separating the mixture of polynucleotides. The method preferably includes eluting the mixture with a mobile phase containing a counterion agent and an organic solvent. In a preferred embodiment, the mixture is eluted from the separation medium at a temperature effective to fully denature all intramolecular hydrogen bonds between paired bases in the polynucleotides in the mixture.

In a further aspect, the present invention provides a method for separating a mixture comprising single-stranded polynucleotides. In a preferred embodiment, the method includes (a) applying the mixture to a polymeric separation medium having non-polar surfaces, as described herein, and (b) separating the mixture of polynucleotides. The method preferably includes eluting the mixture with a mobile phase containing a counterion agent and an organic solvent. In a preferred embodiment, the mixture is eluted from the separation medium at a temperature effective to fully denature all intramolecular hydrogen bonds between paired bases in the polynucleotides in the mixture. Also in a preferred embodiment, the surfaces are characterized by being substantially free from multivalent cations which are free to bind with the polynucleotides in the mixture. In a particular embodiment, the method comprises a) flowing the mixture through a separation column containing polymer beads having an average diameter of 0.5 to 100 microns, said beads being unsubstituted polymer beads or polymer beads substituted with a moiety selected from the group consisting of hydrocarbon having from 1 to 1,000,000 carbons, and b) separating said mixture of polynucleotides at a minimum denaturing temperature. The polynucleotides can comprise comprise DNA, RNA, or a mixture of these molecules.

In one embodiment of the practice of the method of the invention, a liquid sample containing polynucleotides is injected onto a MIPC chromatography column containing a reverse phase support. In sample, the polynucleotides are paired with a counterion and then subjected to reverse phase chromatography using the nonporous beads, or other media, as described herein. Aqueous mobile phase containing counterion reagent is applied to the column at an initial concentration of organic component that is low enough such that all of the polynucleotide molecules of interest bind to the column. The polynucleotide molecules elute as the concentration of organic component in the mobile phase is increased. The concentration of organic component preferably is applied as a gradient in order to elute the polynucleotide molecules. The gradient can be a linear gradient, although curved or step gradients can also be used.

In a preferred embodiment of the method, the elution is carried out under conditions effective to completely denature the polynucleotide molecules. For example, the denaturation can be accomplished by conducting the elution at a temperature of at least about 55° C., preferably above about 75° C., and more preferably above 80° C. The temperature is preferably within the range of about 75° C. to about 100° C. For some separations, the maximum temperature can be up to about 120° C.

The pH of the mobile phase is preferably within the range of about pH 5 to about pH 9, and optimally within the range of about pH 6 to about pH 7.5.

Fractions eluting from the MIPC system can be collected as a single fraction or as a plurality of fractions. The collection can be performed manually or using an automated fraction collector.

The method of the invention can be used to separate double-stranded polynucleotide molecules having lengths from 5 to 100 base pairs. The method is especially useful in separating double-stranded polynucleotide molecules having a length up to about 2,000 base pairs.

The method of the invention can be used to separate single-stranded polynucleotide molecules having lengths from 5 to 100 nucleotides. The method is especially useful in separating single-stranded polynucleotide molecules having a length of about 200 to about 2000 nucleotides. The method can be used in separating single-stranded poynucleotide molecules having lengths up to about 20,000 nucleotides.

An advantage of the instant invention is that polynucleotide separation by MIPC can be accomplished in about 10–30 min, in contrast to conventional gel chromatography which can require hours or days.

In a particular aspect, the invention involves a method for separating polynucleotide molecules, such as single-stranded polynucleotides, from impurities. The method includes a) applying the polynucleotide molecules to a Matched Ion Polynucleotide Chromatography column as described herein, and b) eluting the column to separate the polynucleotide molecules from the impurities. Example of such impurities include failure sequences, salts, buffers, proteins, chemical reagents used in synthesis of polynucleotides. The elution is preferably conducted at a temperature that denatures the secondary structure of the polynucleotide molecules. The method preferably includes detecting the presence of polynucleotide molecules eluted from the column in the mobile phase, such as by UV detection. Mobile phase fractions containing the selected polynucleotide molecules can be collected during the elution.

Particular examples of the separation of polynucleotide molecules are described in the examples herein.

The present invention is also based in part on Applicants' surprising discovery that separations of single-stranded polynucleotides by MIPC is improved when the separation medium is free, or substantially free, from multivalent cations that are free to bind with the polynucleotides being separated. As described in the Examples hereinbelow, contamination of a separation column with multivalent cations, such as Cr(III), markedly inhibits the ability to analyze single-stranded poynucleotides, and also tagged polynucleotides (Examples 22 and 23), by MIPC.

Applicants have further surprisingly discovered that the requirement in MIPC for using a separation medium that is free from multivalent cations that are free to bind with the polynucleotides being separated is even more stringent when the separations were performed at elevated temperatures. As described in Example 16, contamination of a separation column with multivalent cations, such as Cr(III), markedly inhibits the ability to analyze a synthetically prepared single-stranded poynucleotide. An unexpected result was that this inhibition was more pronounced when the analysis was performed at an elevated column temperature (Example 17). Thus at a separation temperature of 50° C., contamination of the column with Cr(III) ions markedly lowered the percent recovery of single-stranded polynucleotide. The performance of the column could be restored by repeatedly injecting onto the column a solution of EDTA. However, in a similar set of experiments but conducted at a separation temperature of 75° C. (Example 17), the performance of the column could not be restored even after multiple injections of the EDTA solution as had been used in the experiments performed at 50° C.

The present invention is based in part on Applicants' surprising discovery that separations of single-stranded polynucleotides by MIPC is improved when the separation conducted at temperatures greater than the minimal denaturing temperature. Temperature has a marked effect on the ability to analyze single-stranded polynucleotides by MIPC. As shown in FIGS. 26–29 (Examples 20 and 21), temperature affected both the resolution and recovery of single-stranded RNA fragments as analyzed by MIPC. Both the resolution and the recovery improved when performing the separation at elevated temperatures. Compared to the result obtained at 40° C., improved separation was obtained when the temperature was 50° C. Further improvement was obtained at 65° C. Still further improvement was obtained at a temperature of 75° C. As described in Example 25, contamination of a separation column with multivalent cations, such as Cr(III), markedly inhibits the ability to analyze a mixture of RNA molecules.

Another example of an RNA separation is described in Example 26 (FIG. 37) in which a sample of total RNA from a plant source was applied to a reverse phase column of the invention and eluted at 75° C. Peaks were observed for different classes of RNA in order of their respective sizes with tRNA (70–150 nt) eluting first, followed by rRNA (1,500 to 3,700 nt). rRNA, the most abundant species, appeared as two large peaks between about 13–15 min. and had the greatest area under the curve. mRNA having an average size of about 5–10K nt eluted at about 17 min. (indicated by arrow 50).

Another example of the effect of temperature on the analysis of single-stranded polynucleotides is described in Example 24. Four polynucleotides were designed and synthesized to have a sequence at the 5' end which was complementary to the sequence at the 3' end, with a random 20 nucleotide sequence in between the complementary sequences. These polynucleotides were designed to have a hairpin loop secondary structure at non-denaturing temperatures. A fifth molecule was designed to have a random sequence and without complementary ends. Each polynucleotide was analyzed using MIPC at a series of different column temperatures from 40° C. to 80° C. A plot of retention time vs. analysis temperature (FIG. 31) indicated a linear relationship for the random sequence polynucleotide. However, for most of the polynucleotides that were predicted to have a hairpin loop at lower temperatures, shorter retention times than expected were observed at temperatures below about 50–55° C. One non-limiting explanation for this observation is that retention time of the hairpin form of a molecule is shorter than that of the extended form.

Thus, the presence of secondary structure decreased the retention time of some of the polynucleotides. This could interfere with the analysis and purification of a polynucleotide. For example, a secondary structure that causes a polynucleotide to co-elute with a by-product (e.g. a failure sequence in a preparation of a synthetic polynucleotide) would be undesired. Applicants have discovered that when performing the separation at elevated temperature, such as at 75° C., this undesired reduction in retention time was eliminated. A non-limiting explanation for this observation is that running the separation at the higher temperature eliminates the secondary structure from the polynucleotides which then exist in extended form. In the extended form, there are more sites to interact with the separation medium.

Figure 30:
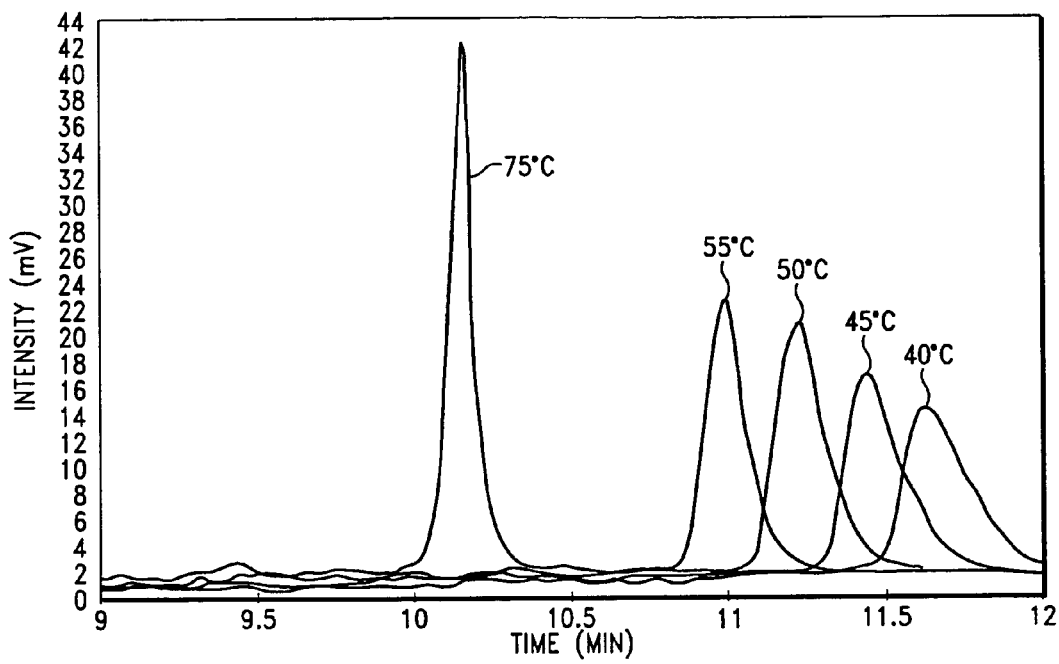
FIG. 30 is an example of a MIPC analysis, at different temperatures, of a single-stranded polynucleotide using alkylated beads and acetonitrile as solvent.

Applicants have also unexpectedly observed that higher separation temperature also increased separation efficiency. For example, as shown in FIG. 30, for the same injection quantity, peak width was reduced at higher temperature, and the peak height increased. This would result in improved resolution between components and allow more rapid separations.

Other features of the invention will become apparent in the course of the following descriptions of exemplary embodiments which are given for illustration of the invention and are not intended to be limiting thereof.

EXAMPLE 1

Preparation of Nonporous
Poly(Styrene-Divinylbenzene) Particles

Sodium chloride (0.236 g) was added to 354 mL of deionized water in a reactor having a volume of 1.0 liter. The reactor was equipped with a mechanical stirrer, reflux condenser, and a gas introduction tube. The dissolution of the sodium chloride was carried out under inert atmosphere (argon), assisted by stirring (350 rpm), and at an elevated temperature (87° C.). Freshly distilled styrene (33.7 g) and 0.2184 g of potassium peroxodisulfate ($K_2S_2O_8$) dissolved in 50 mL of deionized water were then added. Immediately after these additions, the gas introduction tube was pulled out of the solution and positioned above the liquid surface. The reaction mixture was subsequently stirred for 6.5 hours at 87° C. After this, the contents of the reactor were cooled down to ambient temperature and diluted to a volume yielding a concentration of 54.6 g of polymerized styrene in 1000 mL volume of suspension resulting from the first step. The amount of polymerized styrene in 1000 mL was calculated to include the quantity of the polymer still sticking to the mechanical stirrer (approximately 5–10 g). The diameter of the spherical beads in the suspension was determined by light microscopy to be about 1.0 micron.

Beads resulting from the first step are still generally too small and too soft (low pressure stability) for use as chromatographic packings. The softness of these beads is caused by an insufficient degree of crosslinking. In a second step, the beads are enlarged and the degree of crosslinking is increased.

The protocol for the second step is based on the activated swelling method described by Ugelstad et al. (*Adv. Colloid Interface Sci.*, 13:101–140 (1980)). In order to initiate activated swelling, or the second synthetic step, the aqueous suspension of polystyrene seeds (200 ml) from the first step was mixed first with 60 mL of acetone and then with 60 mL of a 1-chlorododecane emulsion. To prepare the emulsion, 0.206 g of sodium dodecylsulfate, 49.5 mL of deionized water, and 10.5 mL of 1-chlorododecane were brought together and the resulting mixture was kept at 0° C. for 4 hours and mixed by sonication during the entire time period until a fine emulsion of <0.3 microns was obtained. The mixture of polystyrene seeds, acetone, and 1-chlorododecane emulsion was stirred for about 12 hours at room temperature, during which time the swelling of the beads occurred. Subsequently, the acetone was removed by a 30 minute distillation at 80° C.

Following the removal of acetone, the swollen beads were further grown by the addition of 310 g of a ethyldivinylbenzene and divinylbenzene (DVB) (1:1.71) mixture also containing 2.5 g of dibenzoylperoxide as an initiator. The growing occurred with stirring and with occasional particle size measurements by means of light microscopy.

After completion of the swelling and growing stages, the reaction mixture was transferred into a separation funnel. In an unstirred solution, the excess amount of the monomer separated from the layer containing the suspension of the polymeric beads and could thus be easily removed. The remaining suspension of beads was returned to the reactor and subjected to a stepwise increase in temperature (63° C. for about 7 hours, 73° C. for about 2 hours, and 83° C. for about 12 hours), leading to further increases in the degree of polymerization (>500). The pore size of beads prepared in this manner was below the detection limit of mercury porosimetry (<30 Å).

After drying, the dried beads (10 g) from step two were washed four times with 100 mL of n-heptane, and then two times with each of the following: 100 mL of diethylether, 100 mL of dioxane, and 100 mL of methanol. Finally, the beads were dried.

EXAMPLE 2

Acid Wash Treatment

The beads prepared in Example 1 were washed three times with tetrahydrofuran and two times with methanol. Finally the beads were stirred in a mixture containing 100 mL tetrahydrofuran and 100 mL concentrated hydrochloric acid for 12 hours. After this acid treatment, the polymer beads were washed with a tetrahydrofuran/water mixture until neutral (pH=7). The beads were then dried at 40° C. for 12 hours.

EXAMPLE 3

FIG. 1 shows the high resolution separation of DNA restriction fragments using octadecyl modified, nonporous poly(ethylvinylbenzene-divinylbenzene) beads. The experiment was conducted under the following conditions: Column: 50×4.6 mm I.D.; mobile phase 0.1 M TEAA, pH 7.2; gradient: 33–55% acetonitrile in 3 min, 55–66% acetonitrile in 7 min, 65% acetonitrile for 2.5 min; 65–100% acetonitrile in 1 min; and 100–35% acetonitrile in 1.5 min. The flow rate was 0.75 mL/min, detection UV at 260 nm, column temp. 51° C. The sample was 5 μL (=0.2 μg pUC18 DNA-HaeIII digest).

EXAMPLE 4

Bromination of Remaining Double Bonds on the Surface of Poly(Styrene-Divinylbenzene) Polymer Beads 50.0 g of a poly(styrene-divinylbenzene) polymer beads were suspended in 500 g of tetrachloromethane. The suspension was transferred into a 1000 mL glass reactor (with attached reflux condenser, separation funnel and overhead stirrer). The mixture was kept at 20° C. Bromine (100 mL) was added over a period of 20 minutes. After addition was completed, stirring continued for 60 minutes. The temperature was raised to 50° C. to complete the reaction (2 hours).

The polymer beads were separated from the tetrachloromethane and excess bromine by means of centrifugation and cleaned with tetrahydrofuran (once with 100 mL) and methanol (twice with 100 mL). The polymer beads were dried at 40° C.

The polymer beads are packed into a 50×4.6 mm ID column.

EXAMPLE 5

Nitration of a Poly(Styrene-Divinylbenzene) Polymer Beads

In a 1000 mL glass reactor 150 mL of concentrated nitric acid (65%) were combined with 100 mL concentrated sulfuric acid. The acid mixture was cooled to 0–4° C. When the temperature had dropped to <4° C., 50 g of poly(styrene-divinylbenzene) polymer beads were added slowly under continuous stirring. After addition was completed, 50 mL of nitric acid (65%) was added. The suspension was stirred for three hours, maintaining a temperature of 5–10° C.

On the next day the reaction was quenched by adding ice to the suspension. The polymer beads were separated from the acid by means of centrifugation. The polymer beads were washed to neutrality with water, followed by washing steps with tetrahydrofurane (four times with 100 mL) and methanol (four times with 100 mL). The polymer beads were dried at 40° C.

The polymer beads are packed into a 50×4.6 mm i.d column.

EXAMPLE 6

Preparation of a Non-Polar Organic Polymer Monolith Chromatography Column

A chromatography tube in which the monolith polymeric separation medium is prepared is made of stainless steel. The monomers, styrene (Sigma-Aldrich Chemical Corp.) and divinylbenzene (Dow Chemical Corp.) are dried over magnesium sulfate and distilled under vacuum.

To a solution of a 1:1 mixture by volume of the distilled styrene and divinylbenzene, containing 1% by weight (with respect to monomers) of azobisisobutyronitrile (AIBN), is added eight volumes of a solution of the porogenic solvent, dodecyl alcohol and toluene (70:30). The solution so prepared is bubbled with nitrogen for 15 minutes and is used to fill a chromatography tube (50×8 mm I.D.) sealed with a rubber nut plug at the bottom end. The tube is then sealed at the top end with a rubber nut plug and the contents are allowed to polymerize at 70° C. for 24 hours.

Following polymerization, the rubber plugs are replaced by column end fittings and the column is connected to an HPLC system. The HPLC instrument has a low-pressure mixing quaternary gradient capability. A cartridge or guard column containing an iminodiacetate multivalent cation capture resin is placed in line between the column and the mobile phase source reservoir. The column is then washed by flowing 100 mL of tetrahydrofuran (THF) at 1 mL/min through the column to remove the dodecyl alcohol and toluene, thereby creating through-pores in the otherwise solid polymer monolith.

In this example, all of the flow paths are either titanium, sapphire, ceramic, or PEEK, except for the tube body, which is 316 stainless steel. The interior of the 316 stainless steel tube is passivated with dilute nitric acid prior to use.

EXAMPLE 7

Acid Wash Treatment to Remove Multivalent Metal Cation Contaminants

The non-polar, organic polymer monolith column is washed by flowing tetrahydrofuran through the column at a flow rate of 2 mL per minute for 10 minutes followed by flowing methanol through the column at 2 mL per minute for 10 minutes. The non-polar, organic polymer monolith column is washed further by flowing a mixture containing 100 mL of tetrahydrofuran and 100 mL of concentrated hydrochloric acid through the column at 10 mL per minute for 20 minutes. Following this acid treatment, the non-polar, organic polymer monolith column is washed by flowing tetrahydrofuran/water (1:1) through the column at 2 mL per minute until neutral (pH 7).

EXAMPLE 8

Bromination of Remaining Double Bonds on the Surface of Non-Polar Organic Polymer Monolith Column Any double bonds remaining on the surface of the monolith column prepared in Example 6 are reacted with bromine as described in Example 4.

EXAMPLE 9

Nitration of a Non-Polar Organic Polymer Monolith Column

The non-polar organic polymer column prepared in Example 6 is nitrated as described in Example 5.

EXAMPLE 10

Alkylation of Poly(Styrene-Divinylbenzene) Polymer Beads

The following procedures were carried out under nitrogen (Air Products, Ultra Pure grade, Allentown, Pa.) at a flow rate of 250–300 mL/min. 25 g of the beads prepared in Example 1 were suspended in 150–160 g of 1-chlorooctadecane (product no. 0235, TCI America, Portland, Oreg.) using a bow shaped mixer (use a 250 mL wide neck Erlenmeyer flask). The temperature was set to 50–60° C. to prevent the 1-chlorooctadecane from solidifying. Larger pieces of polymer were broken up to facilitate suspending. The solution was mixed using a stirrer (Model RZRI, Caframo, ONT NOH2T0, Canada) with the speed set at 2. The polymer suspension was transferred into a three neck bottle (with reflux condenser, overhead stirrer and gas inlet). 52–62 g of 1-chlorooctadecane were used to rinse the Erlenmeyer flask and were added to the three neck bottle. The bottle was heated in an ethylene glycol bath set at 80° C. The solution was mixed using a stirrer (Caframo) with the speed set at 0. After 20 minutes, the reaction was started by addition of 1.1 g $AlCl_3$ powder (product no. 06218, Fluka, Milwaukee, Wis.) and continued for 16–18 h.

After the reaction, the polymer was separated from excess 1-chlorooctadecane by centrifugation followed by consecutive washing steps:

| Addition | Comment |
| --- | --- |
| 50 mL conc. HCl, 50–60 mL n-heptane | 4 repetitions, with recycled heptane |
| 100 mL $H_2O$, 50–60 mL n-heptane | 1 repetition, with fresh heptane |
| 50 mL conc. HCl, 50–60 mL n-heptane | 1 repetition, with fresh heptane |
| 100 mL $H_2O$, 50–60 mL n-heptane | 1 repetition, fresh heptane |
| 150 mL $H_2O$, no n-heptane | 3 repetitions, use plastic stirrer to break up chuncks of polymer beads. Repeat steps 4 and 5 three times. Shake for two minutes with no centrifugation. |
| 100 mL THF | 3 repetitions |
| 100 mL THF/n-heptane | 1 repetition |
| 100 mL n-heptane | 1 repetition |
| 100 mL THF | 1 repetition |
| 100 mL $CH_3OH$ | 4 repetitions |

In the steps where aqueous solvents (HCl or $H_2O$) were used, the polymer was shaken for 30 seconds with the aqueous phase before adding n-heptane. n-Heptane was then added and the mixture was shaken vigorously for 2 min. After the final polymeric beads were dried at 40–50° C. for 2–3 hr, they were ready for packing.

EXAMPLE 11

Column Packing Procedure

After weighing out 3 grams of oven dried polymeric beads (from Example 10), a slurry was formed with 10 mL tetrahydrofuran (THF) and placed in a sonicator under a fume hood for 15 min. 5 mL of THF and 5 mL of methanol (MeOH) were added followed by sonication for an additional 10 min. A packing assembly was pre-filled with 20 mL MeOH. The slurry was slowly poured into the packing assembly. A Haskel pump (Haskel International, Inc., Burbank, Calif.) was turned on and the packing pressure was slowly increased to 5000 psi for the initial packing phase. After 10 min, the packing pressure was slowly increased to 9000 psi and the secondary packing phase set for 20 min. After 20 min, the packing eluent was changed from MeOH to 0.05 M $Na_4EDTA$. The final packing phase was set for 40 min.

EXAMPLE 12

Preparation of Monolithic Capillary Columns

Fused silica capillary tubing (360 μm OD×250 μm ID, Polymicro Technologies, Phoenix, Ariz.) was flushed successively with 0.1M and 1M NaOH, water (Milli Q System, Millipore, Bedford, Mass.) and methanol (Anhydrous, EM Science, Gibbstown, N.J.) in order to deprotonize the surface silanol groups. The capillary tubing was dried by passing $N_2$ through it.

The capillary tubing was cut in 1 m sections prior to the following surface treatment: The capillaries sections were filled with a 50% (v/v) solution of 3-(trimethoxysilyl)propyl acrylate (Sigma-Aldrich, St. Louis, Mo.) and 3-(trimethoxysilyl)propyl methacrylate (Sigma-Aldrich), respectively in dimethylformamide (EM Science). This solution contained also 0.01% (w/v) 2,2 diphenylpicryl hydrazyl radical (Sigma-Aldrich) in order to inhibit polymerization of the acrylate and methacrylate groups, respectively. After degassing the solution with He for 20 minutes the capillaries were filled with the solution and put into an oven at 90° C. for about 12 hours. In orderto prevent migration of the solution inside the tubing during the treatment, one end of each capillary tube was immersed in a 1 mL reservoir of the solution retained in an Eppendorf centrifugation tube. The open end of the tube was sealed to the capillary using glue ("Super Strength Adhesive, 3M"). The treated capillary tubing was extensively flushed with dimethylformamide (Omnisolve for HPLC, EM Science) and anhydrous methanol (EM Science) and blown dry by passing $N_2$ through the capillary.

To form a monolithic capillary column, each dry capillary tube (1 m) was gravity filled with monomer-porogen-initiator mixture. The following three different recipes for the mixture were used in which all chemicals were used without further purification:

Capillary monolith C-1 included the following components: 500 μL divinylbenzene (80%) (Sigma-Aldrich); 500 μL styrene (98%), (Sigma-Aldrich); 1300 μL 1-decanol (99%), (Alfa Aesar, Ward Hill. MA); 200 μL tetrahydrofuran (99%), (Omnisolve for HPLC, EM Science); and 25 mg 2,2' azobisisobutyronitrile (Alfa Aesar, Ward Hill. MA).

Capillary monolith C-2 included the following components: 250 μL divinylbenzene (80%); 750 μL styrene (98%); 1300 μL 1-decanol (98%); 200 μL tetrahydrofuran (99%); and 25 mg 2,2' azobisisobutyronitrile.

Capillary monolith C-3 included the following components: 500 μL divinylbenzene (80%); 500 μL styrene (98%); 2600 μL 1-decanol (98%); 200 μL tetrahydrofuran (99%); and 25 mg 2,2' azobisisobutyronitrile.

During polymerization, one end of each tube was immersed in a reservoir of monomer-porogen-initiator mixture retained in a tube as described above. The mixture within the tube was polymerized for 24 h at 75° C. for C-1,18 h at 80° C. for C-2, and 18 h at 90° C. for C-3.

In order to remove unreacted monomers, oligomers and the porogen after polymerization, each monolith was flushed with tetrahydrofuran (Omnisolve, EM Science) and methanol (Anhydrous, EM Science). The pump was set to constant pressure at 350 bar. The flow rate was estimated to be 3–6 µL/min. The temperature was 90° C. Flushing with THF and methanol took approximately 24 hours per 50 cm of monolithic capillary.

EXAMPLE 13

Separation of DNA Using a Polystyrene/Divinylbenxene Monolithic Capillary Column A monolithic capillary column (250 µm ID×145 mm length), prepared as described for the C-1 monolith, was used in this example. Chromatography was performed using an HPLC system configured with a Dionex GP50 pump (Dionex Corp., Sunnyvale, Calif.), a Hitachi L7200 autosampler (Hitachi Ltd., Tokyo, Japan) fitted with a 100 µL sample loop, a Hitachi L7300 column oven, a Valco (Valco Instrument Co., Houston, Tex.) stainless steel tee with 10–32 fittings and a Spectra-Physics Model 100 variable wavelength absorbance detector fitted with a capillary flow cell adapter. A 100 µm×70 mm polyimide coated fused silica capillary (Polymicro Technologies, Phoenix, Ariz.) was used for detection by thermal removal (burning off) the polyimide coating to create an optical detection window.

Data was acquired using Dionex PeakNet Chromatography workstation with a Dionex UI20 universal interface for digitizing the analog signal from the absorbance detector.

The system was configured with an eluent preheat tubing which consisted of 1.5 m of 0.010 ID×0.062 OD PEEK tubing (Upchurch Scientific, Oak Habor, Wash.). The preheat tubing was place in the oven and the oven temperature set to 80° C. In order to minimize the distance from the outlet of the monolithic separation capillary to the detector, the separation capillary was placed outside the oven. The preheat tubing and separation capillary were connected to the stainless steel mixing tee. Connected to the third port of the mixing tee was 2 m of 0.010 ID×0.062 OD PEEK tubing (Upchurch Scientific). Connected at the waste end of the tee was a 10-32 PEEK coupler and a 10-32 PEEK plug. The plug was tightened into the coupler in order to create sufficient backpressure to cause flow through the high pressure separation capillary. At approximately 2500 psi, the flow through the separation capillary and into the detection capillary was about 3 µL/min. Under these conditions, the majority of the flow (497 µL/min) passed through the waste line port of the mixing tee.

Mobile phase buffers were prepared using reagent or HPLC grade chemicals and deionized water. Buffer A consisted of 100 mM triethylammonium acetate (TEM, Transgenomic, Inc., San Jose, Calif.) and 1 mM tetrasodium ethylenediamine tetraacetic acid (EDTA). Buffer B consisted of 100 mM triethylammonium acetate, 1 mM EDTA and 25% (v/v) acetonitrile.

A sample comprising a 20-mer polynucleotide (obtained from Operon Technologies as described below) was injected onto the system and eluted using the following gradient:

| Time (min) | % B |
|---|---|
| 0.0 | 30 |
| 5.0 | 70 |
| 7.0 | 90 |
| 8.1 | 90 |
| 8.2 | 30 |

The injection volume was 0.5 µL (split from 100 µL). The pressure was 2450 psi. The temperature of the mixing tee was 47° C. The detection was by UV at 254 nm. The flow rate was 3 µL/min (split from 500 µL/min). The 20-mer polynucleotide, having a sequence of:

5'-CGACCTCCCTTTATCCTCCACAGATCTCA-3' (SEQ ID NO. 1), was obtained from Operon Technologies (Alameda, Calif.) as "unpurified" grade and was diluted in TE buffer (10 mM Tris-HCl, pH 8.0, 1 mM EDTA) to 100 µM prior to injection.

Figure 2:
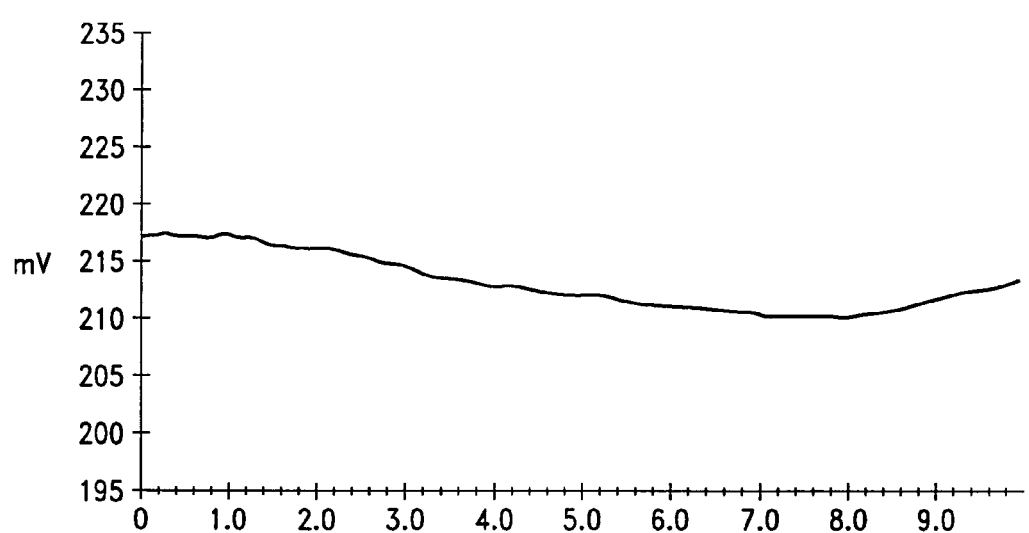
FIG. 2 illustrates an elution profile obtained using a monolithic capillary column.
Figure 3:
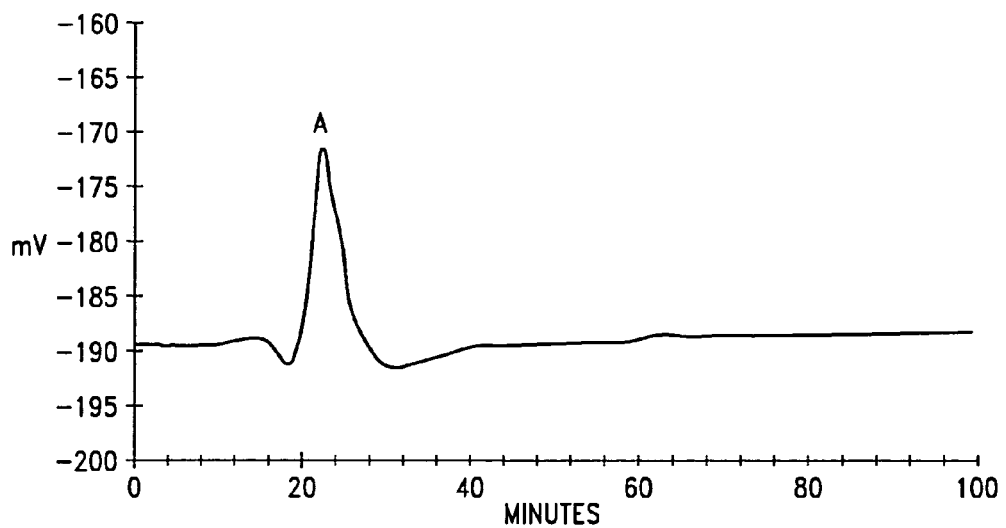
FIG. 3 illustrates an elution profile of a 20 nucleotide fragment from the monolithic capillary column used for FIG. 2 after the column was treated with EDTA.

Using the system described above, initial injections of the 20 mer single-stranded synthetic polynucletotide sample showed no detector response (FIG. 2). Metal contamination was suspected, possibly from the stainless steel injection valve, sample loop or mixing tee. Ten consecutive injections (30 seconds apart) of 100 µL of 0.2 M tetrasodium ethylenediamine tetraacetic acid (EDTA) were performed. Injection of the 20 mer polynucleotide still did not reveal a detector response. For additional cleaning, 1 mM EDTA was added to each of the eluents. The system was allowed to run overnight with 100% eluent B. The 20-mer polynucleotide was again injected, and eluted as the peak labeled "A" as shown in FIG. 3.

In another injection, after the overnight EDTA cleaning, a sample containing a mixture of single-stranded and double-stranded DNA was injected onto the system and eluted using the following gradient:

| Time (min) | % B |
|---|---|
| 0.0 | 30 |
| 5.0 | 70 |
| 7.0 | 90 |
| 8.1 | 90 |
| 8.2 | 30 |

Figure 4:
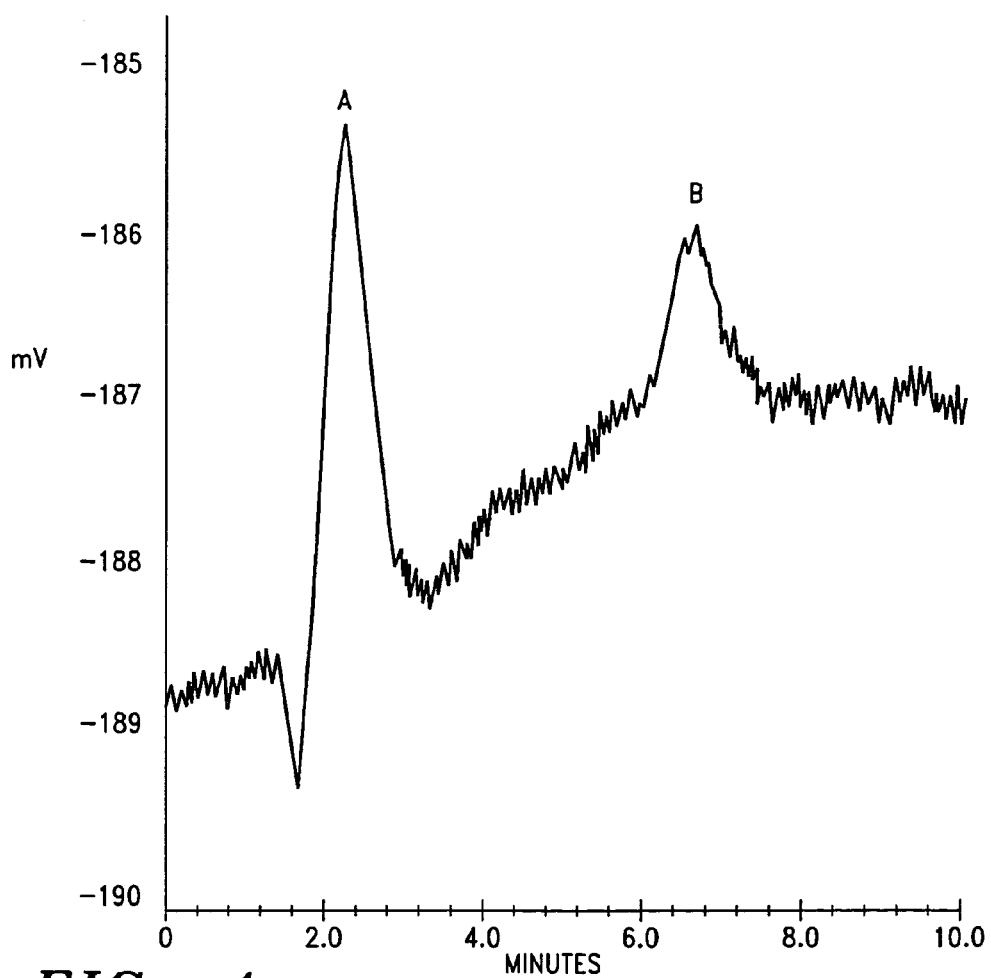
FIG. 4 illustrates an elution profile using a monolithic column after injection of a mixture containing a 20-mer polynucleotide and a double-stranded DNA standard.

The injection volume was 0.36 µL (split from 60 µL). The pressure was 2450 psi. The temperature of the mixing tee was 47° C. The detection was by UV at 254 nm. FIG. 4 was obtained after injection of a mixture containing the 20-mer (12 µM) (Operon Technologies) and a Bio-Rad DNA standard (double-stranded DNA ruler, catalog no. 170-8203). The concentration of the sd DNA in the injected mixture was 4 nM based on a 5000 bp average length. Peak A corresponds to the 20-mer polynucleotide and peak B corresponds to the dsDNA standard. Under these conditions the 20-mer polynucleotide eluted at 2.3 minutes and the dsDNA standard eluted as a broad undifferentiated peak at 6.8 minutes.

EXAMPLE 14

Preparation of a Standard Bore Monolithic Separation Column

A 4.6 mm ID×50.0 mm length stainless steel column was packed with macro porous resin beads (27% polystyrene cross-linked with divinylbenzene; catalogue no. POL-99-0319, Transgenomic) in methanol (Omnisolve for HPLC, EM Science) at 3000 psi for 20 min. The stainless steel column jacket, end fitting assembly, and titanium frits were obtained from Isolation Technologies, Inc., (Hopedale, Mass.). Ten mL of a monomer mixture, as described below, was pumped through the column at a rate of 0.2 mL/min. The column was sealed with end-plugs and heated at 90° C. for 18 h.

The monomer mixture comprised the following components: 2000 µL divinylbenzene (80%) (Sigma-Aldrich, St. Louis, Mo.); 3000 µL styrene (98%), (Sigma-Aldrich); 6500 µL 1-decanol (99%), (Alfa Aesar, Ward Hill. MA); 1000 µL tetrahydrofuran (99%), (Omnisolve for HPLC, EM Science); and 120 mg 2,2' azobisisobutyronitrile (Alfa Aesar).

In order to remove unreacted monomers, oligomers and the porogen the capillaries were flushed for 12 h with tetrahydrofuran (Omnisolve, EM Science) and methanol (Anhydrous, EM Science). The pumps were set to constant pressure at 4000 psi. The flow rate was 100–250 µL/min at 90° C.

EXAMPLE 15

Separation of DNA Using a Polystyrene/Divinylbenxene Monolithic Capillary Column The column described in Example 14 was used to elute a double-stranded DNA standard. The sample contained a 209 bp standard (concentration 0.0025 µg DNA/µL, catalogue no. 560077, Transgenomic). The injection volume was 30 µL. The mobile phase (pH 7) included eluent A: 100 mM TEAA in water; and eluent B: 100 mM TEAA with 25% acetonitrile. The following gradient was used:

| Time (min) | % B |
|---|---|
| 0 | 30 |
| 3 | 70 |
| 45 | 90 |
| 46 | 30 |

Figure 5:
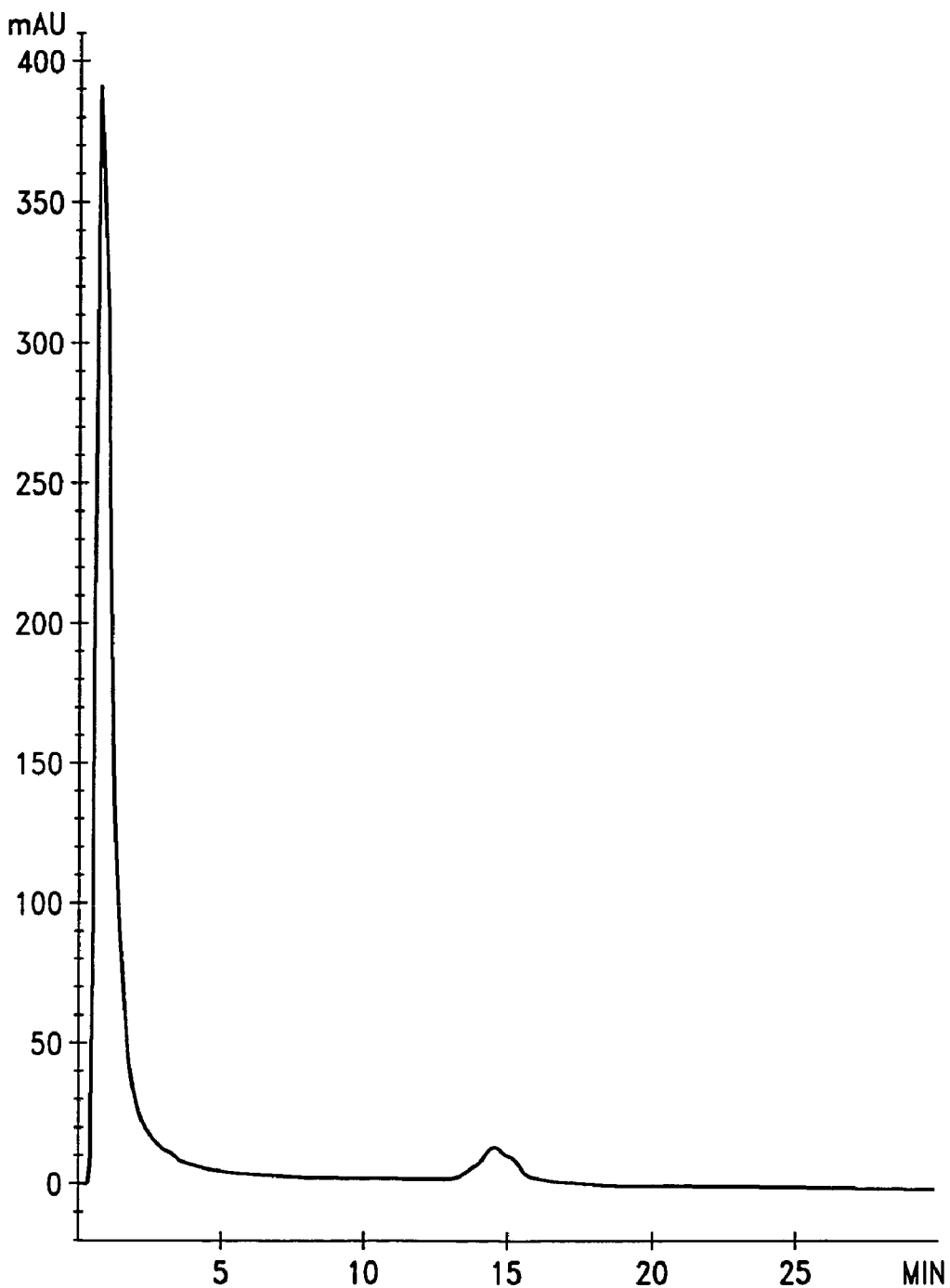
FIG. 5 illustrates an elution profile using a monolithic column after injection of a 209 base pair double-stranded DNA fragment.

The flow rate was 0.2 mL/min and the detection was by UV at 254 nm. A single peak at 14.4 min was observed (FIG. 5).

EXAMPLE 16

Effect of Cr(III) Contamination on Sample Resolution by MIPC at 50° C.

A 20-mer polynucleotide having the following sequence (obtained from Operon Technologies Inc., Alameda, Calif.) was analyzed:

5'-TAGGTTTTATTATTATATTT-3' (SEQ ID NO: 2)

Figure 6:
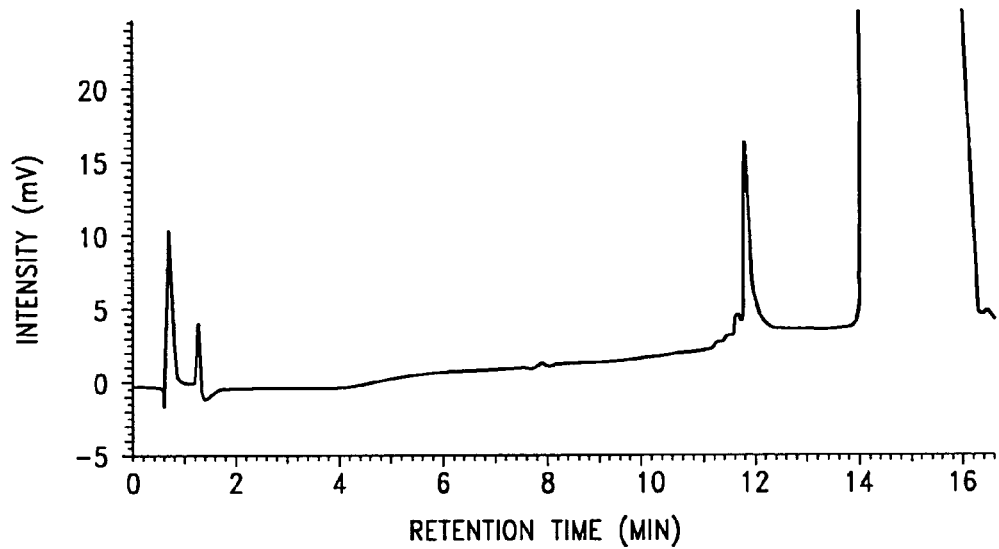
FIG. 6 illustrates an elution profile from a MIPC analysis of a single-stranded polynucleotide carried out at a column temperature of 50° C.

The separation shown in FIG. 6 was obtained using a 50×4.6 mm ID column containing 2.2 µm alkylated poly (styrene-divinylbenzene) beads (DNASep®, Transgenomic, Inc.). The chromatography system included a Waters Action Analyzer LC System, a Model 484 Tunable Absorbance Detector (Waters), a Model L7200 autosampler (Hitachi), a model L7300 oven (Hitachi), and the HSM Chromatography Data System (Hitachi). The mobile phase included buffer A: 0.1 M TEAA (2 M concentrate available from Transgenomic, Inc.) (Eluent A), pH 7.3; buffer B: 0.1 M TEM and 25.0% acetonitrile; buffer C: 70% acetonitrile in water.

The gradient was as follows: 10% B for 1 minute, then a linear gradient from 10% B to 46% B in 12 minutes, followed by 100% C for 2 minutes. The flow rate was 0.75 mL/min.; UV detection was at 260 nm; and the column oven setting was 50° C.

The polynucleotide was suspended to a concentration of 100 pmol/microliter in TE8 buffer (containing Tris 10 mM/L, EDTA 1 mM/L, pH 8.0, Catalogue no. 0224, Teknova, Half Moon Bay, Calif.), and one part of the suspension was diluted with four parts of water prior to injection. The injection volume was 3 µL (=75 pmol DNA). The polynucleotide eluted at a retention time of about 12 min.

Figure 7:
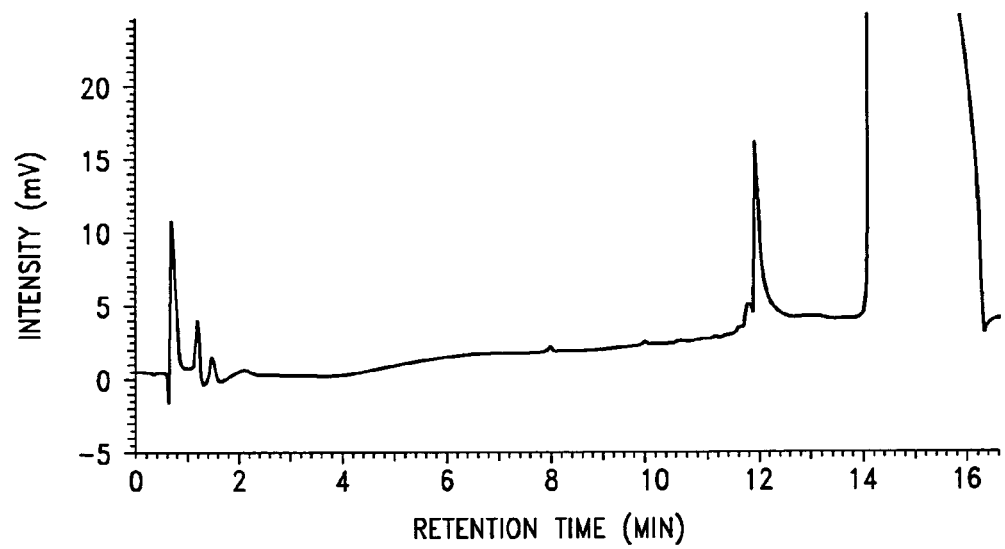
FIG. 7 illustrates an elution profile from a MIPC analysis of a single-stranded polynucleotide carried out at a column temperature of 50° C. after a single injection of a Cr(III) solution onto the column used in FIG. 6.

The column was injected with 5 µL of 520 ppm Cr(III) solution and subjected to the same gradient. The Cr(III) solution was prepared by dissolving 0.125 g of $CrK(SO_4)_2.12H_2O$ (Mallinckrodt Baker, Inc.) in 25 mL deionized water. This was followed by another 3 µL injection of polynucleotide which gave the elution profile shown in FIG. 7. The integrated area under the peak at 12 min in FIG. 7 was 89% as compared with the peak in FIG. 6.

Figure 8:
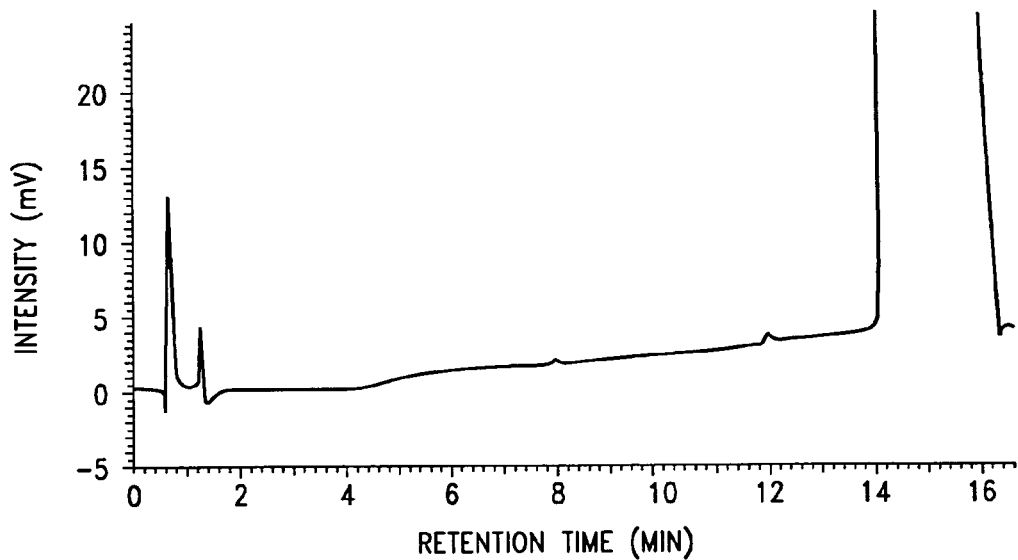
FIG. 8 illustrates an elution profile from a MIPC analysis of a single-stranded polynucleotide carried out at a column temperature of 50° C. after five additional injections of a Cr(III) solution onto the column used in FIG. 7.

The column was then injected with five more 5 µL portions of the 520 ppm Cr(III) solution. Each of these was a continuous injection lasting about 0.8 min. The time between injections was 1.8 min. Before and after each injection, a constant mobile phase containing 10% B was passed through the column. After the last injection of Cr(III), a baseline in the UV absorbance was obtained, and another 3 µL of polynucleotide was injected giving the elution profile shown in FIG. 8, in which essentially no detectable peak due to the polynucleotide could be observed.

Figure 9:
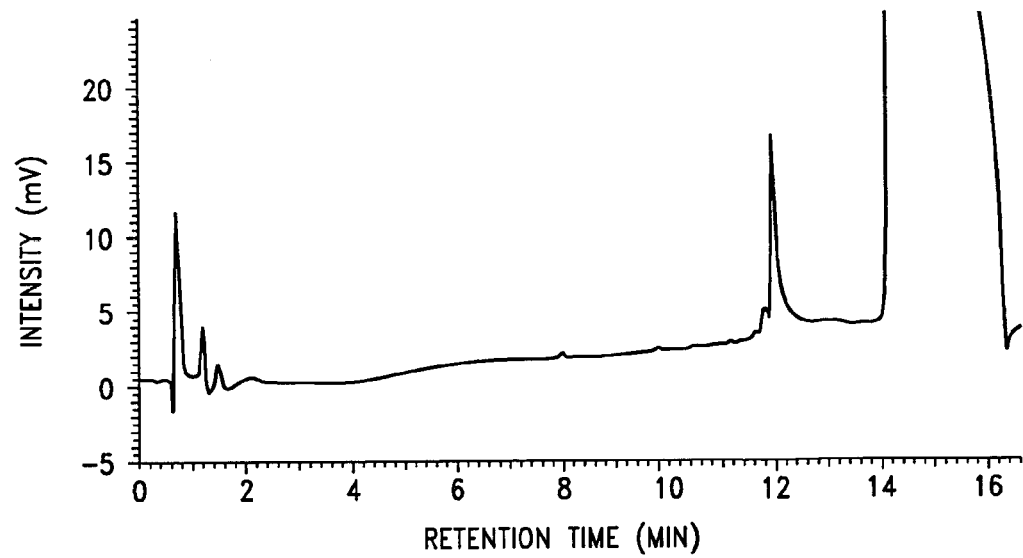
FIG. 9 illustrates an elution profile from a MIPC analysis of a single-stranded polynucleotide carried out at a column temperature of 50° C. after one injection of an EDTA solution onto the column used in FIG. 8.

The column was then injected with 10 µL of a 0.1M solution of EDTA followed by gradient elution. The EDTA solution was prepared by dissolving 1.1306 g of $Na_4EDTA.4H_2O$ (Fluka) in 25 mL water. This was followed by another 3 µL injection of polynucleotide which gave the elution profile shown in FIG. 9. The area under the peak at 12 min in FIG. 9 was 97% as compared with the peak in FIG. 6.

Figure 10:
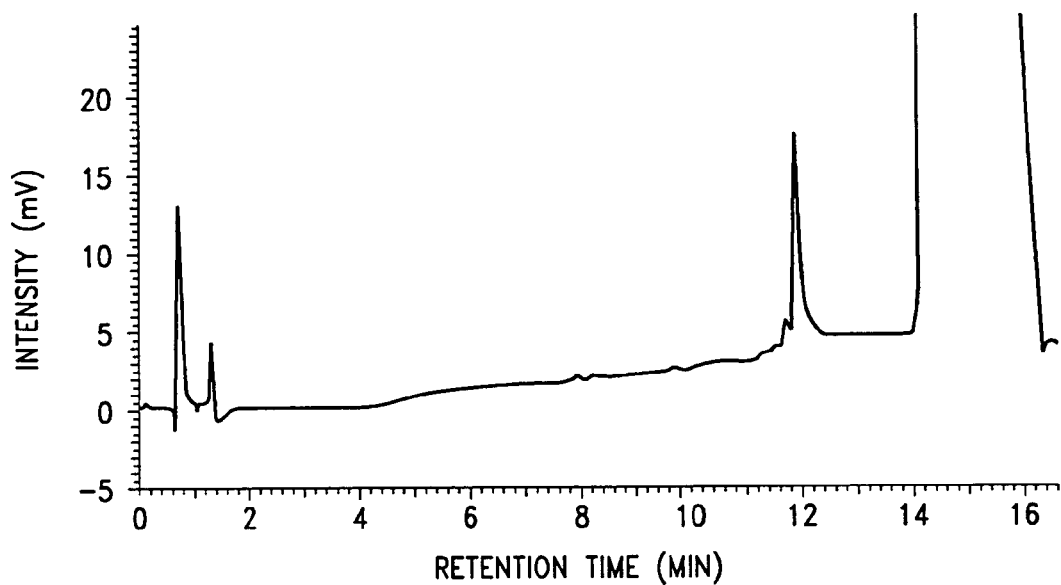
FIG. 10 illustrates an elution profile from a MIPC analysis of a single-stranded polynucleotide carried out at a column temperature of 50° C. after five additional injections of an EDTA solution onto the column used in FIG. 9.

The column was then injected with five more 10 µL portions of the 0.1M EDTA solution. Each of these was a continuous injection (at a constant flow of 10% B) lasting about 0.8 min. After a constant baseline in the UV absorbance was obtained, another 3 µL of polynucleotide was injected which gave the elution profile shown in FIG. 10. The area under the peak at 12 min in FIG. 10 was 100% as compared with the peak in FIG. 6.

EXAMPLE 17

Effect of Cr(III) Contamination On Sample Recovery by MIPC at 75° C.

Figure 11:
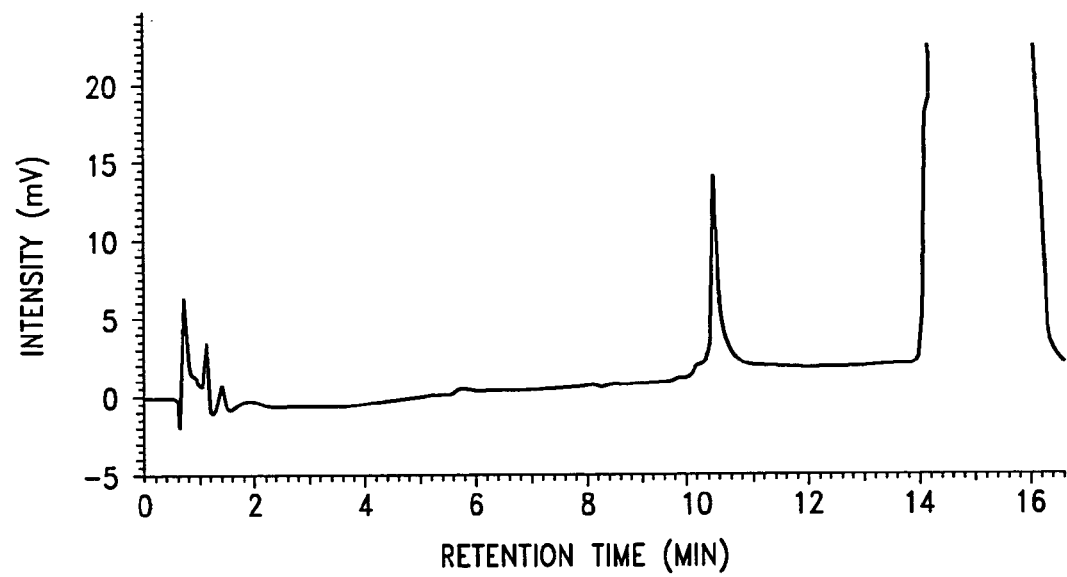
FIG. 11 illustrates an elution profile from a MIPC analysis of a single-stranded polynucleotide carried out at a column temperature of 75° C.

The 20-mer polynucleotide prepared as described in Example 16 was injected and eluted using the conditions described in Example 16 but at a column oven temperature of 75° C. The polynucleotide eluted in a single peak at 10.4 min (FIG. 11).

Figure 12:
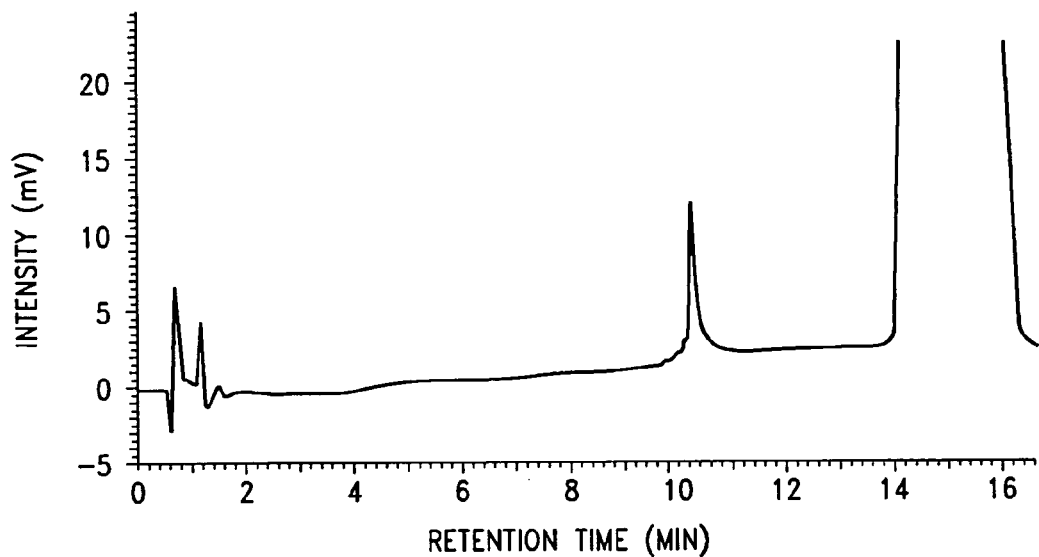
FIG. 12 illustrates an elution profile from a MIPC analysis of a single-stranded polynucleotide carried out at a column temperature of 75° C. after a single injection of a Cr(III) solution onto the column used in FIG. 11.

The column was injected with 5 μL of 520 ppm Cr(III) solution and subjected to the same gradient. This was followed by another 3 μL injection of polynucleotide which gave the elution profile shown in FIG. 12. The area under the peak at 10.4 min in FIG. 12 was 85% as compared with the peak in FIG. 11.

Figure 13:
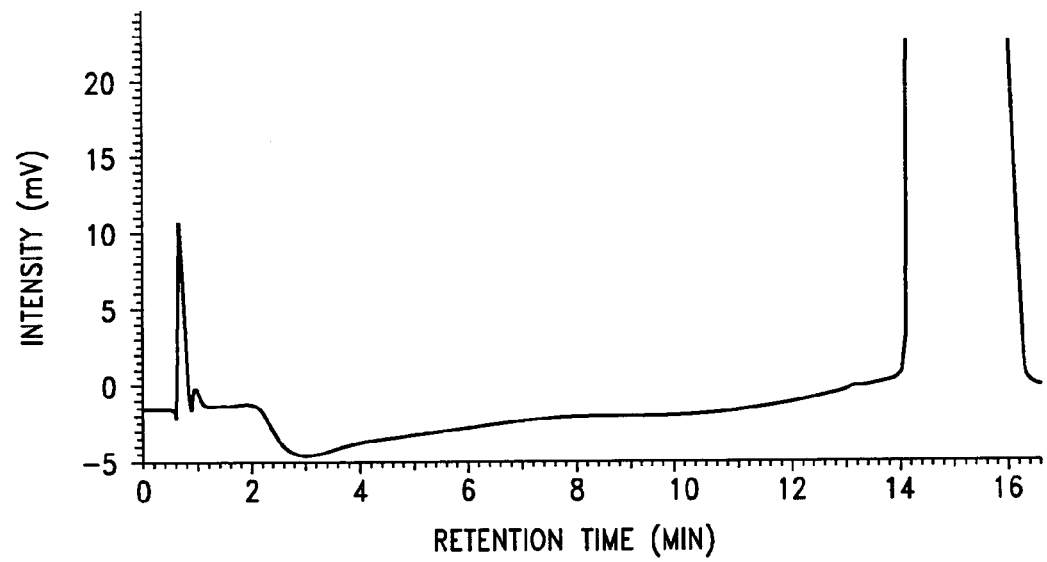
FIG. 13 illustrates an elution profile from a MIPC analysis of a single-stranded polynucleotide carried out at a column temperature of 75° C. after five additional injections of a Cr(III) solution onto the column used in FIG. 12.

The column was then injected with five more 5 μL portions of the 520 ppm Cr(III) solution as described above. This was followed by another 3 μL injection of polynucleotide which gave the elution profile shown in FIG. 13. No peak attributable to the elution of the polynucleotide could be detected.

Figure 14:
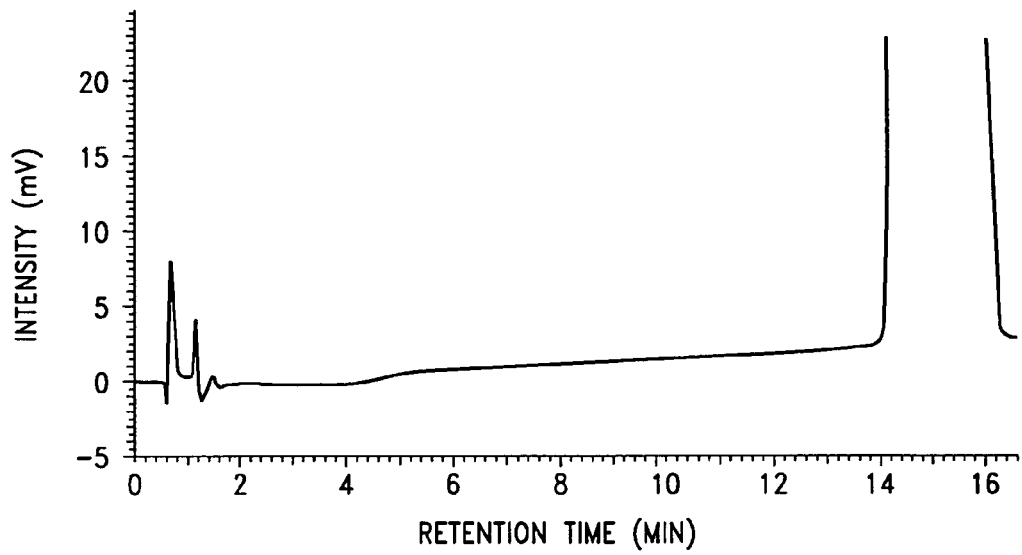
FIG. 14 illustrates an elution profile from a MIPC analysis of a single-stranded polynucleotide carried out at a column temperature of 75° C. after one injection of an EDTA solution onto the column used in FIG. 13.

The column was then injected with 10 μL of a 0.1M solution of EDTA. This was followed by another 3 μL injection of polynucleotide which gave the elution profile shown in FIG. 14. No peak attributable to the elution of the polynucleotide was observed.

Figure 15:
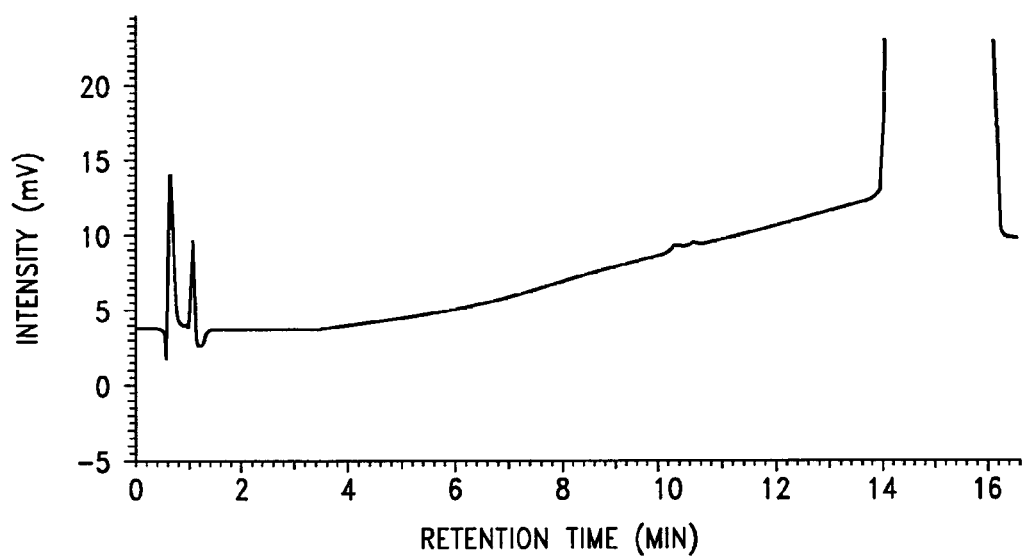
FIG. 15 illustrates an elution profile from a MIPC analysis of a single-stranded polynucleotide carried out at a column temperature of 75° C. after five additional injections of an EDTA solution onto the column used in FIG. 14.

The column was then injected with five more 10 μL portions of the 0.1M EDTA solution as described above. This was followed by another 3 μL injection of polynucleotide which gave the elution profile shown in FIG. 15 in which no peak attributable to the elution of the polynucleotide was observed.

Thus, the effect of contamination with Cr(III) was more pronounced when the elution was performed at a higher temperature.

EXAMPLE 18

Effect of Cu(II) Contamination on Sample Recovery by MIPC at 50° C.

A 20-mer polynucleotide having the following sequence (obtained from Operon Technologies Inc., Alameda, Calif.) was analyzed:

5'-TAGGTTTTATTATTATATTT-3' (SEQ ID NO: 2)

Figure 16:
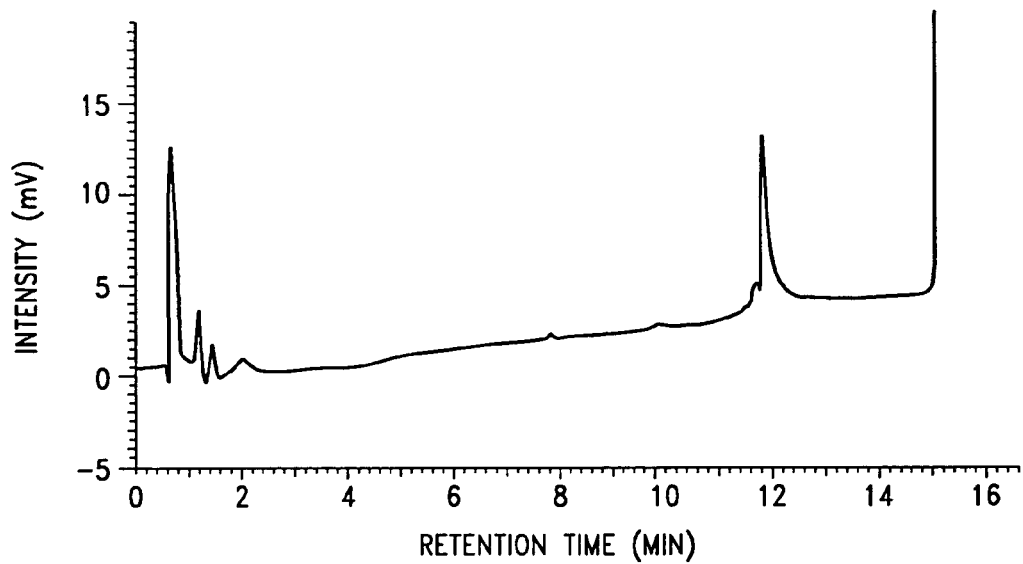
FIG. 16 illustrates an elution profile from a MIPC analysis of a single-stranded polynucleotide carried out at a column temperature of 50° C.

The initial separation (FIG. 16) was obtained using a 50×4.6 mm ID column containing 2.2 μm alkylated poly (styrene-divinylbenzene) beads (DNASep®, Transgenomic, Inc.). The chromatography system included a Waters Action Analyzer LC System, a Model 484 Tunable Absorbance Detector (Waters), a Modle L7200 autosampler (Hitachi), a model L7300 oven (Hitachi), and the HSM Chromatography Data System (Hitachi). The mobile phase included buffer A: 0.1 M TEAA (2 M concentrate available from Transgenomic, Inc.) (Eluent A), pH 7.3; buffer B: 0.1 M TEAA and 25.0% acetonitrile; buffer C: 70% acetonitrile in water.

The gradient was as follows: 10% B for 1 minute, then a linear gradient from 10% B to 46% B in 12 minutes, followed by 100% C for 2 minutes. The flow rate was 0.75 mL/min.; UV detection was at 260 nm; and the column oven setting was 50° C.

The polynucleotide was suspended to a concentration of 100 pmol/microliter in TE8 buffer (containing Tris 10 mM/L, EDTA 1 mM/L, pH 8.0, Catalogue no. 0224, Teknova, Half Moon Bay, Calif.), and was diluted 1:4 in water prior to injection. The injection volume was 3 μL (=75 pmol DNA). The polynucleotide eluted at a retention time of about 12 min.

Figure 17:
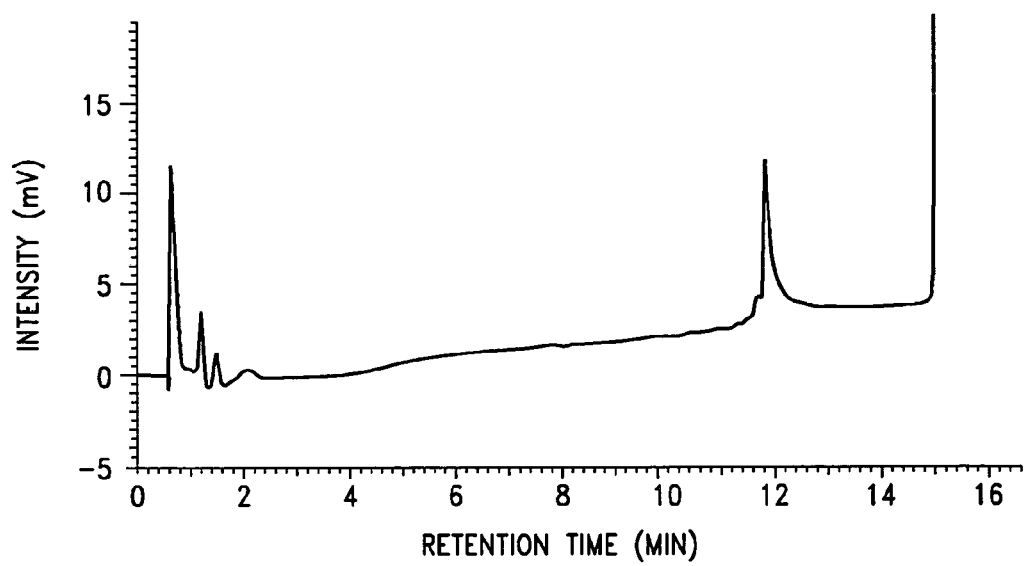
FIG. 17 illustrates an elution profile from a MIPC analysis of a single-stranded polynucleotide carried out at a column temperature of 50° C. after a single injection of a Cu(II) solution onto the column used in FIG. 16.

The column was injected with 10 μL of 100 ppm Cu(II) solution and subjected to the same gradient. The Cu(II) solution was prepared by dissolving 0.0982 g of $CuSO_4.5H_2O$ (J. T. Baker, Phillipsburg, N.J.) in 25 mL deionized water. This was followed by another 3 μL injection of polynucleotide which gave the elution profile shown in FIG. 17. The integrated area under the peak at 12 min in FIG. 17 was 90.70% as compared with the peak in FIG. 16.

Figure 18:
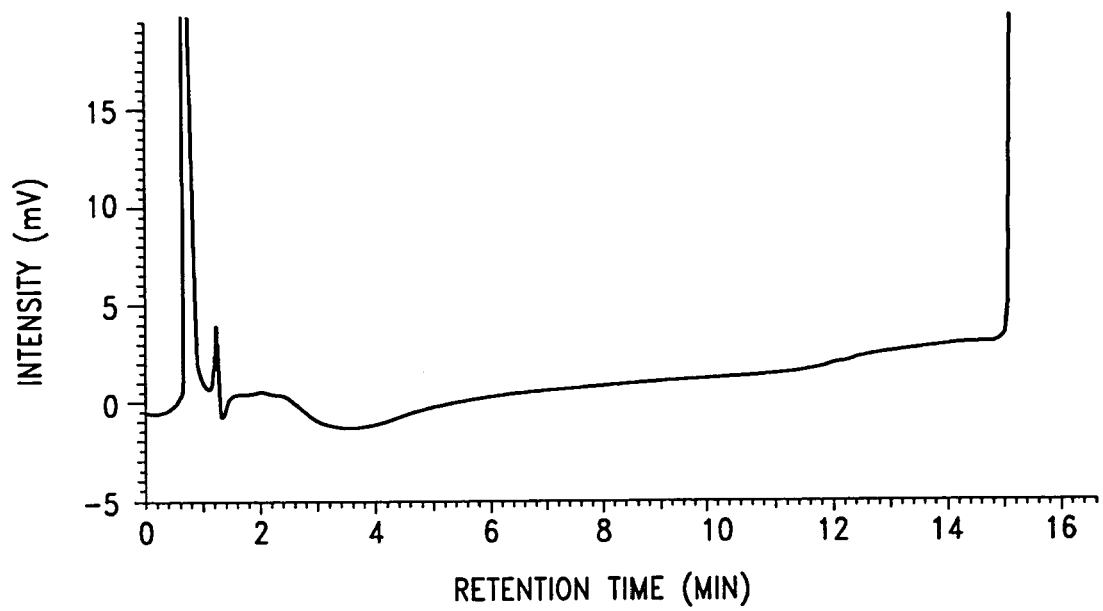
FIG. 18 illustrates an elution profile from a MIPC analysis of a single-stranded polynucleotide carried out at a column temperature of 50° C. after five additional injections of a Cu(II) solution onto the column used in FIG. 17.

The column was then injected with five more 5 μL portions of the 100 ppm Cu(II) solution. Each of these was a continuous injection lasting about 0.8 min. The time between injections was 1.8 min. Before and after each injection, a constant mobile phase containing 10% B was passed through the column. After the last injection of C(II), a baseline in the UV absorbance was obtained, and another 3 μL of polynucleotide was injected giving the elution profile shown in FIG. 18, in which essentially no detectable peak due to the polynucleotide could be observed.

Figure 19:
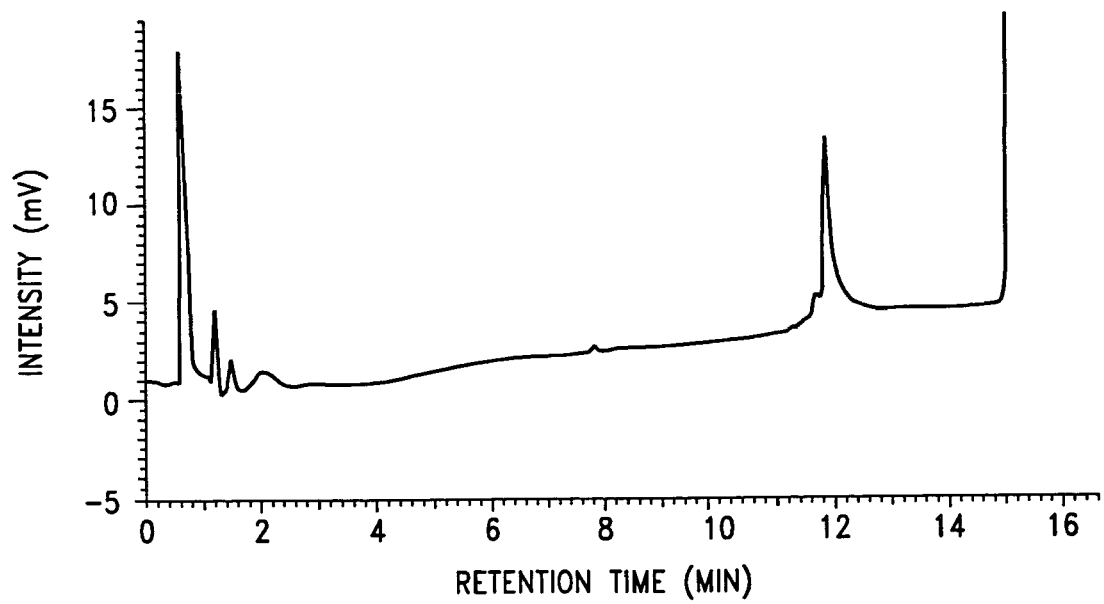
FIG. 19 illustrates an elution profile from a MIPC analysis of a single-stranded polynucleotide carried out at a column temperature of 50° C. after one injection of an EDTA solution onto the column used in FIG. 18.

The column was then injected with 10 μL of a 0.1M solution of EDTA followed by gradient elution. This was followed by another 3 μL injection of polynucleotide which gave the elution profile shown in FIG. 19. The area under the peak at 12 min in FIG. 19 was 102.6% as compared with the peak in FIG. 16.

Figure 20:
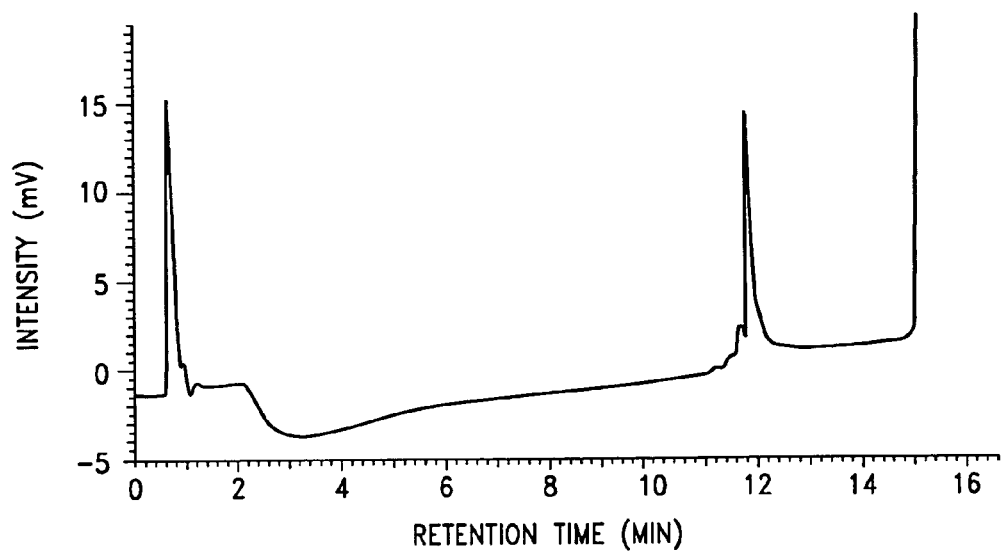
FIG. 20 illustrates an elution profile from a MIPC analysis of a single-stranded polynucleotide carried out at a column temperature of 50° C. after five additional injections of an EDTA solution onto the column used in FIG. 19.

The column was then injected with five more 10 μL portions of the 0.1M EDTA solution. Each of these was a continuous injection (at a constant flow of 10% B) lasting about 0.8 min. After a constant baseline in the UV absorbance was obtained, another 3 μL of polynucleotide was injected which gave the elution profile shown in FIG. 20. The area under the peak at 12 min in FIG. 20 was 112% as compared with the peak in FIG. 16.

EXAMPLE 19

Effect of Cu(II) Contamination on Sample Recovery by MIPC at 750° C.

Figure 21:
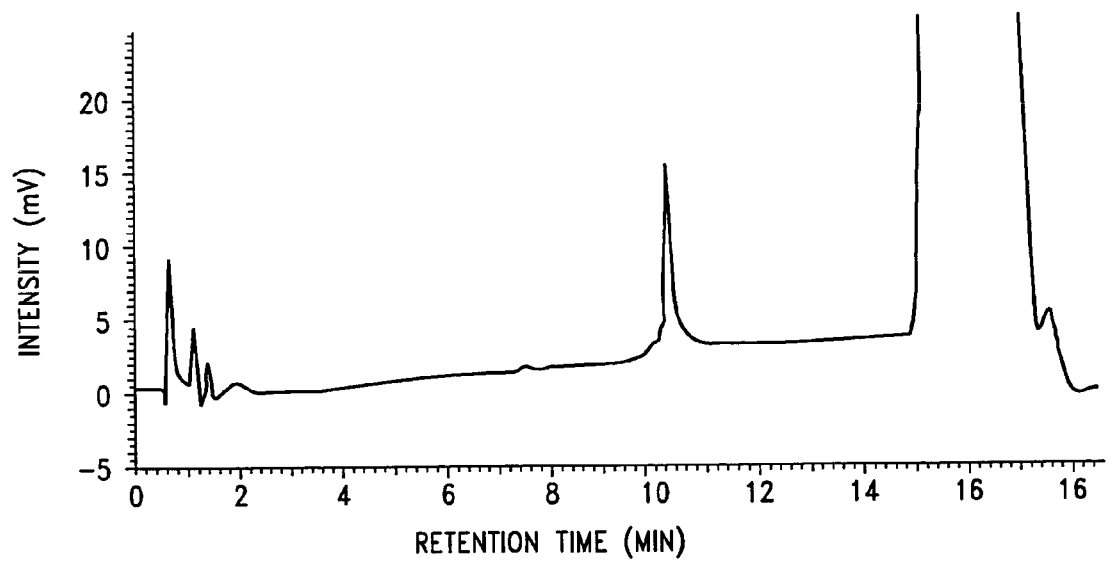
FIG. 21 illustrates an elution profile from a MIPC analysis of a single-stranded polynucleotide carried out at a column temperature of 75° C.

The 20-mer polynucleotide prepared as described in Example 18 was injected and eluted using the conditions described in Example 18 but at a column oven temperature of 75° C. The polynucleotide eluted in a single peak at 10.3 min (FIG. 21).

Figure 22:
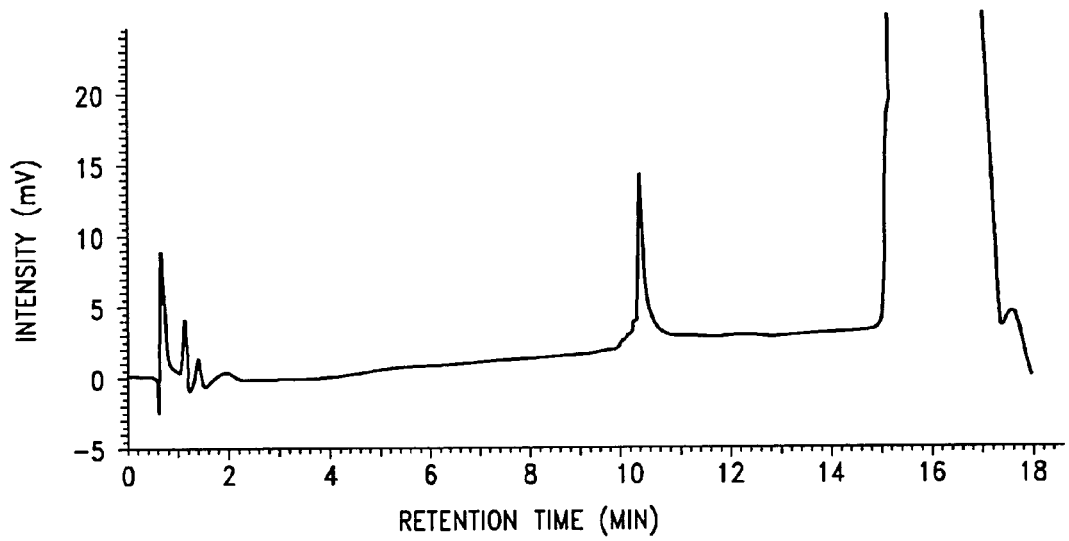
FIG. 22 illustrates an elution profile from a MIPC analysis of a single-stranded polynucleotide carried out at a column temperature of 75° C. after a single injection of a Cu(II) solution onto the column used in FIG. 21.

The column was injected with 10 μL of 100 ppm Cu(II) solution and subjected to the same gradient. This was followed by another 3 μL injection of polynucleotide which gave the elution profile shown in FIG. 22. The area under the peak at 10.3 min in FIG. 22 was 94.42% as compared with the peak in FIG. 21.

Figure 23:
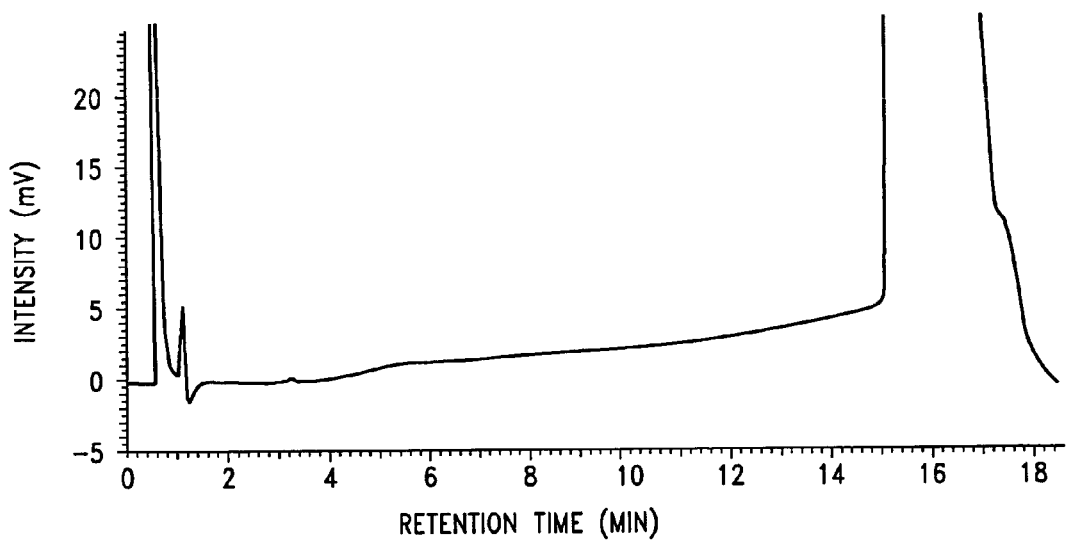
FIG. 23 illustrates an elution profile from a MIPC analysis of a single-stranded polynucleotide carried out at a column temperature of 75° C. after five additional injections of a Cu(II) solution onto the column used in FIG. 22.

The column was then injected with five more 5 μL portions of the 100 ppm Cu(II) solution as described above. This was followed by another 3 μL injection of polynucleotide which gave the elution profile shown in FIG. 23. No peak attributable to the elution of the polynucleotide could be detected.

Figure 24:
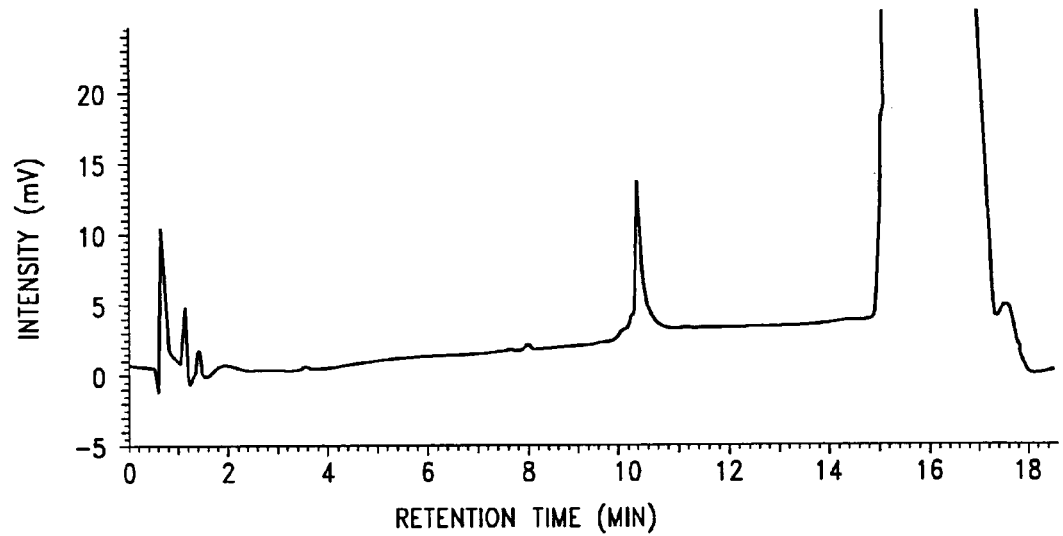
FIG. 24 illustrates an elution profile from a MIPC analysis of a single-stranded polynucleotide carried out at a column temperature of 75° C. after one injection of an EDTA solution onto the column used in FIG. 23.

The column was then injected with 10 μL of a 0.1M solution of EDTA followed by gradient elution. This was followed by another 3 μL injection of polynucleotide which gave the elution profile shown in FIG. 24. The area under the peak at 10.30 min in FIG. 24 was 86.32% as compared with the peak in FIG. 21.

Figure 25:
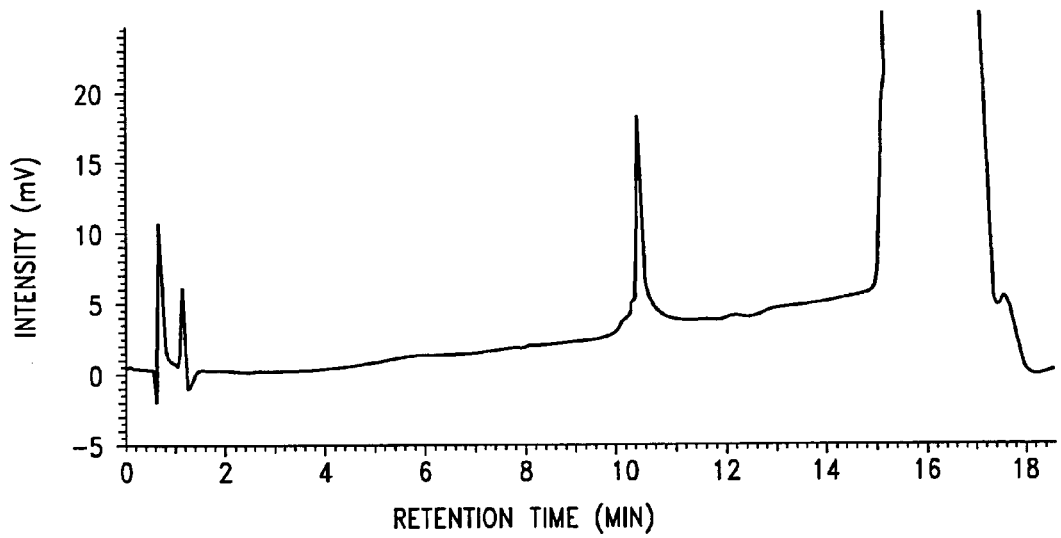
FIG. 25 illustrates an elution profile from a MIPC analysis of a single-stranded polynucleotide carried out at a column temperature of 75° C. after five additional injections of an EDTA solution onto the column used in FIG. 24.

The column was then injected with five more 10 μL portions of the 0.1M EDTA solution. Each of these was a continuous injection (at a constant flow of 10% B) lasting about 0.8 min. After a constant baseline in the UV absorbance was obtained, another 3 μL of polynucleotide was injected which gave the elution profile shown in FIG. 25. The area under the peak at 10.30 min in FIG. 25 was 110.25% as compared with the peak in FIG. 21.

Thus, at 75° C., the column could not be as easily regenerated, by EDTA treatment, as at 50° C.

EXAMPLE 20

MIPC Analysis of an RNA Sizing Standard by MIPC Using a 7.8 mm ID Column

Figure 26:
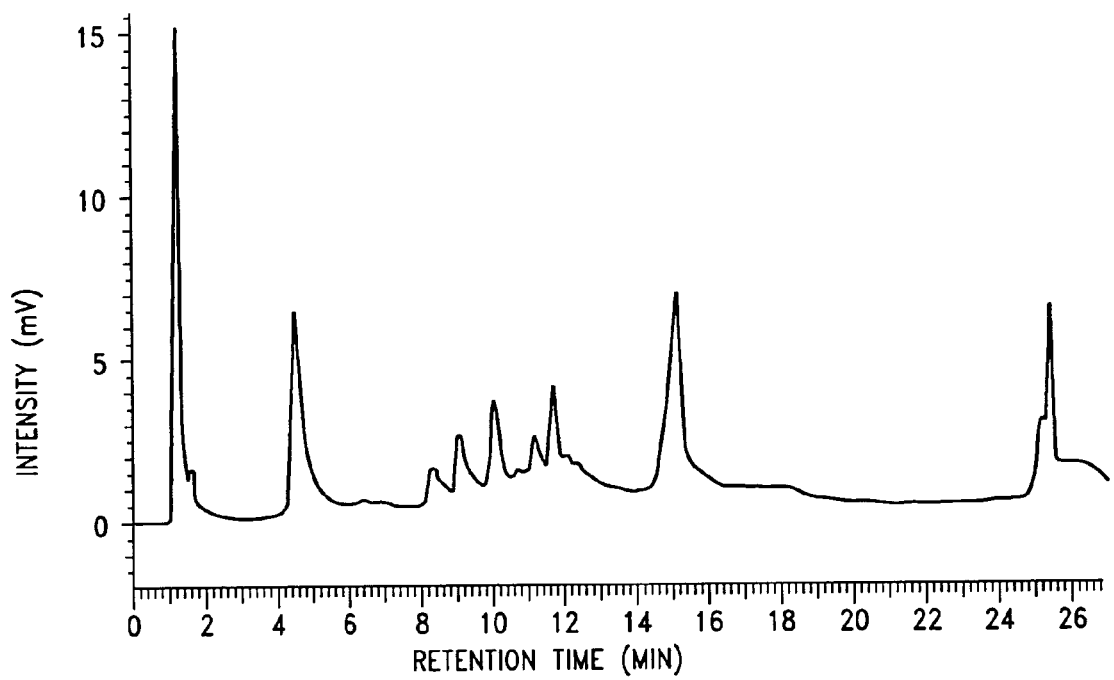
FIG. 26 illustrates an elution profile from MIPC analysis of RNA size markers carried out at a column temperature of 40° C.
Figure 27:
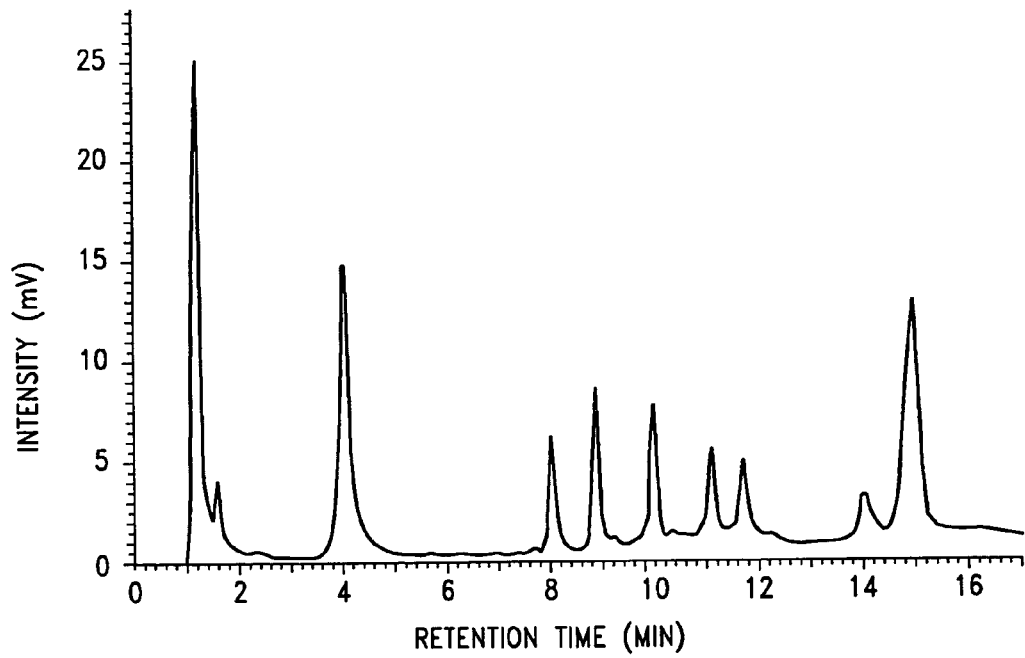
FIG. 27 illustrates an elution profile from MIPC analysis of RNA size markers carried out at a column temperature of 50° C.
Figure 28:
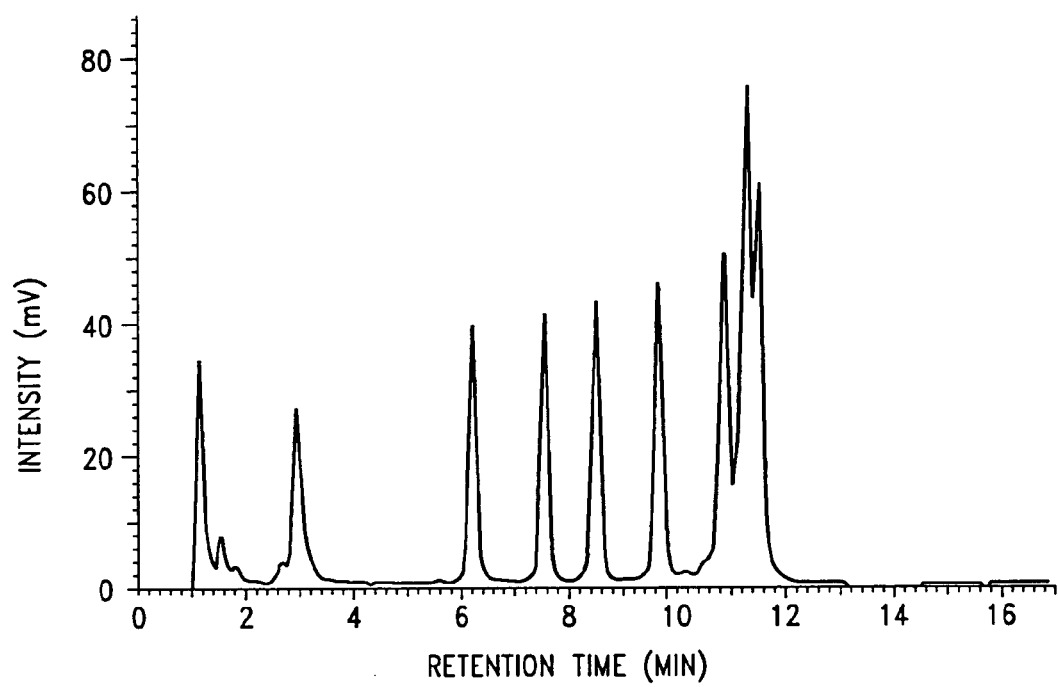
FIG. 28 illustrates an elution profile from MIPC analysis of RNA size markers carried out at a column temperature of 65° C.

MIPC analysis of an RNA ladder (Catalog no. 15623010, Life Technologies, containing single-stranded fragments of the following nucleotide lengths: 155, 280, 400, 530, 780, 1280,1520, 1770) was performed using octadecyl modified, nonporous poly(styrene-divinylbenzene) beads packed in a 50 mm×7.8 mm ID reverse phase column (DNASEP® cartridge, Transgenomic, Inc., San Jose, Calif.) and using a WAVE® Nucleic Acid Fragment Analysis System (Transgenomic) (FIG. 26). Buffer A: 0.1 M TEAA, pH 7.0; buffer B: 0.1 TEAA, 25% (v/v) acetonitrile, pH 7.0. The buffer stock solutions were obtained form Transgenomic. The gradient conditions were as follows:

| Time (min) | % B |
|---|---|
| 0.0 | 38 |
| 1.0 | 40 |
| 16 | 60 |
| 22 | 66 |
| 22.5 | 70 |
| 23 | 100 |
| 24 | 100 |
| 25 | 38 |
| 27 | 38 |

The flow rate was 0.9 mL/min and the column temperature was 40.0° C. UV detection was performed at 260 nm. The injection volume was 3.0 µL (3 µg RNA). The sample contained a mixture of eight RNAs having the nucleotide lengths as shown in FIG. 26.

Prior to the injection and elution of the RNA sample, the column was equilibrated with 75% acetonitrile for 30–45 min at a flow rate of 0.9 mL/min. The column was then equilibrated using 38% B for 30 min. Prior to the injection and elution of RNA, two control gradient elutions (using the same gradient conditions as for the RNA) were performed after a first injection consisting of 10 µL of 0.5 mM EDTA and after a second injection consisting of 10 µL of nuclease free water (Catalog no. 9930, Ambion, Inc., Austin, Tex.). These two injections (data not shown) demonstrated that the column was free from contamination.

In preparing the RNA sample for injection, all chemicals were of the highest purity grade available for molecular biology. Solutions, glassware, and small instruments were sterilized whenever possible. Liquid transfers were made using RNase free pipette tips (Rainin Instrument Co., Inc., Woburn, Mass.). All manipulations were performed wearing surgical gloves.

EXAMPLE 21

Effect of Temperature on the Elution of RNA Sizing Standards

Figure 29:
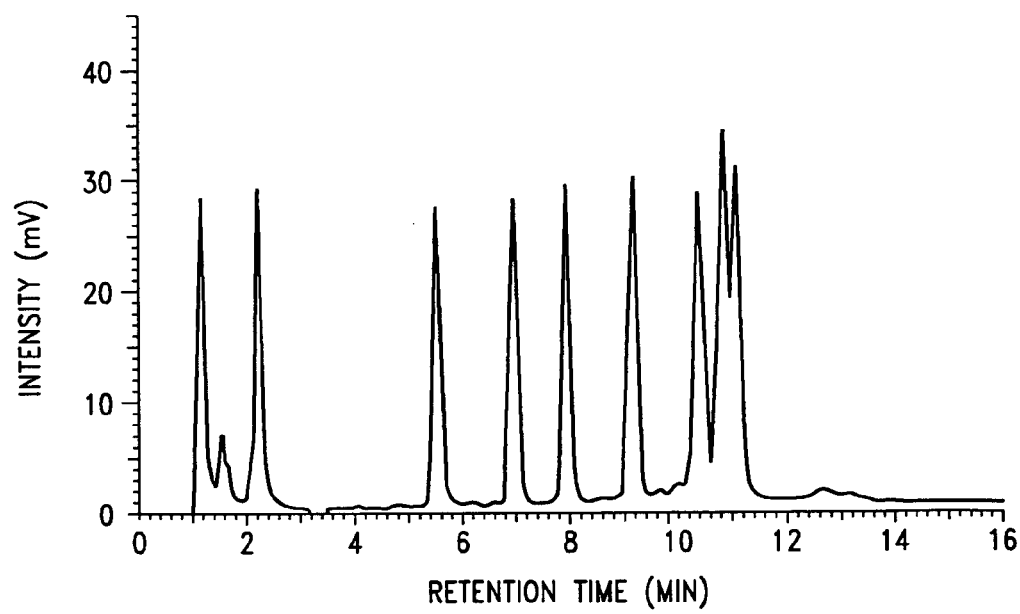
FIG. 29 illustrates an elution profile from MIPC analysis of RNA size markers carried out at a column temperature of 75° C.

The MIPC analysis as described in Example 20 was repeated at column temperatures of 50.0° C. (FIG. 27), 65° C. (FIG. 28), and 75° C. (FIG. 29).

EXAMPLE 22

Effect of Cr(III) Contamination on Sample Recovery of a Tagged Polynucleotide by MIPC at 50° C.

A fluorescently labeled 20-mer polynucleotide having the following nucleotide sequence was analyzed:

5'-AGGCACTGGTCAGAATGAAG-3' (SEQ ID NO: 3)

The polynucleotide (obtained from Operon Technologies) included a 5-carboxy-fluorescein label (6-FAM) covalently attached at the 5' end. A 50 µM stock solution was prepared by suspending the lyophylized polynucleotide preparation in TE buffer (Catalog no. EM-8890, EM Science).

The separation was performed using a 50×4.6 mm ID column containing 2.2 µm alkylated poly(styrene-divinylbenzene) beads (DNASep®, Transgenomic, Inc.). The chromatography system included a Waters Action Analyzer LC System, a Model 484 Tunable Absorbance Detector (Waters), a Model L7200 autosampler (Hitachi), a model L7300 oven (Hitachi), and the HSM Chromatography Data System (Hitachi). The mobile phase included buffer A: 0.1 M TEAA (2 M concentrate available from Transgenomic, catalog no. 553303), pH 7.3; buffer B: 0.1 M TEM and 25.0% acetonitrile; buffer C: 70% acetonitrile in water.

The gradient was as follows: linear gradient from 25% to 30% B in 1 minute, then a linear gradient to 65% B in 7 minutes, followed by 100% C for 1 min. The flow rate was 0.75 mL/min.; UV detection was at 260 nm; and the column oven setting was 50° C.

The stock solution of labeled polynucleotide was diluted 1:20 in TE buffer (one volume of stock solution plus 19 volumes of TE buffer) prior to injection. The injection volume was 15 µL. The labeled polynucleotide eluted in an initial elution with a retention time of about 4.6 min (data not shown).

The column was injected with 5 µL of 520 ppm Cr(III) solution and subjected to the same gradient. This was followed by another 15 µL injection of polynucleotide which gave a second elution profile (not shown). The integrated area under the peak at 4.6 min was 44% as compared with the peak in the first elution profile.

The column was then injected with five more 5 µL portions of the 520 ppm Cr(III) solution. Each of these was a continuous injection lasting about 0.8 min. The time between injections was 1.8 min. Before and after each injection, a constant mobile phase containing 10% B was passed through the column. After the last injection of Cr(III), a baseline in the UV absorbance was obtained, and another 15 µL of polynucleotide was injected in a third elution in which no detectable peak due to the labeled polynucleotide could be observed (data not shown).

The column was then injected with 10 µL of a 0.1M solution of EDTA followed by gradient elution. This was followed by another 15 µL injection of polynucleotide which gave a fourth in which no detectable peak due to the labeled polynucleotide could be observed (data not shown).

The column was then injected with five more 10 μL portions of the 0.1M EDTA solution. Each of these was a continuous injection (at a constant flow of 10% B) lasting about 0.8 min. After a constant baseline in the UV absorbance was obtained, another 15 μL of polynucleotide was injected which gave a fifth elution profile in which no detectable peak due to the labeled polynucleotide was observed (data not shown).

EXAMPLE 23

Effect of Cr(III) Contamination on Sample Recovery of a Tagged Polynucleotide by MIPC at 75° C.

The labeled 20-mer polynucleotide prepared as described in Example 22 was injected and eluted using the conditions described in Example 22 but at a column oven temperature of 75° C. The polynucleotide eluted in a first elution profile in a single peak at 3.8 min (not shown).

The column was injected with 5 μL of 520 ppm Cr(III) solution and subjected to the same gradient. This was followed by another 15 μL injection of polynucleotide which gave a second elution profile (not shown). The integrated area under the peak at 4.6 min was 40% as compared with the peak in the first elution profile.

The column was then injected with five more 5 μL portions of the 520 ppm Cr(III) solution. Each of these was a continuous injection lasting about 0.8 min. The time between injections was 1.8 min. Before and after each injection, a constant mobile phase containing 10% B was passed through the column. After the last injection of Cr(III), a baseline in the UV absorbance was obtained, and another 15 μL of polynucleotide was injected in a third elution in which no detectable peak due to the labeled polynucleotide could be observed (data not shown).

The column was then injected with 10 μL of a 0.1M solution of EDTA followed by gradient elution. This was followed by another 15 μL injection of polynucleotide which gave a fourth in which no detectable peak due to the labeled polynucleotide could be observed (data not shown).

The column was then injected with five more 10 μL portions of the 0.1M EDTA solution. Each of these was a continuous injection (at a constant flow of 10% B) lasting about 0.8 min. After a constant baseline in the UV absorbance was obtained, another 15 μL of polynucleotide was injected which gave a fifth elution profile in which no detectable peak due to the labeled polynucleotide was observed (data not shown).

Thus, the effect of contamination with Cr(III) was more pronounced when the elution was performed at a higher temperature.

EXAMPLE 24

Effect of Separation Temperature on Elution of Single-Stranded Polynucleotides

Five polynucleotides were designed. Four of them (H10, H12, H14, and H16) were designed to have complementary regions at the ends of the polynucleotides, such that an intramolecular hairpin loop could form at a non-denaturing temperature. The fifth polynucleotide (STD) was designed to have a random sequence 44 bases long. The polynucleotides were purchased from Integrated DNA Technology (Coralville, Iowa). The polynucleotides were prepared starting on a 100 nmol scale, and received desalting purification by the vendor. The identification codes and sequences are as follows:

| | | |
|---|---|---|
| H10 | 5'-TTCACAACCGCGTGTGCACTCAAAATCGGTCGGTTGTGAA-3' | (SEQ ID NO: 4) |
| H12 | 5'-TTCTCACAACCGCGTGTGCACTCAAAATCGGTCGGTTGTGAGAA-3' | (SEQ ID NO: 5) |
| H14 | 5'-GCTTCTCACAACCGCGTGTGCACTCAAAATCGGTCGGTTGTGAGAAGC-3' | (SEQ ID NO: 6) |
| H16 | 5'-TCGCTTCTCACAACCGCGTGTGCACTCAAAATCGGTCGGTTGTGAGAAGCGA-3' | (SEQ ID NO: 7) |
| STD | 5'-AGTAGAGTCCCGATGGAGATGCCACCAATGCTTTGCGCAATCTT-3' | (SEQ ID NO: 8) |

The terminal 10 bases of H10 are complementary, the terminal 12 bases of H12 are complementary, the terminal 14 bases of H14 are complementary, and the terminal 16 bases of H16 are complementary. The same sequence of randomly ordered bases was present in the central region, i.e., between the complementary ends, each of these polynucleotides.

The polynucleotides were dissolved in a sufficient quantity of 10 mM Tris (pH 8.0), 1 mM EDTA (Teknova, Half Moon Bay, Calif.) to make a 100 pmol/mL solution, based UV analysis. This was further diluted 1:5 v/v with water prior to analysis, to make a 20 pmol/μL solution.

The experiments were performed on a Transgenomic, Inc., WAVE® chromatography system, using a DNASep® Cartridge (Transgenomic, Inc., P/N 450181, S/N 121-033-10). Standard mobile phase buffers were used: Buffer A: 100 mM/L triethylammonium acetate in water; Buffer B: 100 mM/L triethylammonium acetate, 25% v/v acetonitrile in water. These were prepared from Transgenomic, Inc. Ion Pairing Reagent (2M TEM, pH 7.4, P/N 553303, and Omni-Solve acetonitrile (P/N AX0142-1, EM Science). The gradient used was as follows:

| Time (minutes) | % Buffer B |
|---|---|
| 0.0 | 5 |
| 0.5 | 5 |
| 12.5 | 53 |
| 12.6 | 100 |
| 13.1 | 100 |
| 13.2 | 5 |
| 19.2 | 5 |

2.0 μL of each sample was injected, for a sample load of 40 pmol. UV detection was used at 260 nm wavelength, and the flow rate was 0.75 mL/min.

Each polynucleotide, including the standard (STD), was analyzed by MIPC at a series of separation temperatures (at five degree intervals from 40° C. to 80° C.). As an example, the chromatograms for H10 are shown at five temperatures in FIG. 30.

Figure 31:
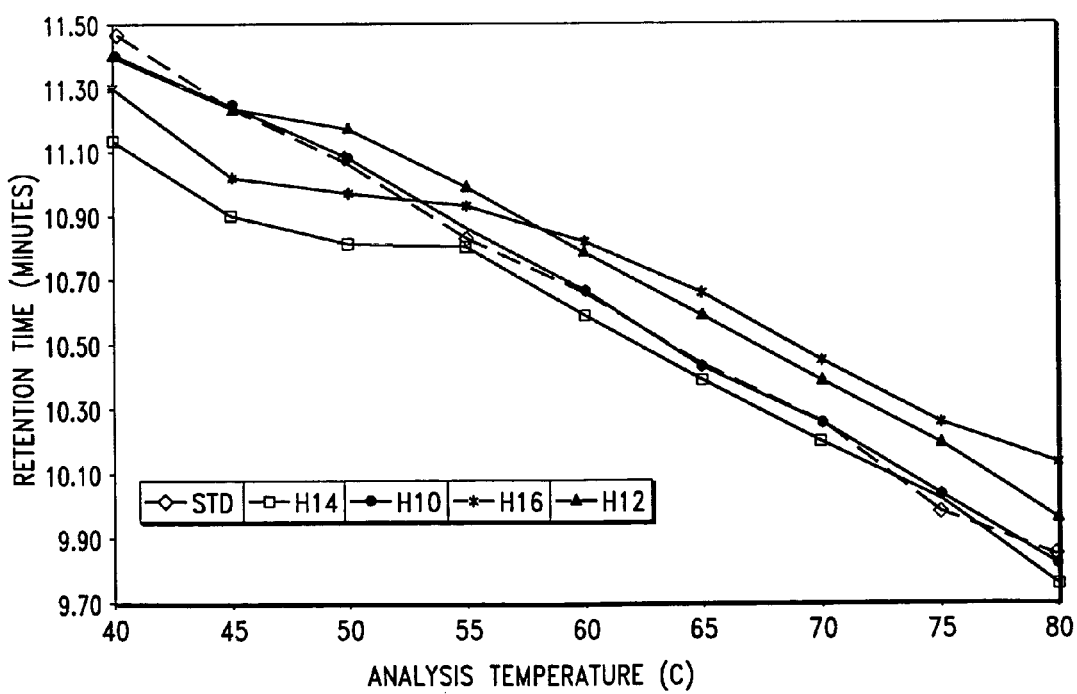
FIG. 31 illustrates a plot of MIPC retention time vs. column temperature for five different single-stranded polynucleotides.

A plot showing the retention time (Rt) for each polynucleotide, at each temperature is shown in FIG. 31 with the plots identified by the symbols shown in the legend. Both the H10 and STD polynucleotide showed approximately a linear change in retention time with temperature. All five polynucleotides showed a parallel and approximately linear relationship between Rt and temperature above about 60° C.

At temperatures below about 55° C., three of the polynucleotides (H12, H14, and H16) showed a deviation from the linear relationship. One interpretation of the data is that the divergent behavior observed for polynucleotides H12, H14, and H16 is due to "hairpin" formation, which is a type of secondary structure, at lower temperatures. To be consistent with this hypothesis, the retention time of the hairpin form would have to be shorter than that of the conventional extended form. The data above are consistent with this hypothesis: the most stable hairpin structure should occur in polynucleotide H16, with 16 complementary base pairs. For example, the temperature that induces the deviations (i.e. the transition to the denatured form which would show linear behavior) was greater for H16 than that for H14, and was greater for H14 than for H12, suggesting that the H16 structure required more energy to disrupt than H14, which required more energy that H12. No such behavior is observed for the least stable hairpin of H10, which suggested that secondary structure formation for this polynucleotide did not occur under the conditions of this experiment.

The secondary structure formed in H16, H14, or H12 would interfere with their analysis and purification, since the retention time of the hairpin structure is shorter than would be otherwise expected for these polynucleotide. A secondary structure that causes the polynucleotide to co-elute with some by-product would be undesired for efficient chromatography. For example, polynucleotide failure sequences, which are formed during the synthesis of the polynucleotide as by-products, usually elute before the full-length polynucleotide. Conducting the chromatographic separation at elevated temperature, as described herein, would tend to minimize this problem. Without wishing to be bound by theory, in the present Example, running the separation at 75° C. removed the secondary structure from polynucleotide H12, H14, and H16, which will led to improved chromatography. Higher temperature also increased column efficiency, as exemplified by the chromatograms shown in FIG. 30. For the same injection quantity, peak width was reduced at higher temperature, and peak height increased. This would result in improved resolution between components in a mixture, for example.

The skilled artisan will recognize that a wide variety of elution conditions can be varied in carrying out the separations described herein. In certain cases, the following conditions can give improved separations of single stranded polynucleotides. A wash injection solvent of no more than 2.5% acetonitrile (v/v) can be used. The ratio of the injection volume relative to the sample loop can be maximized. During a series of injections followed by elution, the column can be cleaned with 100% buffer B. The column can also be cleaned with 75% acetonitrile after a series of runs. An equilibrium time of at least 5 minutes between the end of the clean-off period and the start of a new run can be used. Preferred methods and devices for cleaning the column are described in U.S. Pat. No. 6,136,195.

EXAMPLE 25

Effect of Cr(III) Contamination on the Separation of an RNA Ladder by MIPC at 75° C.

RNA ladder (Catalog no. 15623010, Life Technologies, Rockville, Md.) containing RNA at a concentration of 1 µg/µL was diluted with four portions of water to one portion of the 1 µg/µL solution prior to injection. The injection volume was 20 µL (containing 2 µg RNA).

Figure 32:
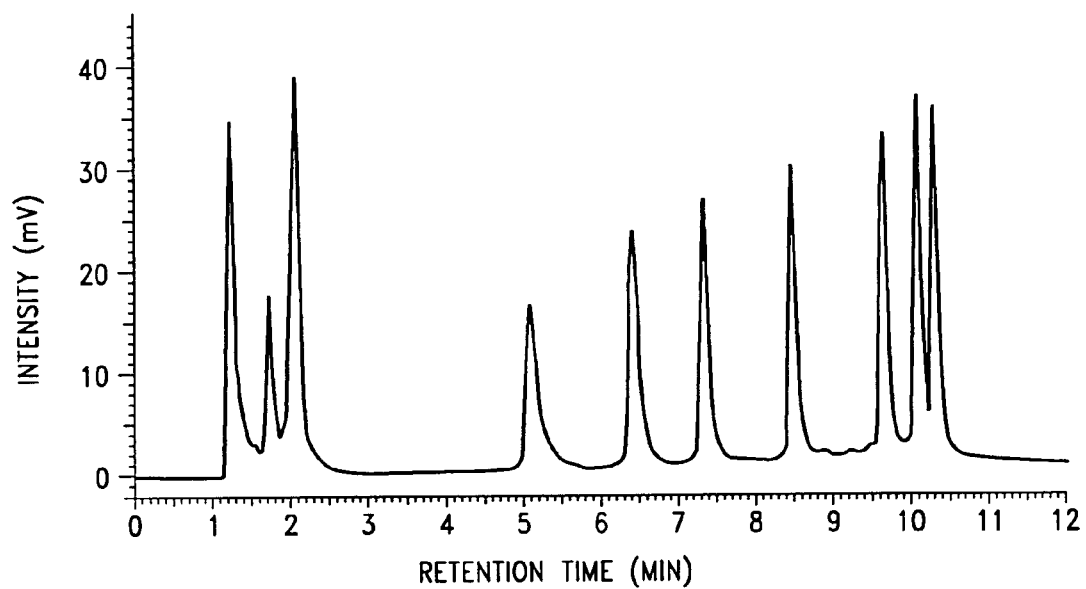
FIG. 32 illustrates an elution profile from a MIPC analysis of an RNA ladder carried out at a column temperature of 75° C.

The separation shown in FIG. 32 was obtained using a 50×7.8 mm ID column containing 2.2 µm alkylated poly (styrene-divinylbenzene) beads (DNASep®, Transgenomic, Inc.). The chromatography system included a Waters Action Analyzer LC System, a Model 484 Tunable Absorbance Detector (Waters), a Model L7200 autosampler (Hitachi), a model L7300 oven (Hitachi), and the HSM Chromatography Data System (Hitachi). The mobile phase included buffer A: 0.1 M TEM, pH 7.3; buffer B: 0.1 M TEM and 25.0% acetonitrile; buffer C: 75% acetonitrile in water.

Prior to use, the entire chromatography system was cleaned, without a column connected, with 0.05 M EDTA solution overnight at 0.5 mL/min. After this cleaning, the solvent system channels A, B and C were cleaned and rinsed with DEPC treated water (Catalog no. 08-005Z, BioWhittaker, Walkersville, Md.). Prior to injection of RNA ladder, the column was connected and the system was cleaned using 100% of buffer C for 30 min at 0.9 mL/min at 75 C°, followed by two injections of 0.5M EDTA (20 µL) (Catalog no. 750009, Research Genetics, Huntsville, Ala.) and two injections of water (20 µL). The column was eluted after each injection using the gradient as described below.

The gradient was as follows: a linear gradient of 38% to 40% B in 1 minute, followed by a linear gradient from 40% B to 56% B in 12 minutes, followed by a linear gradient of 56% to 100% B in 1 min, and then hold for 2 min. The flow rate was 0.75 mL/min.; UV detection was at 260 nm; and the column oven setting was 75° C.

The RNA fragments in the ladder were assigned the following elution times (FIG. 32): 2.05 min (0.155 kb), 5.04 min (2.8 kb), 6.35 min (4 kb), 7.26 min (5.3 kb), 8.41 min (7.8 kb), 9.58 min (1.28 kb), 10.02 min (1.52 kb), 10.23 min (1.77 kb).

Figure 33:
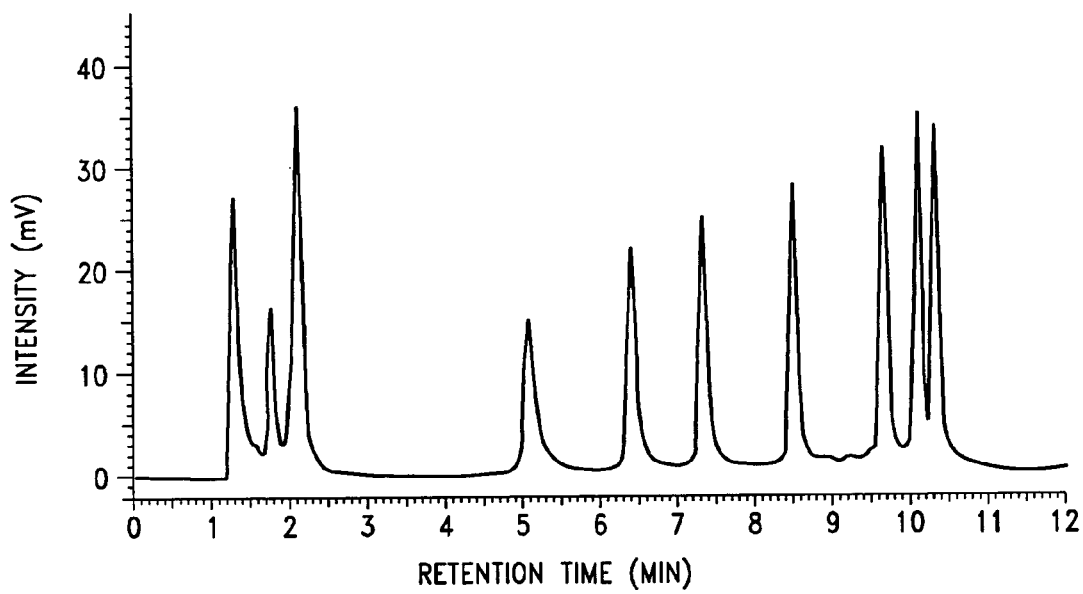
FIG. 33 illustrates an elution profile from a MIPC analysis of an RNA ladder carried out at a column temperature of 75° C. after a single injection of a Cr(III) solution onto the column used in FIG. 32.

The column was injected with 5 µL of 520 ppm Cr(III) solution and subjected to the same gradient. The Cr(III) solution was prepared by dissolving 0.125 g of $CrK(SO_4)_2 \cdot 12H_2O$ (Mallinckrodt Baker, Inc.) in 25 mL water. This was followed by another 20 µL injection of RNA ladder which gave the elution profile shown in FIG. 33. The total area under the eight RNA peaks in FIG. 33 was 94.6% as compared with the peaks in FIG. 32.

Figure 34:
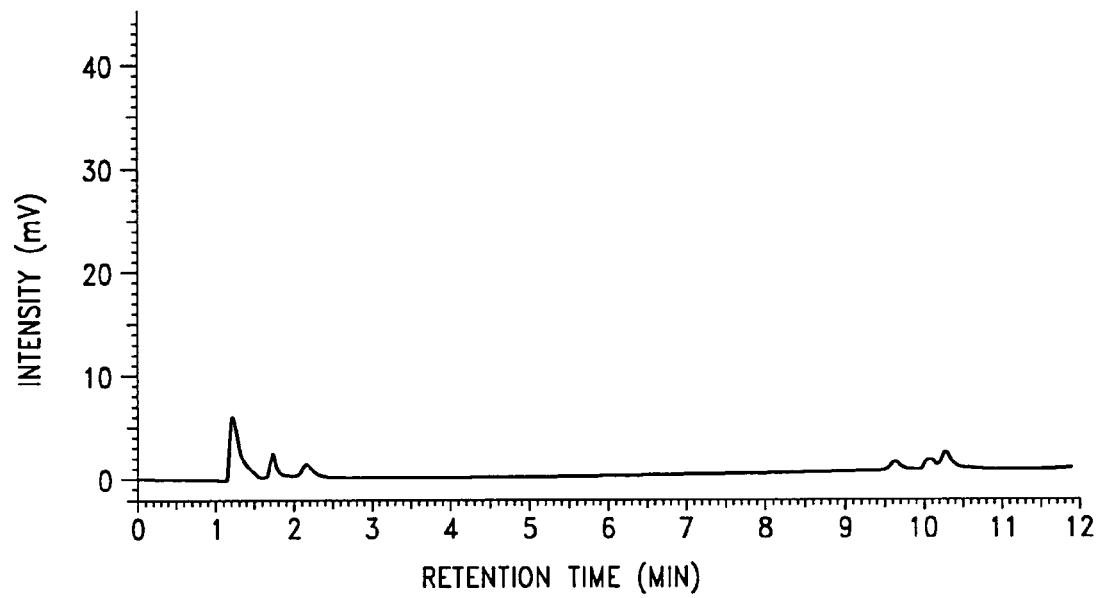
FIG. 34 illustrates an elution profile from a MIPC analysis of an RNA ladder carried out at a column temperature of 75° C. after five additional injections of a Cr(III) solution onto the column used in FIG. 33.

The column was then injected with five more 5 µL portions of the 520 ppm Cr(III) solution. Each of these was a continuous injection lasting about 0.8 min. The time between injections was 1.8 min. Before and after each injection, a constant mobile phase containing 10% B was passed through the column. After the last injection of Cr(III), a baseline in the UV absorbance was obtained, and another 20 µL of RNA ladder was injected giving the elution profile shown in FIG. 34, in which the peaks due to the RNA fragments were small or essentially undetectable.

Figure 35:
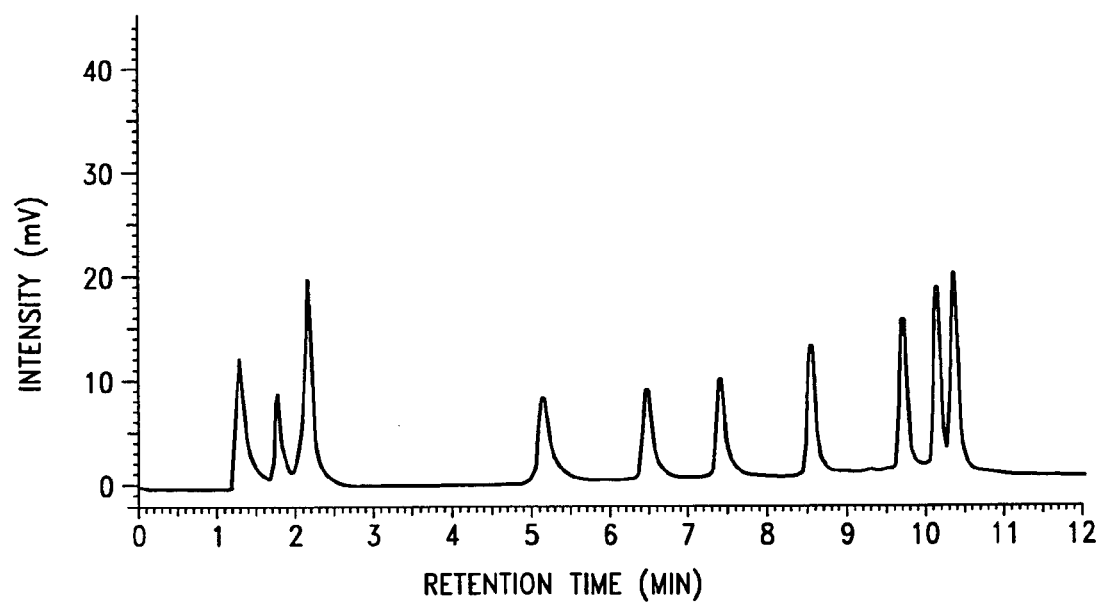
FIG. 35 illustrates an elution profile from a MIPC analysis of an RNA ladder carried out at a column temperature of 75° C. after one injection of an EDTA solution onto the column used in FIG. 34.

The column was then injected with 10 µL of a 0.1M solution of EDTA followed by gradient elution. The 0.1M EDTA solution was prepared by diluting the 0.5M solution of EDTA (Research Genetics) with water. This was followed by another 20 µL injection of RNA ladder which gave the elution profile shown in FIG. 35. The area under the peaks FIG. 35 was 47.9% as compared with the peaks in FIG. 32.

Figure 36:
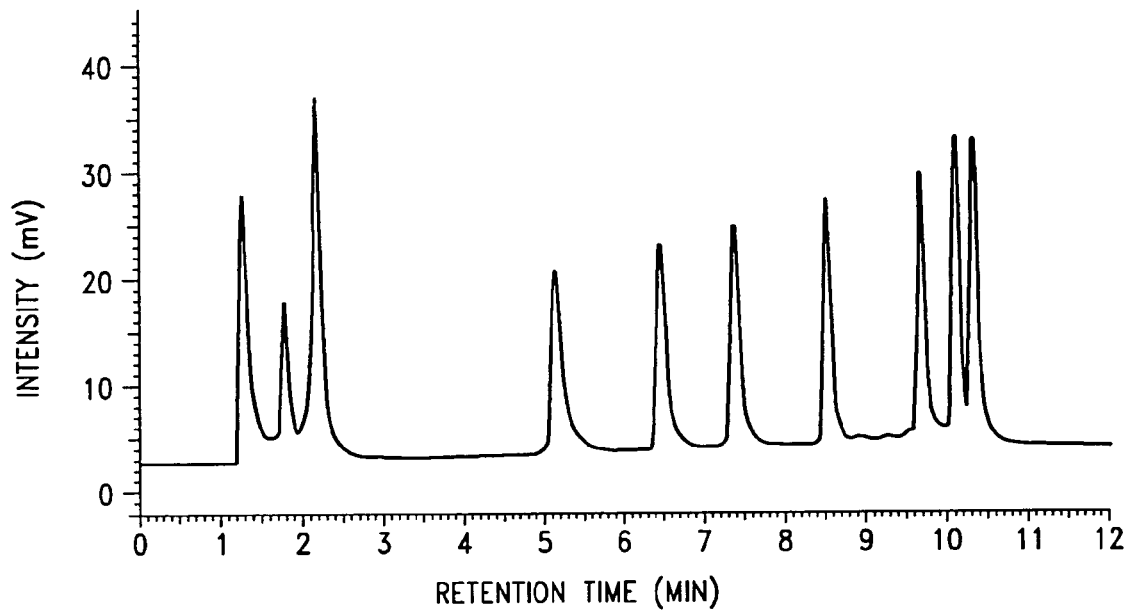
FIG. 36 illustrates an elution profile from a MIPC analysis of an RNA ladder carried out at a column temperature of 75° C. after five additional injections of an EDTA solution onto the column used in FIG. 35.

The column was then injected with five more 10 μL portions of the 0.1M EDTA solution. Each of these was a continuous injection (at a constant flow of 10% B) lasting about 0.8 min. After a constant baseline in the UV absorbance was obtained, another 20 μL of RNA ladder was injected which gave the elution profile shown in FIG. 36. The area under the peaks in FIG. 36 was 85.5% as compared with the peak in FIG. 32.

Buffers A, B, C, and the Cr(III) and EDTA solutions were prepared using DEPC treated water (BioWhittaker).

EXAMPLE 26

RNA Separation of Tobacco Plant RNA by MIPC Using a 7.8 mm ID Column

Total RNA was extracted from the flower of tobacco plant (*Nicotiana tabacum* cv. Wisconsin 38) by an acid guanidinium thiocyanate phenol-chloroform extraction method, and precipitated with 4 M lithium chloride (Chomczynski, et al., Anal. Biochem. 162:156–159 (1987) as described in Bahrami, et al., Plant Molecular Biology, 39:325–333 (1999).

MIPC analysis of total RNA from the plant extract was performed using octadecyl modified, nonporous poly (sytrene-divinylbenzene) beads packed in a 50 mm×7.8 mm ID reverse phase column (DNASEP® cartridge, Transgenomic, Inc., San Jose, Calif.) and using a WAVE® Nucleic Acid Fragment Analysis System (Transgenomic). Buffer A: 0.1 M TEM, pH 7.0; buffer B: 0.1 TEAA, 25% (v/v) acetonitrile, pH 7.0. The buffer stock solutions were obtained form Transgenomic. The gradient conditions were as follows:

| Time (min) | % B |
|---|---|
| 0.0 | 38 |
| 1.0 | 40 |
| 16 | 60 |
| 22 | 66 |
| 22.5 | 70 |
| 23 | 100 |
| 24 | 100 |
| 25 | 38 |
| 27 | 38 |

Figure 37:
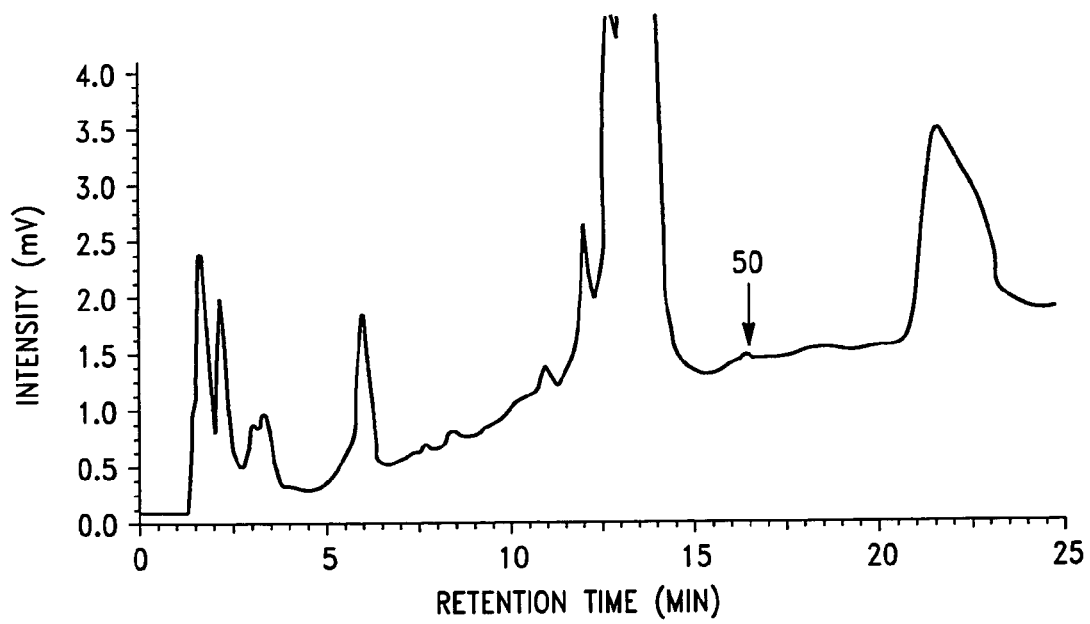
FIG. 37 is a chromatogram from a MIPC analysis of total RNA from a plant extract.

The flow rate was 0.9 mL/min and the column temperature was 75.0° C. UV detection was performed at 260 nm. The volume injected was 2 μL (containing 1.54 μg RNA). The chromatogram is shown in FIG. 37.

All references cited herein are hereby incorporated by reference in their entirety.

While the foregoing has presented specific embodiments of the present invention, it is to be understood that these embodiments have been presented by way of example only. It is expected that others will perceive and practice variations which, though differing from the foregoing, do not depart from the spirit and scope of the invention as described and claimed herein.

---

The invention claimed is:

1. A method for separating a mixture comprising single-stranded polynucleotides, the method comprising:
   a) applying said mixture to a polymeric separation medium having non-polar surfaces, wherein said surfaces are characterized by being substantially free from multivalent cations which are free to bind with the polynucleotides; and
   b) separating said mixture of polynucleotides by Matched Ion Polynucleotide Chromatography in the presence of a multivalent cation binding agent.

2. A method of claim 1 wherein said medium comprises substituted polymer beads or polymer beads substituted with a moiety comprising hydrocarbon having from 1 to 1,000,000 carbons.

3. A method of claim 2 wherein said beads comprise unsubstituted polymer beads or polymer beads substituted with a moiety selected from the group consisting of methyl, ethyl, or hydrocarbon having from 23 to 1,000,000 carbons.

4. A method of claim 1 wherein said medium has been subjected to acid wash treatment to remove any residual surface metal contaminants.

5. A method of claim 1 wherein said medium has been subjected to treatment with multivalent cation binding agent.

6. The method of claim 1 wherein the separating is performed at a temperature sufficient for fully denaturing all intramolecular and intermolecular hydrogen bonds between paired bases in a polynucleotide, or within each of the polynucleotides in a mixture.

7. A method of claim 1, including eluting said mixture with a mobile phase comprising a counterion agent and an organic solvent, wherein said organic solvent is water soluble.

8. A method of claim 7, wherein said solvent is selected from the group consisting of alcohol, acetonitrile, dimethylformamide, tetrahydrofuran, ester, ether, and mixtures of one or more thereof.

9. A method of claim 7 wherein said counterion agent is selected from the group consisting of lower alkyl primary amine, lower alkyl secondary amine, lower alkyl tertiary amine, lower trialkylammonium, quaternary ammonium salt, and mixtures of one or more thereof.

10. A method of claim 9 wherein said counterion agent is selected from the group consisting of octylammonium acetate, octadimethylammonium acetate, decylammonium acetate, octadecylammonium acetate, pyridiniumammonium acetate, cyclohexylammonium acetate, diethylammonium acetate, propylethylammonium acetate, propyidiethylammonium acetate, butylethylammonium acetate, methylhexylammonium acetate, tetramethylammonium acetate, tetraethylammonium acetate, tetrapropylammonium acetate, tetrabutylammonium acetate, dimethydiethylammonium acetate, triethylammonium acetate, tripropylammonium acetate, tributylammonium acetate, tetrapropylammonium acetate, tetrabutylammonium acetate, triethylammonium hexafluoroisopropyl alcohol, and mixtures of one or more thereof.

11. A method of claim 7 wherein said counterion agent includes anion, said anion is selected from the group consisting of acetate, carbonate, phosphate, sulfate, nitrate, propionate, formate, chloride, and bromide.

12. A method of claim 1 further including detecting polynucleotides during step (b).

13. A method of claim 1 wherein said multivalent cation comprise a member selected from the group consisting of chromium, iron, nickel, copper and mixtures of one or more thereof.

14. A method of claim 2 wherein said beads comprise a copolymer of vinyl aromatic monomers.

15. A method of claim 14 wherein said vinyl aromatic monomers are selected from the group consisting of styrene, alkyl substituted styrene, alpha-methylstyrene and alkyl substituted alpha-methylstyrene.

16. A method of claim 14 wherein said beads are comprised of a copolymer of styrene, C1–6 alkyl vinylbenzene and divinylbenzene.

17. A method of claim 1 wherein said polynucleotides comprise DNA.

18. A method of claim 1 wherein said polynucleotides comprise RNA.

19. A method of claim 6 wherein said temperature is 55° C.

20. A method of claim 6 wherein said temperature is 75° C.

21. A method of claim 6 wherein said temperature is 90° C.

22. A method of claim 6 wherein said temperature is between 70° C. and 100° C.

23. A method of claim 1 wherein said mixture comprises single-stranded polynucleotides having a length up to 2,000 nucleotides.

24. A method of claim 1 wherein said mixture comprises single-stranded polynucleotides having a length up to 20,000 nucleotides.

25. A method of claim 7 wherein said mobile phase includes the multivalent cation binding agent.

26. A method of claim 25 wherein said multivalent cation binding agent comprises EDTA.

27. A method of claim 26 wherein said eluting is performed at a temperature sufficient for fully denaturing all intramolecular and intermolecular hydrogen bonds between paired bases in a polynucleotide, or within each of the nucleotides in a mixture.

28. A method of claim 27 further including detecting polynucleotides separated during step (b).

29. A method of claim 1 wherein said medium comprises polymer beads having an average diameter of 0.5 to 100 microns, the non-polar surfaces being substituted or having bound thereto a hydrocarbon group having from 1 to 1,000,000 carbons.

30. A method of claim 29 wherein the hydrocarbon group is an alkyl group having from 1 to 24 carbons.

31. A method of claim 29 wherein the hydrocarbon group is an alkyl group having from 1 to 8 carbons.

32. A method of claim 1 wherein the non-polar surfaces are the surfaces of interstitial spaces of a polymeric monolith.

33. A method of claim 32 wherein said surfaces are unsubstituted of substituted with a hydrocarbon group having from 1 to 1,000,000 carbons.

34. A method of claim 32 wherein said polymeric monolith has been subjected to an acid wash treatment in order to substantially remove multivalent cation contaminants.

35. A method of claim 7 wherein said eluting is performed at a temperature sufficient for fully denaturing all intramolecular and intermolecular hydrogen bonds between paired bases in a polynucleotide, or within each of the polynucleotides in a mixture.

36. A method of claim 32, wherein said polymeric monolith comprises a member selected from the group consisting of monovinyl substituted aromatic compound, divinyl substituted aromatic compound, acrylate, methacrylate, polyolefin, polyester, polyurethane, polyamide, polycarbonate, fluoro-substituted ethylene, and combinations of one or more thereof.

37. A method of claim 36, wherein said polymeric monolith includes poly(glycidyl methacrylatecoethylene dimethacrylate).

38. A method for separating a mixture comprising single stranded polynucleotides, the method comprising:
  a) applying said mixture to a polymeric separation medium having non-polar surfaces, wherein said surfaces are characterized by being substantially free from multivalent cations which are free to bind with the polynucleotides; and
  b) separating said mixture of polynucleotides by Matched Ion Polynucleotide Chromatography wherein the non-polar surfaces are the surfaces of interstitial spaces of a polymeric monolith and wherein the polymeric monolith comprises a member selected from the group consisting of monovinylsubstituted aromatic compound, divinyl substituted aromatic compound, acrylate, methacrylate, polyolefin, polyester, polyurethane, polyamide, polycarbonate, fluoro-substituted ethylene, and combinations of one or more thereof, and wherein said polymeric monolith includes poly(styrene-codivinylbenzene).

39. A method of claim 32, wherein said method includes eluting said mixture from said surfaces with a mobile phase containing an organic solvent, wherein said organic solvent is water soluble.

40. A method of claim 32, wherein said method includes eluting said mixture from said surfaces with a mobile phase containing a counterion agent.

41. A method of claim 1 wherein said polynucleotides comprise chemically tagged single-stranded polynucleotides.

42. A method of claim 41 wherein said chemically tagged single-stranded polynucleotides comprise a non-polar tag.

43. A method of claim 41 wherein said chemically tagged polynucleotides comprise a fluorescent label.

44. A method of claim 42 wherein said tag comprises a hydrocarbon group, wherein said hydrocarbon group is selected from the group consisting of alkyl, cycloalkyl, aryl and arylalkyl groups.

45. A method for separating a mixture of single-stranded polynucleotide fragments having up to 2000 bases, the method comprising:
   a) applying said mixture to a polymeric separation medium having non-polar surfaces, wherein said surfaces are the surfaces of interstitial spaces of a polymeric monolith, wherein said polymeric monolith has been subjected to an acid wash treatment to remove any residual surface metal contaminants, and
   b) separating said mixture of polynucleotides at a temperature between 70° C. and 100° C. for fully denaturing all intramolecular and intermolecular hydrogen bonds between paired bases in a polynucleotide, or within each of the polynucleotides in a mixture.

* * * * *

SEQUENCE LISTING

```
<160> NUMBER OF SEQ ID NOS: 8

<210> SEQ ID NO 1
<211> LENGTH: 29
<212> TYPE: DNA
<213> ORGANISM: Artificial Sequence
<220> FEATURE:
<223> OTHER INFORMATION: Synthetic Polynucleotide

<400> SEQUENCE: 1
cgacctccct ttatcctcca cagatctca                                    29

<210> SEQ ID NO 2
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 2
taggttttat tattatattt                                              20

<210> SEQ ID NO 3
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 3
aggcactggt cagaatgaag                                              20
```

```
<210> SEQ ID NO 4
<211> LENGTH: 40
<212> TYPE: DNA
<213> ORGANISM: Artificial Sequence
<220> FEATURE:
<223> OTHER INFORMATION: Synthetic Polynucleotide

<400> SEQUENCE: 4
ttcacaaccg cgtgtgcact caaaatcggt cggttgtgaa                              40

<210> SEQ ID NO 5
<211> LENGTH: 44
<212> TYPE: DNA
<213> ORGANISM: Artificial Sequence
<220> FEATURE:
<223> OTHER INFORMATION: Synthetic Polynucleotide

<400> SEQUENCE: 5
ttctcacaac cgcgtgtgca ctcaaaatcg gtcggttgtg agaa                         44

<210> SEQ ID NO 6
<211> LENGTH: 48
<212> TYPE: DNA
<213> ORGANISM: Artificial Sequence
<220> FEATURE:
<223> OTHER INFORMATION: Synthetic Polynucleotide

<400> SEQUENCE: 6
gcttctcaca accgcgtgtg cactcaaaat cggtcggttg tgagaagc                    48

<210> SEQ ID NO 7
<211> LENGTH: 52
<212> TYPE: DNA
<213> ORGANISM: Artificial Sequence
<220> FEATURE:
<223> OTHER INFORMATION: Synthetic Polynucleotide

<400> SEQUENCE: 7
tcgcttctca caaccgcgtg tgcactcaaa atcggtcggt tgtgagaagc ga               52

<210> SEQ ID NO 8
<211> LENGTH: 44
<212> TYPE: DNA
<213> ORGANISM: Artificial Sequence
<220> FEATURE:
<223> OTHER INFORMATION: Synthetic Polynucleotide

<400> SEQUENCE: 8
agtagagtcc cgatggagat gccaccaatg ctttgcgcaa tctt                        44
```